(12) United States Patent
Lee et al.

(10) Patent No.: US 8,178,551 B2
(45) Date of Patent: May 15, 2012

(54) ORALLY BIOAVAILABLE PRODRUGS OF (+)-3-HYDROXYMORPHINAN FOR PARKINSON'S DISEASE PREVENTION OR TREATMENT

(75) Inventors: Jinhwa Lee, Yongin-si (KR); Jeongmin Kim, Yongin-si (KR); Myung Eun Jung, Yongin-si (KR); Jong Yup Kim, Yongin-si (KR); Kwang-Seop Song, Yongin-si (KR); Eun Jung Son, Yongin-si (KR); Suk Ho Lee, Yongin-si (KR); Ho Kyun Han, Yongin-si (KR); Min Ju Kim, Yongin-si (KR); MinWoo Lee, Yongin-si (KR)

(73) Assignee: Green Cross Corporation, Gyeonggi-Do (KR)

( * ) Notice: Subject to any disclaimer, the term of this patent is extended or adjusted under 35 U.S.C. 154(b) by 450 days.

(21) Appl. No.: 12/530,444

(22) PCT Filed: Mar. 7, 2008

(86) PCT No.: PCT/KR2008/001306
§ 371 (c)(1),
(2), (4) Date: Sep. 8, 2009

(87) PCT Pub. No.: WO2008/111767
PCT Pub. Date: Sep. 18, 2008

(65) Prior Publication Data
US 2010/0113500 A1 May 6, 2010

Related U.S. Application Data

(60) Provisional application No. 60/893,930, filed on Mar. 9, 2007.

(51) Int. Cl.
*A61K 31/439* (2006.01)
*C07D 221/28* (2006.01)

(52) U.S. Cl. .......................... 514/289; 546/74
(58) Field of Classification Search .................. 514/289; 546/74
See application file for complete search history.

(56) References Cited

OTHER PUBLICATIONS

Becker, G., et al., "Early diagnosis of Parkinson's disease," J. Neurol., 249, 2002,III/40-III/48.
Kim, H.C., et al., "New morphinan derivatives with negligible psychotropic effects attenuate convulsions induced by maximal electroshock in mice," Life Sciences, 72, 2003, 1883-1895.
Zhang, W., et al., "3-Hydroxymorphinan, a metabolite of dextromethorphan, protects nigrostriatal pathway against MPTP-elicited damage both in vivo and in vitro," FASEB J., 20, 2006, pp. 2496-2511.
Zhang, W., et al., "3-Hydroxymorphinan is neurotrophic to dopaminergic neurons and is also neuroprotective against LPS-induced neurotoxicity," FASEB J., 19, 2005, pp. 395-397.
Thomas, J.D., et al., "Overcoming steric effects in the coupling reaction of alkyloxycarbonyloxymethyl (AOCOM) halides with phenols: an efficient synthesis of AOCOM phenolic prodrugs," Tetrahedron Letters, 48, 2007, pp. 109-112.
Hughes, A., et al., "Accuracy of clinical diagnosis of idiopathic Parkinson's disease: a clinico-pathological study of 100 cases," J. Neurology, Neurosurgery and Psychiatry, 55, 1992, pp. 181-184.
Dawson, T.M., "Neuroprotective and neurorestorative strategies for Parkinson's disease," Nature Neuroscience Supplement, 5, 2002, pp. 1058-1061.

*Primary Examiner* — Charanjit Aulakh
(74) *Attorney, Agent, or Firm* — Sughrue Mion, PLLC

(57) ABSTRACT

The present invention is directed to a novel prodrug of (+)-3-hydroxymorphinan compound of formula (I) or a pharmaceutically acceptable salt thereof, a method for preparing the same, and its use for preventing or treating Parkinson's disease.

7 Claims, 2 Drawing Sheets

ORALLY BIOAVAILABLE PRODRUGS OF (+)-3-HYDROXYMORPHINAN FOR PARKINSON'S DISEASE PREVENTION OR TREATMENT

FIELD OF THE INVENTION

The present invention relates to an orally bioavailable, novel prodrug of (+)-3-hydroxymorphinan which is effective as a neuroprotective agent for Parkinson's disease.

BACKGROUND OF THE INVENTION

There are approximately 100 million people in the world and 800,000 people in the United States alone with Parkinson's disease (PD).

Parkinson's disease is a result of chronic progressive degeneration of neurons, the cause of which has not yet completely been clarified. While the primary cause of Parkinson disease is not known, it is characterized by degeneration of dopaminergic neurons of the substantia nigra (SN). The substantia nigra is a portion of the lower brain, or brain stem that helps control voluntary movements. The shortage of dopamine in the brain caused by the loss of these neurons is believed to cause the observable disease symptoms. Clinically, it manifests in the form of the cardinal symptoms resting tremors, rigor, bradykinesia, and postural instability.

Levodopa, dopamine agonists such as rotigotine, pramipexol, bromocriptine, ropinirol, cabergoline, pergolide, apomorphine and lisuride, anticholinergics, NMDA antagonists, β-blocker as well as the MAO-B inhibitor selegiline and the COMT inhibitor entacapone are used as medicines for relief from the motor symptoms. Most of these agents intervene in the dopamine and/or choline signal cascade and thereby symptomatically influence the Parkinson-typical movement disorders.

In the present therapy for the Parkinson's disease, treatment is initiated after the appearance of the cardinal symptoms. In general, Parkinson's disease is said to be clinically evident if at least two of the four cardinal symptoms (bradykinesia, resting tremors, rigor, and postural instability) are detected and respond to L-dopa (Hughes, J Neurol Neurosurg Psychiatry 55, 1992, 181). Unfortunately, the motor function disorders in Parkinson patients become apparent only after about 70-80% of the dopaminergic neurons in the substantia nigra (SN) are irreparably damaged (Becker et al, J Neurol 249, 2002, Suppl 3:III, 40; Hornykiewicz, Encyclopaedia of Life Science 2001, 1). Chances of a therapy with lasting effects are very bleak at that point. Hence, it is desirable to initiate the therapy as early as possible.

Current clinical observations as well as anatomical and genetic research show that diagnosis of Parkinson patients at an early stage and identification of high risk patients is possible. With that an opportunity arises for influencing the disease process at a point of time when more neurons are still there, rather than at the time of appearance of several cardinal motor symptoms of the Parkinson's disease, and thereby for protecting a quantitatively greater number of neurons. One can expect that the administration of an effective neuroprotective agent at an early stage will significantly delay the process of the development of the disease: The sooner the therapy is initiated, the higher are the chances of a long lasting prevention of the onset of symptoms, which degrade the quality of life.

Hence, such remedies are needed that not only influence the dopaminergic transmission and alleviate the symptoms of the Parkinson's disease in advanced stages, but also reverse, prevent, or at least significantly delay the dopaminergic neuron extinction in the early, to a great extent motor-asymptomatic, Parkinson stages (Dawson, Nature Neuroscience Supplement 5, 2002, 1058).

(+)-3-Hydroxymorphinan ((+)-3-HM) and its derivatives have shown the neuroprotective property in 1-methyl-4-phenyl-1,2,3,6-tetrahydropyridine (MPTP) models for Parkinson's disease. In this animal model, daily injections with (+)-3-HM or its analogs showed that dopamine (DA) neurons in substantia nigra pars compacta have been protected and DA levels in striatum has been restored (US Patent Publication No. 2005-0256147 A1; International Patent Publication No. WO2005/110412; Zhang et al, FASEB J. 2006 Dec. 20(14): 2496-2511; Zhang et al, FASEB J. 2005 Mar. 19(3):395-397; and Kim et al. Life Science 72 (2003) 1883-1895). However, (+)-3-HM and its derivatives are efficacious only if they are administered intraperitoneally or intravenously.

The present invention relates to provide novel prodrugs of (+)-3-hydroxymorphinan which are effective as a neuroprotective agent for Parkinson's disease, when they are delivered orally.

SUMMARY OF THE INVENTION

It is a primary object of the present invention to provide a novel prodrug of (+)-3-hydroxymorphinan compound of formula (I) or a pharmaceutically acceptable salt thereof, which is effective as a neuroprotective agent for Parkinson's disease.

It is another object of the present invention to provide a method for preparing the inventive compound.

It is another object of the present invention to provide a pharmaceutical composition for treating or preventing Parkinson's disease, comprising the inventive compound as an active ingredient.

BRIEF DESCRIPTION OF DRAWINGS

The above and other objects and features of the present invention will become apparent from the following description of the invention taken in conjunction with the following accompanying drawings, which respectively show.

DETAILED DESCRIPTION OF THE INVENTION

Figure 1:
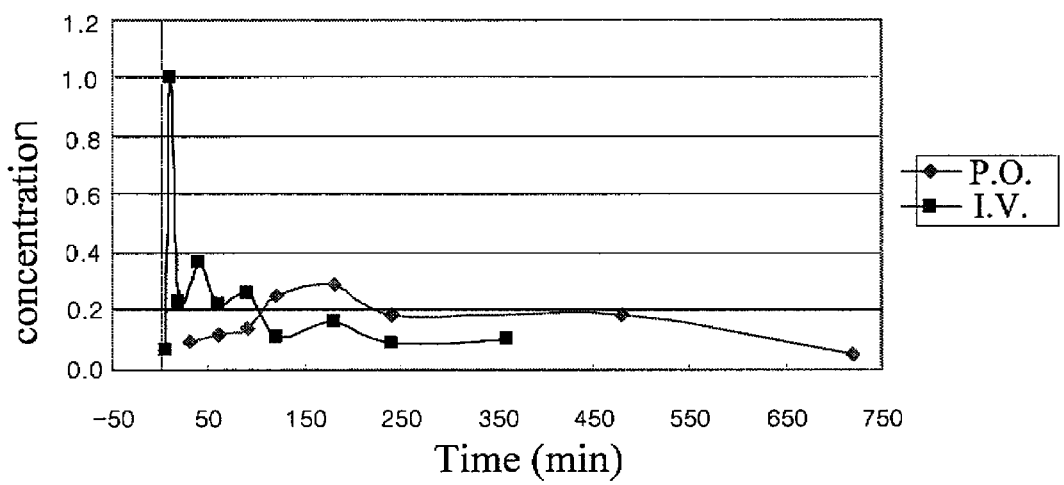
FIG. 1 illustrates pharmacokinetic profile of a compound of Example 2 in mice.

In accordance with one aspect of the present invention, there are provided a compound of formula (I) or a pharmaceutically acceptable salt thereof and a method for preparing same:

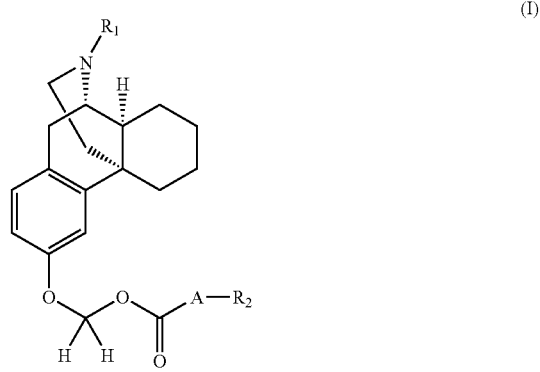

(I)

wherein,

A is a direct bond or oxygen;

$R_1$ is selected from the group consisting of hydrogen, —C(O)OC$_{1-10}$ alkyl, substituted —C(O)OC$_{1-10}$ alkyl, —C(O)OC$_{1-4}$ alkyl-Ar and substituted —C(O)OC$_{1-4}$ alkyl-Ar, Ar being selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidinyl, all of which are optionally substituted by one or more Z groups, Z being independently selected from the group consisting of $C_{1-4}$ alkyl, $C_{1-4}$ alkoxy, —(CH$_2$)$_m$C(O)OR$_3$, C(O)NR$_3$R$_4$, —CN, —(CH$_2$)$_n$OH, —NO$_2$, F, Cl, Br, I, —NR$_3$R$_4$ and NHC(O)R$_3$, wherein m is 0 to 4, n is 0 to 4, $R_3$ is hydrogen, $C_{1-6}$ alkyl or substituted $C_{1-6}$ alkyl, and $R_4$ is selected from the group consisting of $C_{1-6}$ alkyl, substituted $C_{1-6}$ alkyl, —CH$_2$Ar and Ar, Ar being as defined above; and $R_2$ is selected from the group consisting of $C_{1-10}$ alkyl, substituted $C_{1-10}$ alkyl, $C_{3-10}$ carbocycle, substituted $C_{3-10}$ carbocycle, (CH$_2$)$_n$-phenyl and substituted (CH$_2$)$_n$-phenyl, wherein n is 0 to 4.

One embodiment of the present invention is to provide a compound of formula (Ia) or a pharmaceutically acceptable salt thereof:

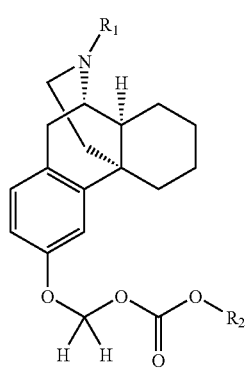

(Ia)

wherein $R_1$ and $R_2$ have the same meanings as defined above.

Another embodiment of the present invention is to provide a compound of formula (Ib) or a pharmaceutically acceptable salt thereof:

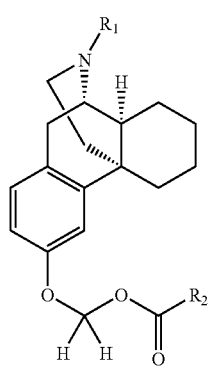

(Ib)

wherein $R_1$ and $R_2$ have the same meanings as defined above.

The preferred compounds of formula (I) are those compounds wherein $R_1$ is hydrogen, —C(O)OC$_{1-4}$ alkyl-Ar or substituted —C(O)OC$_{1-4}$ alkyl-Ar, Ar being phenyl or naphthyl, both of which are optionally substituted by one or more Z groups, Z being independently selected from the group consisting of $C_{1-4}$ alkyl, $C_{1-4}$ alkoxy, —(CH$_2$)$_m$C(O)OR$_3$, C(O)NR$_3$R$_4$, —CN, —(CH$_2$)$_n$OH, —NO$_2$, F, Cl, Br, I, —NR$_3$R$_4$ and NHC(O)R$_3$, wherein m is 0 to 4, n is 0 to 4, $R_3$ is hydrogen, $C_{1-6}$ alkyl or substituted $C_{1-6}$ alkyl, and $R_4$ is selected from the group consisting of $C_{1-6}$ alkyl, substituted $C_{1-6}$ alkyl, —CH$_2$Ar and Ar, Ar being as defined above; and $R_2$ is selected from the group consisting of $C_{1-10}$ alkyl, substituted $C_{1-10}$ alkyl, $C_{3-10}$ carbocycle, substituted $C_{3-10}$ carbocycle, (CH$_2$)$_n$-phenyl and substituted (CH$_2$)$_n$-phenyl, wherein n is 0 to 4.

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents.

As used herein, the term "carbocycle" refers to a non-aromatic cyclic hydrocarbon radical composed of three to seven carbon atoms or fused bicyclic hydrocarbon radical in which each cycle refers to a non-aromatic cyclic hydrocarbon radical composed of three to seven carbon atoms. Five- to seven-membered rings may contain a double bond in the ring structure. Exemplary "carbocycle" groups include, but are not limited to, cyclopropyl, cyclobutyl, cyclopentyl, cyclopentenyl, cyclohexyl, and cycloheptyl. Exemplary "fused bicycle" groups include, but are not limited to, decahydronaphthyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, aryl, and aryloxy.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, and aroyloxy. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl and phenanthryl, as well as substituted derivatives thereof.

As used herein, the term "alkoxy" refers to the group —OR$_a$, where R$_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein the term "aralkoxy" refers to the group —OR$_a$R$_b$, wherein R$_a$ is alkyl and R$_b$ is aryl as defined above.

As used herein the term "aryloxy" refers to the group —OR$_b$, wherein R$_b$ is aryl as defined above.

It is to be understood that the present invention also includes a pharmaceutically acceptable salt and an acid addition salt of the inventive compound, such as a hydrochloride, trifluoroacetic acid, formic acid, citric acid, fumaric acid, fumarate mono-sodium, p-toluenesulfonic acid, stearic acid, citrate di-sodium, tartaric acid, malic acid, lactic acid, succinic acid, or salicylic acid addition salt. The compounds of the present invention may contain one or more asymmetric carbon atoms and may exist in racemic and optically active forms. All of these compounds and diastereomers are incorporated within the scope of the present invention.

Compounds especially useful in the present invention are selected from the group consisting of:

(+)-Isopropyl(morphinan-3-yloxy)methyl carbonate;
(+)-(Morphinan-3-yloxy)methyl propyl carbonate;
(+)-Cyclopropylmethyl(morphinan-3-yloxy)methyl carbonate;
(+)-Cyclopentyl(morphinan-3-yloxy)methyl carbonate;
(+)-Cyclohexyl(morphinan-3-yloxy)methyl carbonate;
(+)-Cyclohexylmethyl(morphinan-3-yloxy)methyl carbonate;
(+)-Heptan-4-yl(morphinan-3-yloxy)methyl carbonate;
(+)-Decahydronaphthalen-2-yl(morphinan-3-yloxy)methyl carbonate;
(+)-Decahydronaphthalen-1-yl(morphinan-3-yloxy)methyl carbonate;
(+)-Cyclopentylmethyl(morphinan-3-yloxy)methyl carbonate TFA;
(+)-Cyclobutylmethyl(morphinan-3-yloxy)methyl carbonate TFA;
(+)-2-Ethylhexyl(morphinan-3-yloxy)methyl carbonate TFA;
(+)-Butyl(morphinan-3-yloxy)methyl carbonate TFA;
(+)-Isobutyl(morphinan-3-yloxy)methyl carbonate TFA;
(+)-sec-Butyl(morphinan-3-yloxy)methyl carbonate TFA;
(+)-Cycloheptyl(morphinan-3-yloxy)methyl carbonate TFA;
(+)-(Morphinan-3-yloxy)methyl phenethyl carbonate TFA;
(+)-(Morphinan-3-yloxy)methyl 1-phenylpropan-2-yl carbonate TFA;
(+)-Ethyl(morphinan-3-yloxy)methyl carbonate TFA;
(+)-Methyl(morphinan-3-yloxy)methyl carbonate TFA;
(+)-Cyclobutyl(morphinan-3-yloxy)methyl carbonate TFA;
(+)-Hexyl(morphinan-3-yloxy)methyl carbonate TFA
(+)-(Morphinan-3-yloxy)methyl pentan-2-yl carbonate TFA
(+)-Decyl(morphinan-3-yloxy)methyl carbonate TFA;
(+)-(Morphinan-3-yloxy)methyl isobutyrate;
(+)-(Morphinan-3-yloxy)methyl pivalate;
(+)-(Morphinan-3-yloxy)methyl pivalate TFA;
(+)-(Morphinan-3-yloxy)methyl 3,3-dimethylbutanoate TFA;
(+)-(Morphinan-3-yloxy)methyl hexanoate TFA;
(+)-(Morphinan-3-yloxy)methyl 2-propylpentanoate TFA;
(+)-(Morphinan-3-yloxy)methyl 2-ethylbutanoate TFA;
(+)-(Morphinan-3-yloxy)methyl cyclohexanoate TFA;
(+)-(Morphinan-3-yloxy)methyl cyclopentanoate TFA;
(+)-(Morphinan-3-yloxy)methyl 2-ethylhexanoate TFA;
(+)-(Morphinan-3-yloxy)methyl butanoate TFA;
(+)-(Morphinan-3-yloxy)methyl pentanoate TFA;
(+)-(Morphinan-3-yloxy)methyl 2-methylbutanoate TFA;
(+)-(Morphinan-3-yloxy)methyl cyclopropanecarboxylate TFA;
(+)-(Morphinan-3-yloxy)methyl 3-methylbutanoate TFA;
(+)-(Morphinan-3-yloxy)methyl 2-phenylbutanoate TFA;
(+)-(Morphinan-3-yloxy)methyl 1-adamantanecarboxylate TFA;
(+)-(Morphinan-3-yloxy)methyl acetate TFA;
(+)-(Morphinan-3-yloxy)methyl 3-cylcohexylpropanoate TFA;
(+)-(Morphinan-3-yloxy)methyl 3,5,5-trimethylhexanoate TFA;
(+)-Isopropyl(morphinan-3-yloxy)methyl carbonate TFA;
(+)-Isopropyl(morphinan-3-yloxy)methyl carbonate L-(+)-tartaric acid;
(+)-Isopropyl(morphinan-3-yloxy)methyl carbonate HCl;
(+)-Isopropyl(morphinan-3-yloxy)methyl carbonate formic acid;
(+)-Isopropyl(morphinan-3-yloxy)methyl carbonate citric acid;
(+)-Isopropyl(morphinan-3-yloxy)methyl carbonate fumaric acid;
(+)-Isopropyl(morphinan-3-yloxy)methyl carbonate fumaric acid mono-Na;
(+)-Isopropyl(morphinan-3-yloxy)methyl carbonate 4-methylbenzenesulfonic acid;
(+)-Isopropyl(morphinan-3-yloxy)methyl carbonate stearic acid;
(+)-Isopropyl(morphinan-3-yloxy)methyl carbonate citric acid di-Na;
(+)-Isopropyl(morphinan-3-yloxy)methyl carbonate L-(−)-malic acid;
(+)-Isopropyl(morphinan-3-yloxy)methyl carbonate L-(+)-lactic acid;
(+)-Isopropyl(morphinan-3-yloxy)methyl carbonate succinic acid;
(+)-Isopropyl(morphinan-3-yloxy)methyl carbonate salicylic acid;
(+)-(Morphinan-3-yloxy)methyl pivalate succinic acid;
(+)-(Morphinan-3-yloxy)methyl pivalate HCl;
(+)-(Morphinan-3-yloxy)methyl pivalate formic acid;
(+)-(Morphinan-3-yloxy)methyl pivalate citric acid;
(+)-(Morphinan-3-yloxy)methyl pivalate fumaric acid;
(+)-(Morphinan-3-yloxy)methyl pivalate fumaric acid mono-Na;
(+)-(Morphinan-3-yloxy)methyl pivalate 4-methylbenzenesulfonic acid;
(+)-(Morphinan-3-yloxy)methyl pivalate stearic acid;
(+)-(Morphinan-3-yloxy)methyl pivalate citric acid di-Na;
(+)-(Morphinan-3-yloxy)methyl pivalate L-(+)-tartaric acid;
(+)-(Morphinan-3-yloxy)methyl pivalate L-(−)-malic acid;
(+)-(Morphinan-3-yloxy)methyl pivalate L-(+)-lactic acid;
(+)-(Morphinan-3-yloxy)methyl pivalate salicylic acid;
(+)-[N-(Benzyloxycarbonyl)morphinan-3-yloxy]methyl isopropyl carbonate;
(+)-[N-(Benzyloxycarbonyl)morphinan-3-yloxy]methyl cyclopentyl carbonate;
(+)-[N-(Benzyloxycarbonyl)morphinan-3-yloxy]methyl cyclohexyl carbonate;
(+)-[N-(Benzyloxycarbonyl)morphinan-3-yloxy]methyl decahydronaphthalen-1-yl carbonate;
(+)-[N-(Benzyloxycarbonyl)morphinan-3-yloxy]methyl cyclopentylmethyl carbonate;
(+)-[N-(Benzyloxycarbonyl)morphinan-3-yloxy]methyl cyclobutylmethyl carbonate;
(+)-[N-(Benzyloxycarbonyl)morphinan-3-yloxy]methyl 2-ethylhexyl carbonate;
(+)[N-(Benzyloxycarbonyl)morphinan-3-yloxy]methyl butyl carbonate;
(+)-[N-(Benzyloxycarbonyl)morphinan-3-yloxy]methyl isobutyl carbonate;

(+)-[N-(Benzyloxycarbonyl)morphinan-3-yloxy]methyl sec-butyl carbonate;
(+)-[N-(Benzyloxycarbonyl)morphinan-3-yloxy]methyl cycloheptyl carbonate;
(+)-[N-(Benzyloxycarbonyl)morphinan-3-yloxy]methyl phenethyl carbonate;
(+)-[N-(Benzyloxycarbonyemorphinan-3-yloxy]methyl 1-phenylpropan-2-yl carbonate;
(+)-[N-(Benzyloxycarbonyl)morphinan-3-yloxy]methyl ethyl carbonate;
(+)-[N-(Benzyloxycarbonyl)morphinan-3-yloxy]methyl methyl carbonate;
(+)-[N-(Benzyloxycarbonyl)morphinan-3-yloxy]methyl cyclobutyl carbonate;
(+)-[N-(Benzyloxycarbonyl)morphinan-3-yloxy]methyl hexyl carbonate;
(+)-[N-(Benzyloxycarbonyl)morphinan-3-yloxy]methyl pentan-2-yl carbonate;
(+)-[N-(Benzyloxycarbonyl)morphinan-3-yloxy]methyl isobutyrate;
(+)-[N-(Benzyloxycarbonyl)morphinan-3-yloxy]methyl pivalate;
(+)-[N-(Benzyloxycarbonyl)morphinan-3-yloxy]methyl hexanoate;
(+)-[N-(Benzyloxycarbonyl)morphinan-3-yloxy]methyl 2-propylpentanoate;
(+)-[N-(Benzyloxycarbonyl)morphinan-3-yloxy]methyl 2-ethylbutanoate;
(+)-[N-(Benzyloxycarbonyl)morphinan-3-yloxy]methyl cyclohexanoate;
(+)-[N-(Benzyloxycarbonyl)morphinan-3-yloxy]methyl cyclopentanoate;
(+)-[N-(Benzyloxycarbonyemorphinan-3-yloxy]methyl 2-ethylhexanoate;
(+)-[N-(Benzyloxycarbonyl)morphinan-3-yloxy]methyl butanoate;
(+)-[N-(Benzyloxycarbonyl)morphinan-3-yloxy]methyl pentanoate;
(+)-[N-(Benzyloxycarbonyl)morphinan-3-yloxy]methyl 2-methylbutanoate;
(+)-[N-(Benzyloxycarbonyl)morphinan-3-yloxy]methyl cyclopropanecarboxylate;
(+)-[N-(Benzyloxycarbonyl)morphinan-3-yloxy]methyl 3-methylbutanoate;
(+)-[N-(Benzyloxycarbonyl)morphinan-3-yloxy]methyl 2-phenylbutanoate;
(+)-[N-(Benzyloxycarbonyl)morphinan-3-yloxy]methyl 1-adamantanecarboxylate; and
(+)-[N-(Benzyloxycarbonyl)morphinan-3-yloxy]methyl 3,5,5-trimethylhexanoate.

General Synthesis of the Compounds of Formula (I)

The compound of formula (Ia) may be prepared by, for example, (i) reacting a (+)-3-hydroxymorphinan ((+)-3-HM) hydrobromide (1) with CbzCl in aqueous NaOH to provide (+)-N-17-Cbz-3-hydroxymorphinan of formula (2), and (ii) alkylating the resulting product with iodomethyl alkyl carbonate (3) in the presence of an appropriate base such as cesium carbonate, or sodium hydride, or DBU to yield alkyl phenoxymethyl carbonate of formula (4), and finally (iii) deprotecting N-17-Cbz group of the resulting product to obtain a compound of formula (Ia), as shown in Reaction Scheme 1.

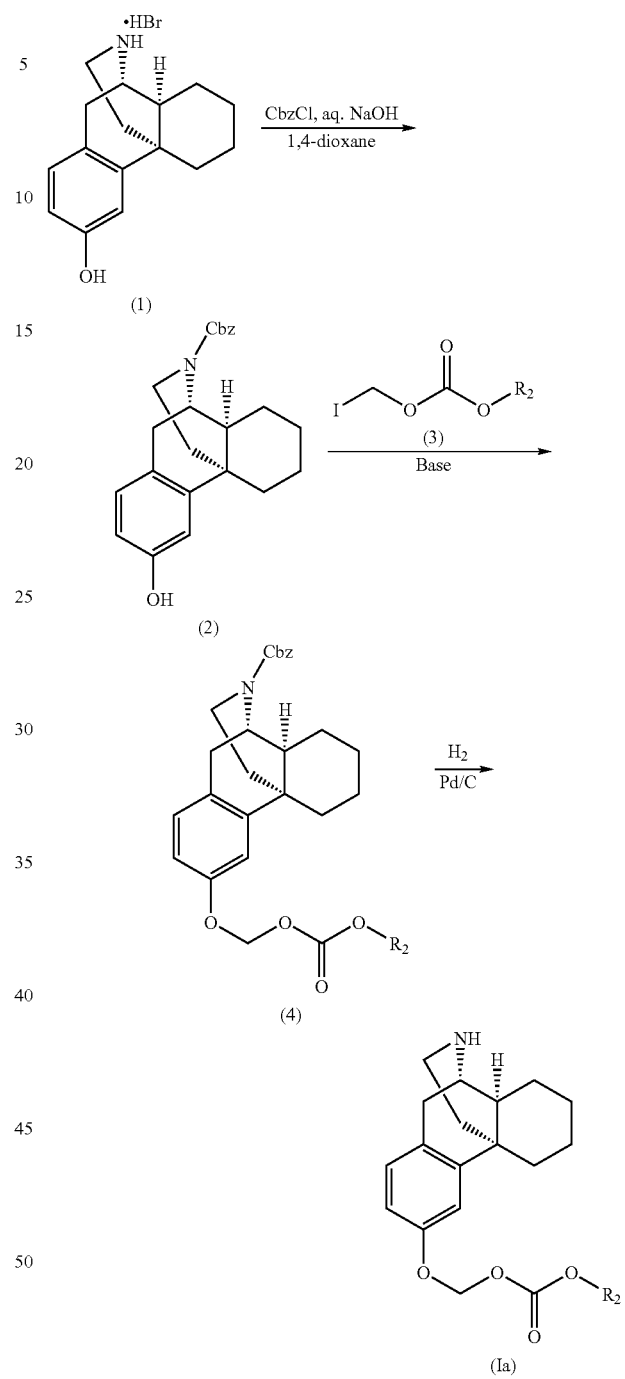

wherein $R_2$ has the same meanings as defined above.

The iodomethyl alkyl carbonate derivative (3) used as a starting material in preparing the compound of formula (Ia) may be prepared by a conventional method, e.g., by treating an chloroformic acid chloromethyl ester (5) with an alcohol in anhydrous ether with an organic base such as pyridine or DMAP to produce a corresponding chloromethyl alkyl carbonate (6), reacting the resulting product with sodium iodide in an appropriate solvent such as acetone or acetonitrile to provide a corresponding iodomethyl alkyl carbonate (3) (see Rigel Pharmaceuticals, Inc., US2006/247287 A1), as shown in Reaction Scheme 2.

Reaction Scheme 2

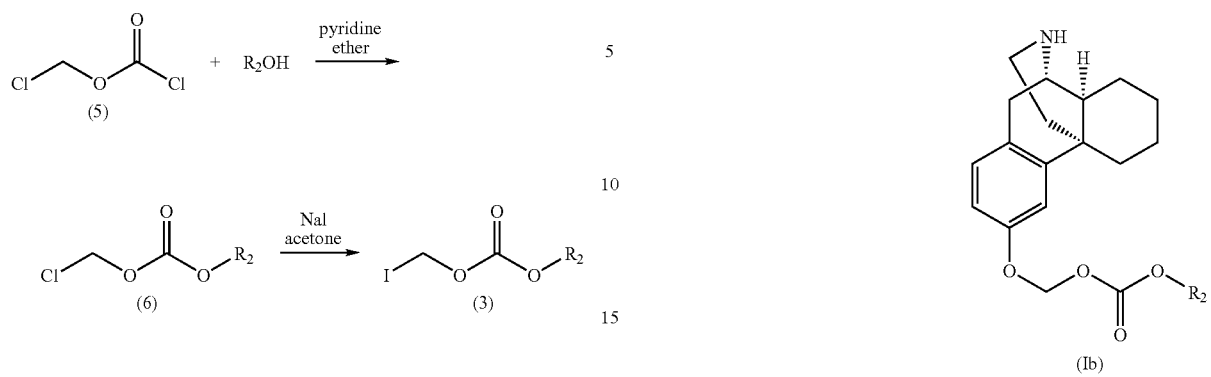

Reaction Scheme 3

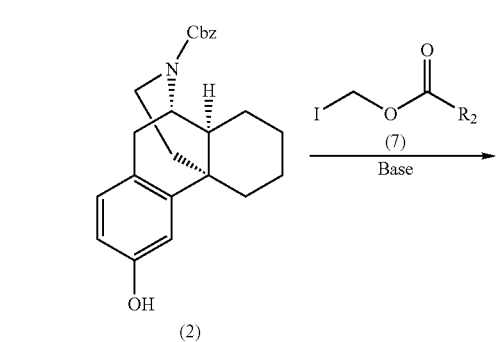

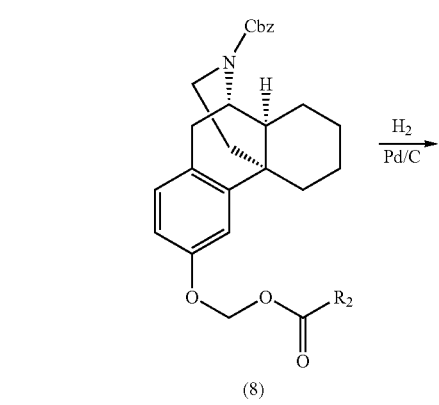

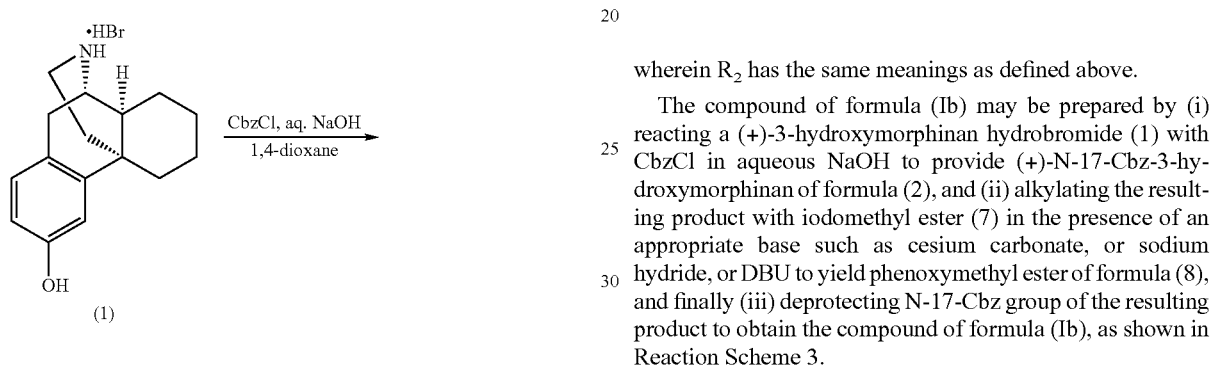

wherein $R_2$ has the same meanings as defined above.

The compound of formula (Ib) may be prepared by (i) reacting a (+)-3-hydroxymorphinan hydrobromide (1) with CbzCl in aqueous NaOH to provide (+)-N-17-Cbz-3-hydroxymorphinan of formula (2), and (ii) alkylating the resulting product with iodomethyl ester (7) in the presence of an appropriate base such as cesium carbonate, or sodium hydride, or DBU to yield phenoxymethyl ester of formula (8), and finally (iii) deprotecting N-17-Cbz group of the resulting product to obtain the compound of formula (Ib), as shown in Reaction Scheme 3.

Reaction Scheme 4

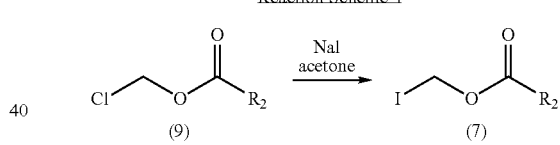

wherein $R_2$ has the same meanings as defined above.

The iodomethyl ester derivative (7) used as a starting material in preparing the compound of formula (Ib) may be prepared by treating an chloromethyl ester (9) with sodium iodide in an appropriate solvent such as acetone or acetonitrile to provide a corresponding iodomethyl ester (7) as shown in Reaction Scheme 4 (see Bristol-Myers Squibb Company, U.S. Pat. No. 5,470,845 A1).

Alternatively, the preparation of compounds of the formula (Ib) is illustrated in Reaction Scheme 5 wherein, $R_2$ has the same meanings as defined above. The compound of formula (2) is deprotonated with a base such as sodium hydride in an appropriate solvent such as HMPA and then alkylated with chloromethyl methyl sulfide to provide the thiomethyl methyl ether (9). Treatment of the compound of formula (9) with a chlorinating agent such as sulfuryl chloride provides the chloromethyl ether of formula (10) which is then treated with a carboxylic acid in the presence of a suitable base such as cesium carbonate to provide the phenoxymethyl ester of formula (8). Finally, deprotecting N-17-Cbz group of the resulting product using Pd on charcoal under hydrogen atmosphere yields the compound of formula (Ib).

Reaction Scheme 5

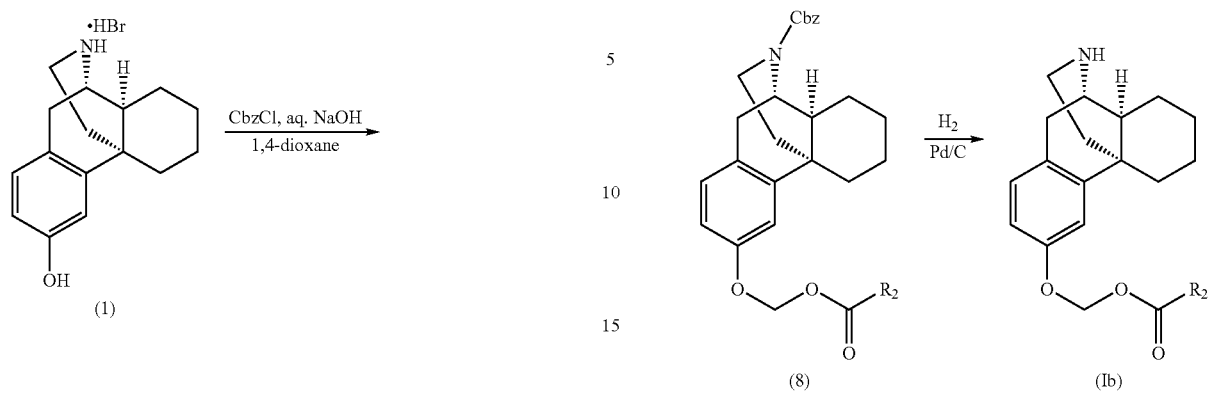

Formation of a salt form of these compounds may be obtained as illustrated in Reaction Scheme 6. Thus, Cbz-protected compound of structure (4) may be subjected to hydrogenation on Pd/C in IPA. The reaction mixture may be filtered through a Celite. To the IPA solution may be added a particular acid, for example, L-(+)-tartaric acid (11). After thorough mixing these ingredients (for example, by stirring at 40° C. for 30 min), IPA may be switched to EtOAc in order to give better solid state characteristics. The solid may be then filtered and washed with EtOAc to give the drug substance such as (1a') with minimal impurities.

Reaction Scheme 6

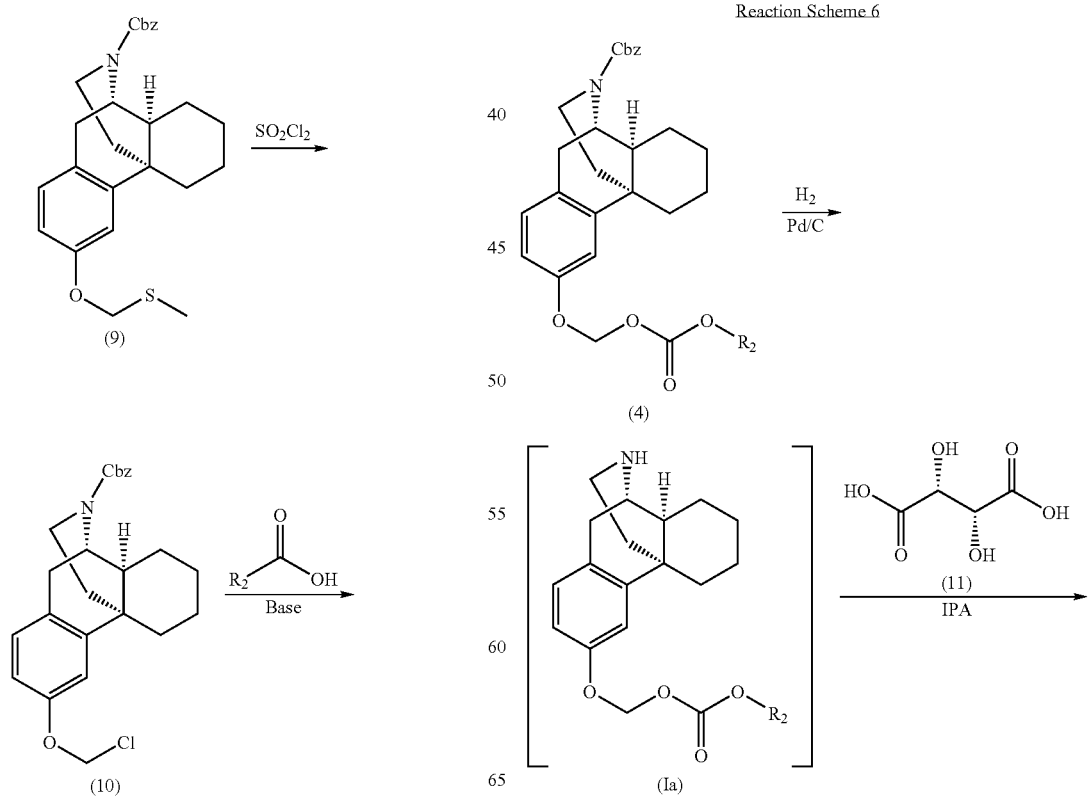

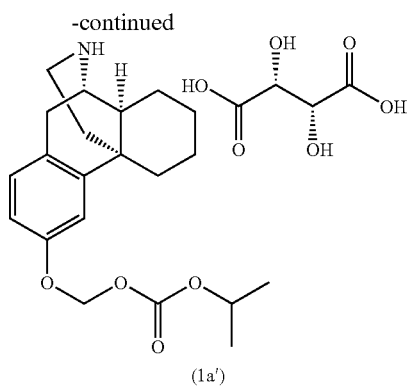

(1a')

Compounds according to Formula (I) may contain a basic functional group and are therefore capable of forming pharmaceutically-acceptable acid addition salts by treatment with a suitable acid. Suitable acids include pharmaceutically-acceptable inorganic acids and pharmaceutically-acceptable organic acids. Representative pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycolate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate.

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as acetone, ethanol, n-propanol, isopropanol, n-butanol, tert-butanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The compound of formula (I) is subjected to the hydrolysis in vivo and, then, converted into its parent compound, i.e., (+)-3-HM which is effective as a neuroprotective agent for Parkinson's disease. Accordingly, the compound of formula (I) is useful in treating or preventing Parkinson's disease.

The pharmaceutical composition may be administered orally, intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg/kg, and preferably from 1 mg to 100 mg/kg of the compound of Formula (1) or its pharmaceutically acceptable salt.

The suitable daily dosage for oral administration is about 0.1 mg/kg to 3 g/kg of the compound of Formula (1) or its pharmaceutically acceptable salt, may be administered 1 to 3 times a day or every two days, depending on the patient's condition.

The present invention is further described and illustrated in Examples provided below, which are, however, not intended to limit the scope of the present invention.

EXAMPLE

Unless otherwise noted, all starting materials were obtained from commercial suppliers and used without further purification.

As used herein, the symbols and conventions used describing the processes, schemes and examples of the present invention are consistent with those used in the contemporary scientific literature, for example, the *Journal of the American Chemical Society* or the *Journal of Biological Chemistry*. The following abbreviations are used in the Examples:

Hz (Hertz)
TLC (thin layer chromatography)
$T_r$ (retention time)
RP (reverse phase)
MeOH (methanol)

i-PrOH (isopropanol)
TFA (trifluoroacetic acid)
TEA (triethylamine)
EtOH (ethanol)
THF (tetrahydrofuran)
DMSO (dimethylsulfoxide)
EtOAc (ethyl acetate)
DCM (dichloromethane)
HOAc (acetic acid)
DMF (N,N-dimethylformamide)
Ac (acetyl)
CDI (1,1-carbonyldiimidazole)
Bn (benzyl)
HOSu (N-hydroxysuccinimide)
HOBT (1-hydroxybenzotriazole)
Boc (tert-butyloxycarbonyl)
mCPBA (meta-chloroperbenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)phosphinic chloride);
EDCI (1-ethyl-3-[3-dimethylaminopropyl]carbodiimide hydrochloride)
HBTU (O-Benzotriazole1-yl-N,N,N',N'-tetramethyluronium hexafluorophosphate)
DBU (1,8-diazabicyclo[5.4.0]undec-7-ene)
IPA (2-propanol)

All references to ether are to diethyl ether; brine refers to a saturated aqueous solution of NaCl. Unless otherwise indicated, all temperatures are expressed in □ (degrees Centigrade). All reactions are conducted under an inert atmosphere at room temperature unless otherwise noted, and all solvents are of the highest available purity unless otherwise indicated.

Microwave reaction was conducted with a Biotage microwave reactor.

$^1$H NMR spectra were recorded on either a Jeol ECX-400, or a Jeol JNM-LA300 spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

Mass spectra were obtained with either a Micromass, Quattro LC Triple Quadrupole Tandem Mass Spectrometer, ESI or Agilent, 6110 Quadrupole LC/MS, ESI.

For preparative HPLC, ca 100 mg of a product was injected in 1 mL of DMSO onto a SunFire™ Prep C18 OBD 5 um 19×100 mm Column with a 10 min gradient from 10% $CH_3CN$ to 90% $CH_3CN$ in $H_2O$. Flash chromatography was carried using Merck silica gel 60 (230-400 mesh). Most of the reactions were monitored by thin-layer chromatography on 0.25 mm E. Merck silica gel plates (60E-254), visualized with UV light using a 5% ethanolic phosphomolybdic acid or p-anisaldehyde solution.

Experiment 1. Permeability Measurement by Performing a Drug Transport Assay with MDCK Monolayers (+)-3-HM was dissolved in DMSO at 10 mM and stored at 4° C. MDCK cells were obtained from the ATCC (American Type Culture Collection, CCL-34). MDCK cells were maintained in DMEM (Dulbecco's MEM with high glucose) containing 1×NEAA (Non-essential amino acids), 10 mM HEPES, 100 units penicillin, 0.1 mg/ml streptomycin and 8% FBS. The cells were cultivated in T-75 flasks in a cell culture incubator at 37° C. MDCK cells were passaged twice per week. When the cells were 90% confluence, the cells were plated at $1\times10^5$ cells/well in transwell. The cells were fed with fresh medium every other day. The Cells were grown to confluence on the transwell for 5 days. When the cells have reached confluence and are differentiated, they are ready to be used for transport studies. The TEER (Transepithelial electrical resistance) of each well was measured by Millicell-ERS system ohm meter. The electrode was immersed in 70% ethanol and PBS for 15 minutes. Then, system was adjusted with a screwdriver at the voltage potentiometer until the meter shows a voltage reading of 0.0 and the electrical resistance for each well was recorded. MDCK monolayers with TEER values >400Ω were used. After the each well was washed by using sterile HBSS (hank's buffered solution) and (+)-3-HM was diluted 100-fold in HBSS, the apical wells were filled with 200 ul of the test compounds. The basolateral wells were filled with 1 ml of HBSS buffer. Only 0.1% DMSO treated wells prepared to adjust for analysis. The cells were incubated at 37° C. for 1 hour. At the end of the transport period, the result samples were removed from the apical (150 ul) and basolateral (900 ul) wells. The representative compounds of Examples were conducted in same conditions.

Experiment 2. The HPLC Analysis and the Calculation of $P_{app}$

HPLC analyses were performed using a WATERS HPLC system. A ZORBAX Eclipse XDB-C18 (4.6×250 mm, 5 μm particle size) was used. The optimal operating conditions are as followed; Mobile phase A is composed of distilled water-acetonitrile (ACN) (9:1, v/v) with 0.1% trifluoroacetic acid (TFA), and mobile phase B is 90% acetonitrile with 0.1% TFA. All buffers were used after the 0.45 μm filtration.

The UV detection was performed at 280 nm or the fluorescence detection was performed at Excitation in 228 nm and Emission in 330 nm.

The concentration of A and B buffer was performed by the gradient method and the total analysis time was 38 min. The optimal operating conditions: elution gradient 0-10 min (10-50%), 10-20 min (50-90%), 20-25 min (90%), 25-27 min (90-10%), 27-38 min (10%). After the analysis of HPLC, the percentage of area of (+)-3-HM and the compound of Example 2 were calculated by remained concentration (μg/ml).

The apparent permeability coefficients ($P_{app}$), expressed in nm/sec, were calculated by the following equation:

Permeability ($P_{app}$)=(Receiver Volume×Receiver Conc.)/(Filter surface area×Reaction Time×donor Conc.)×10$^7$.

When MDCK $P_{app}$ values were plotted against percent human absorption, an approximately sigmoidal relationship was observed (JENNIFER D. IRVINE et al., *Journal of Pharmaceutical Sciences, Vol.* 88, *No.* 1, *January* 1999).

Well-absorbed prodrug compounds showed generally high $P_{app}$ values, and poorly absorbed compounds showed generally low $P_{app}$ values.

Permeability values for known drugs such as, acetaminophen, dexamethasone, and ketoprofen are 350, 200, and 200 nm/s, respectively, and clearly their human absorption values are pretty much high for the good oral bio-availability at 94, 98, and 100%, respectively.

The results are shown in Table 1. Table 1 demonstrates that permeability values of all the tested compounds are improved by 2-fold or more as compared with the parent molecule, (+)-3-HM. As permeability values of all the tested compounds are higher than 100 nm/s except for the compounds of Examples 56 and 58, they are expected to have excellent oral bio-availabilities.

TABLE 1

The apparent permeability coefficients ($P_{app}$) of (+)-3-HM and the compounds of the present invention.

| Example No. | $P_{app}$ (nm/sec) |
|---|---|
| HM | 33.3 |
| 80 | 185.7 |
| 105 | 202.9 |
| 15 | 337.0 |
| 54 | 288.7 |
| 58 | 60.5 |
| 17 | 227.3 |
| 60 | 202.3 |
| 56 | 94.3 |
| 66 | 162.5 |
| 70 | 166.1 |
| 72 | 131.3 |
| 23 | 203.4 |
| 25 | 203.1 |
| 27 | 234.3 |
| 68 | 101.2 |
| 31 | 223.1 |
| 37 | 135.5 |
| 41 | 230.6 |
| 2 | 262 |
| 44 | 212 |
| 6 | 206 |
| 4 | 153 |
| 9 | 487 |
| 3 | 219 |
| 8 | 197 |

Experiment 3. Pharmacokinetics Study

Male Sprague-Dawley rats (200~230 g) were purchased from Charles River Laboratory. Animals were housed under standard conditions of temperature, humidity and light. Food and water were provided ad libitum. The day before administration, a jugular vein cannular was implanted under anesthesia with 1 mL/kg solution of ketamine:xylazine (90:10, v/v) by intraperitoneal injection for blood collection. Oral administration at a dose of 60 mg/10 ml/kg by oral gavages and/or intravenous administration at a dose of 10 mg/1 ml/kg were delivered. Blood (~0.3 ml/sample) were collected into heparinized tubes at various time intervals after oral and/or intravenous administration of present invented compounds, and were centrifuged. Each plasma samples (~0.2 ml) were immediately frozen at until analysis. The concentrations of parent molecule (+)-3-HM in plasma after the administration of (+)-3-HM or the compound of Example 2 were determined by HPLC (Waters 2487). The results are summarized in Tables 2.1 and 2.2. The maximum plasma concentration ($C_{max}$), the time to reach peak plasma concentration ($T_{max}$), terminal half-time ($t_{1/2}$) and the area under the plasma concentration-time curve from zero to time infinity ($AUC_{0-\infty}$) are the primary parameters. Overall, oral bioavailability of the compound of Example 2 (92.4%) is significantly higher than HM (17.85%) at the same dose. These results indicate that the compound of Example 2 has a favorable pharmacokinetic profile as a prodrug. Such pharmacokinetic profiles show that oral availability of the compound of Example 2 has been improved by 4-fold or more (Table 2.2).

TABLE 2.1

Pharmacokinetic parameters of HM and the compound of Example 2 with i.v. injection experiments. Plasma concentration of (+)-3-HM were measured after (+)-3-HM or the compound of Example 2 is intravenously administered in rats.

| Parameters | HM (10 mg/kg, i.v.) | The compound of Example 2 (10 mg/kg, i.v.) (+)-3-HM |
|---|---|---|
| $T_{1/2}$ (hr) | 2.55 | 1.57 |
| CL (ml/hr/kg) | 1.02 | 3.34 |
| AUC last (hr × µg/ml) | 3.15 | 2.70 |
| MRT (hr) | 3.33 | 1.73 |

CL: Clearance (with units of flow per weights; mL/hr/kg) is the volume of blood or plasma that must be cleared of drug in unit time per unit weight of individual.
MRT: Mean Residence time is the arithmetic mean of the duration that each drug molecule resides in the body (MRT = AUMC/AUC).

TABLE 2.2

Pharmacokinetic parameters of HM and the compound of Example 2 with oral administration experiments. Plasma concentration of HM were measured after (+)-3-HM and the compound of Example 2 are delivered orally in rats.

| Parameters | HM (60 mg/kg, p.o.) | The compound of Example 2 (60 mg/kg, p.o.) (+)-3-HM |
|---|---|---|
| $T_{max}$ (hr) | 0.33 | 2.00 |
| $C_{max}$ (µg/kg) | 0.59 | 2.38 |
| AUC last (hr × µg/ml) | 3.38 | 14.89 |
| $T_{1/2}$ (hr) | 3.14 | 5.41 |

Experiment 4. In Vivo Efficacy Measurement of (+)-3-HM and the Compound of Example 2.

Figure 2:
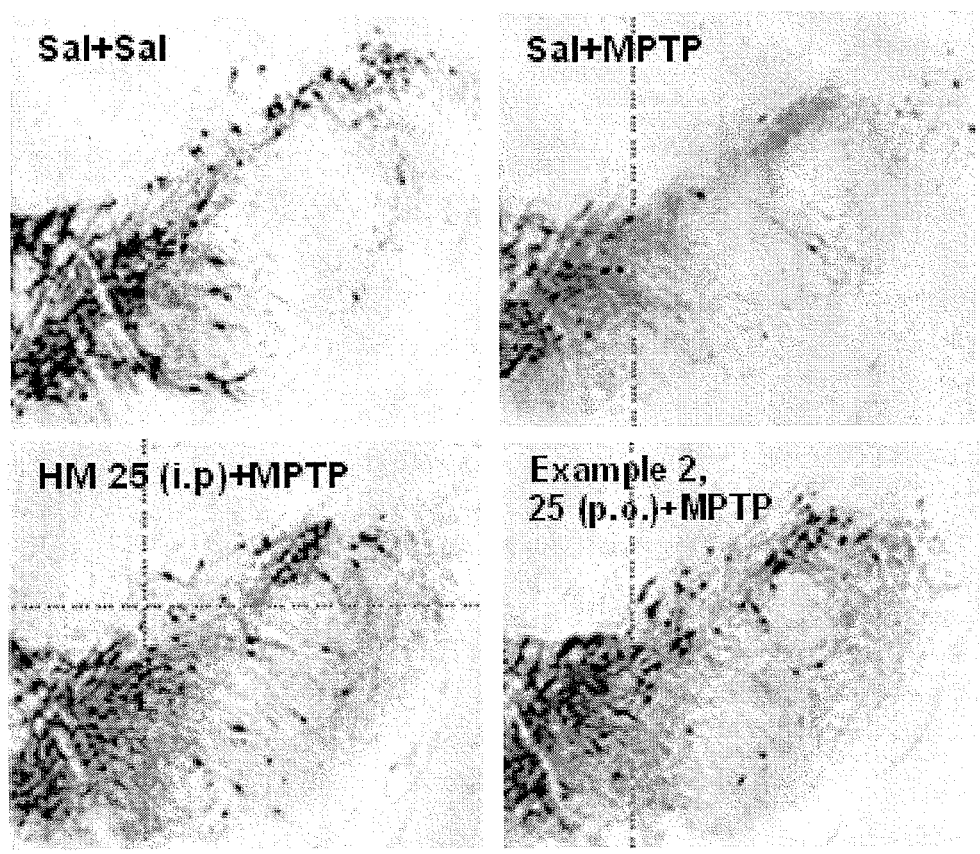
FIG. 2 illustrates the effects of (+)-3-HM intraperitoneal injected and the compound of Example 2 orally administered on MPTP-induced Parkinson's disease animal model.

To examine the effect of (+)-3-HM and the compound of Example 2 on MPTP-induced Parkinson's animal model, C57BL6/J received daily MPTP injection for 7 days. (+)-3-HM (25 mg/kg, i.p.) and the compound of Example 2 (25 mg/kg, p.o.) administered 30 min before MPTP injection for the last 3 days and animals were sacrificed 3 days after the last MPTP injection. Brains were cut on a microtome and SNpc TH-immunoreactivity was performed by ABC methods. These results shown in FIG. 2 as TH-immunoreactive neurons throughout SNpc demonstrate that oral administration of the compound of Example 2 has more protection against MPTP-induced loss of dopamine neuron than intraperitoneal injection of HM at same dose.

Example 1

(+)-[N-(Benzyloxycarbonyl)morphinan-3-yloxy] methyl isopropyl carbonate

Step 1:
(+)-3-Hydroxy-N-(benzyloxycarbonyl)morphinan

To (+)-3-hydroxymorphinan (HM) hydrobromide (50.0 g, 154.2 mmol), sodium hydroxide (12.3 g, 308.4 mmol) in a mixture of 1,4-dioxane (200 mL) and water (200 mL) was added Cbz-Cl (24.2 mL, 169.6 mmol) dropwise at room temperature. The reaction mixture was stirred vigorously at room temperature overnight. After the reaction was completed, water (200 mL) was added. The mixture was extracted with diethyl ether (500 mL×2). The combined organics were dried over MgSO₄, filtered, and evaporated under vacuum. Standing under high vacuum provided the title compound (57.7 g, 99%) as a light yellow solid. The compound was used for the next step without further purification.

¹H NMR (400 MHz, CDCl₃) δ 7.39-7.31 (m, 5H), 6.70-6.91 (m, 1H), 6.77 (d, J=2.4 Hz, 1H), 6.65-6.61 (m, 1H), 5.18-5.13 (m, 2H), 4.36 (br d, J=42.0 Hz, 1H), 3.94-3.83 (m, 1H), 3.12-3.03 (m, 1H), 2.72-2.57 (m, 2H), 2.32 (d, J=11.2 Hz, 1H), 1.71-1.24 (m, 9H), 1.11-1.02 (m, 1H).

MH+ 378.

Step 2: (+)[N-(Benzyloxycarbonyl)morphinan-3-yloxy]methyl isopropyl carbonate

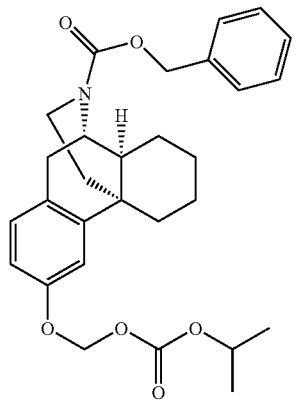

To (+)-3-hydroxy-N-(benzyloxycarbonyl)morphinan (33.0 g, 87.4 mmol) and cesium carbonate (28.5 g, 87.4 mmol) in acetone (450 mL) was added iodomethyl isopropyl carbonate (21.3 g, 87.4 mmol) (see Rigel Pharmaceuticals, Inc. US2006/247287 A1, Appl.; US2006-381215 (2006 May 2)) at room temperature. The reaction mixture was stirred vigorously at room temperature overnight. The acetone was then removed by rotary evaporation under vacuum. To the residue was added saturated NaHCO₃ solution. The mixture was extracted with EtOAc (300 mL×2). The combined organics were washed with 1N HCl solution (300 mL), dried over MgSO₄, filtered, and evaporated under vacuum to provide the title compound (42.0 g, 97%) as a yellow gum.

$[\alpha]_D^{27}$+112.0° (c=1.0, MeOH); IR (KBr) $\nu_{max}$ 2931, 1754, 1695, 1496, 1422, 1270, 1234, 1218, 1185, 1044 cm⁻¹; ¹H NMR (400 MHz, CDCl₃) δ 7.39-7.32 (m, 5H), 7.03 (t, J=8.4 Hz, 1H), 6.96 (s, 1H), 6.88 (dd, J=8.4, 2.4 Hz, 1H), 5.75 and 5.70 (AB q, J=6.8 Hz, 2H), 5.21-5.09 (m, 2H), 4.93 (m, 1H), 4.37 (br d, J=43.2 Hz, 1H), 3.96-3.84 (m, 1H), 3.17-3.05 (m, 1H), 2.76-2.56 (m, 2H), 2.34 (d, J=10.8 Hz, 1H), 1.72-1.43 (m, 6H), 1.43-1.26 (m, 9H), 1.08-0.99 (m, 1H); ¹³C NMR (400 MHz, CDCl₃) δ 155.8, 155.4, 153.7, 140.8, 136.9, 130.9, 130.7, 129.3, 129.2, 128.4, 127.9, 127.8, 114.0, 113.4, 88.6, 72.9, 66.9, 49.8, 43.7, 41.5, 38.3, 37.6, 36.4, 31.3, 26.4, 26.3, 22.3, 22.0, 21.7.

MH+ 494.

Example 2

(+)-Isopropyl(morphinan-3-yloxy)methyl carbonate

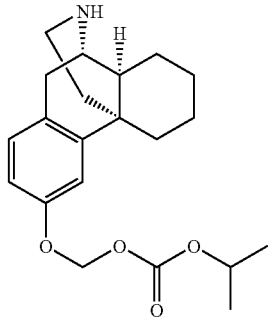

(+)-Isopropyl[N-(benzyloxycarbonyl)morphinan-3-yloxy]methyl carbonate (42.0 g, 84.1 mmol) from Example 1 was subjected to hydrogenation (balloon) on 10% Pd/C (6.3 g) in EtOH (250 mL) at room temperature. After the reaction was completed, the reaction mixture was filtered through a Celite, and washed with EtOH (400 mL). The combined EtOH solution was evaporated under vacuum. The residue was further purified by prep reverse-phase HPLC to provide the title compound (5.82 g, 19%) as a yellow solid.

$[\alpha]_D^{27}$+27.9° (c=1.0, MeOH); IR (KBr) $\nu_{max}$ 2980, 2929, 2856, 1753, 1610, 1496, 1271, 1218, 1112, 1045 cm⁻¹; ¹H NMR (400 MHz, CDCl₃) δ 7.06 (d, J=8.4 Hz, 1H), 6.94 (d, J=2.6 Hz, 1H), 6.87 (dd, J=8.4, 2.6 Hz, 1H), 5.77 and 5.71 (AB q, J=6.4 Hz, 2H), 4.93 (m, 1H), 3.16-3.05 (m, 2H), 2.94-2.54 (m, 4H), 2.29 (d, J=11.9 Hz, 1H), 1.78-1.74 (m, 1H), 1.66-1.50 (m, 3H), 1.41-1.20 (m, 10H), 1.07-0.99 (m, 1H); ¹³C NMR (400 MHz, CDCl₃) δ 155.6, 153.7, 141.8, 132.2, 128.8, 113.9, 113.1, 88.7, 72.6, 65.9, 50.9, 46.8, 42.2, 38.9, 38.2, 36.8, 33.1, 26.7, 26.6, 22.0, 21.7.

MH+ 360.

The following compounds of Examples 3 to 42 were obtained by repeating the procedure of Example 1 and Example 2.

Example 3

(+)-(Morphinan-3-yloxy)methyl propyl carbonate

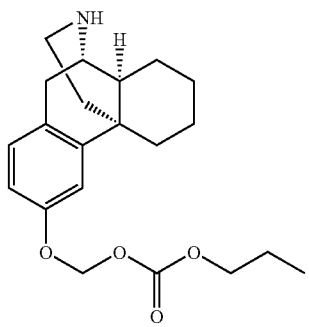

¹H NMR (400 MHz, CDCl₃) δ 7.05 (d, J=8.4 Hz, 1H), 6.94 (d, J=2.0 Hz, 1H), 6.88 (dd, J=8.4, 2.4 Hz, 1H), 5.77 and 5.72 (AB q, J=6.4 Hz, 2H), 4.14 (t, 6.6 Hz, 2H), 3.14-3.04 (m, 2H), 2.84-2.57 (m, 4H), 2.36-2.22 (m, 2H), 1.82-1.61 (m, 5H), 1.51-1.49 (m, 2H), 1.40-1.30 (m, 2H), 1.05-0.90 (m, 4H).

MH+ 360.

Example 4

(+)-Cyclopropylmethyl(morphinan-3-yloxy)methyl carbonate

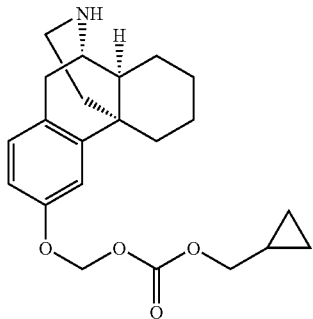

¹H NMR (400 MHz, CDCl₃) δ 7.05 (d, J=8.4 Hz, 1H), 6.94 (d, J=2.4 Hz, 1H), 6.83 (dd, J=8.4, 2.4 Hz, 1H), 5.78 and 5.73 (AB q, J=6.4 Hz, 2H), 4.01 (d, J=9.2 Hz, 2H), 3.16-3.08 (m, 2H), 2.80-2.54 (m, 4H), 2.28 (d, J=13.2 Hz, 1H), 1.81-1.76 (m, 1H), 1.66-1.50 (m, 3H), 1.42-1.26 (m, 4H), 1.20-1.10 (m, 1H), 1.09-1.00 (m, 1H), 0.60 (m, 2H), 0.32 (m, 2H).

MH+ 372.

Example 5

(+)-[N-(Benzyloxycarbonyl)morphinan-3-yloxy] methyl cyclopentyl carbonate

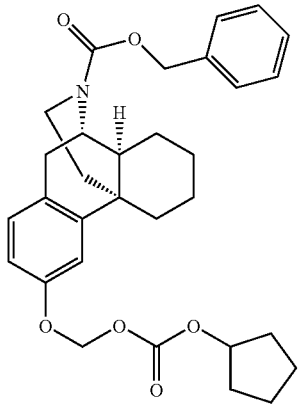

¹H NMR (300 MHz, CDCl₃) δ 7.39-7.32 (m, 5H), 7.03 (t, J=8.4 Hz, 1H), 6.96 (s, 1H), 6.88 (dd, J=8.4, 2.4 Hz, 1H), 5.75 and 5.70 (AB q, J=6.4 Hz, 2H), 5.16-5.05 (m, 3H), 4.37 (br d, J=43.2 Hz, 1H), 3.96-3.84 (m, 1H), 3.17-3.05 (m, 1H), 2.76-2.56 (m, 2H), 2.32 (d, J=10.8 Hz, 1H), 1.98-1.51 (m, 13H), 1.50-1.25 (m, 4H), 1.08-0.99 (m, 1H).

MH+ 520.

Example 6

(+)-Cyclopentyl(morphinan-3-yloxy)methyl carbonate

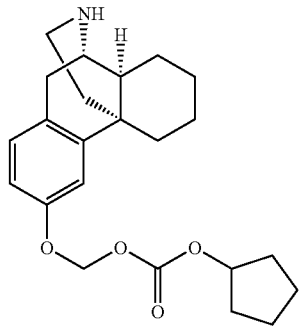

¹H NMR (400 MHz, CDCl₃) δ 7.05 (d, J=8.4 Hz, 1H), 6.94 (d, J=2.4 Hz, 1H), 6.83 (dd, J=8.4, 2.4 Hz, 1H), 5.76 and 5.71 (AB q, J=6.4 Hz, 2H), 5.15-5.09 (m, 1H), 3.14-3.09 (m, 2H), 2.81-2.60 (m, 4H), 2.30-2.27 (m, 1H), 1.89-1.49 (m, 11H), 1.49-1.26 (m, 5H), 1.09-1.01 (m, 1H).

MH+ 386.

Example 7

(+)-[N-(Benzyloxycarbonyl)morphinan-3-yloxy] methyl cyclohexyl carbonate

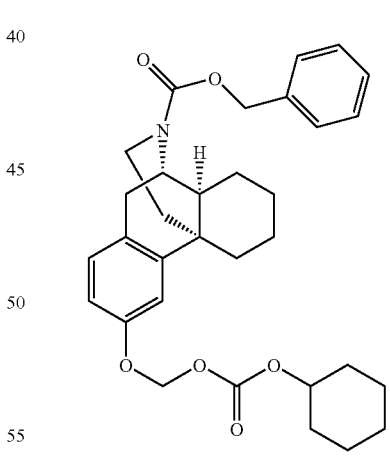

¹H NMR (400 MHz, CDCl₃) δ 7.39-7.32 (m, 5H), 7.03 (t, J=8.4 Hz, 1H), 6.96 (s, 1H), 6.88 (dd, J=8.4, 2.4 Hz, 1H), 5.77 and 5.72 (AB q, J=6.4 Hz, 2H), 5.18-5.13 (m, 2H), 4.70-4.63 (m, 1H), 4.37 (br d, J=43.2 Hz, 1H), 3.96-3.84 (m, 1H), 3.15-3.05 (m, 1H), 2.76-2.56 (m, 2H), 2.34 (d, J=10.8 Hz, 1H), 1.94-1.91 (m, 2H), 1.77-1.37 (m, 10H), 1.35-1.20 (m, 7H), 1.09-0.99 (m, 1H).

MH+ 534.

Example 8

(+)-Cyclohexyl(morphinan-3-yloxy)methyl carbonate

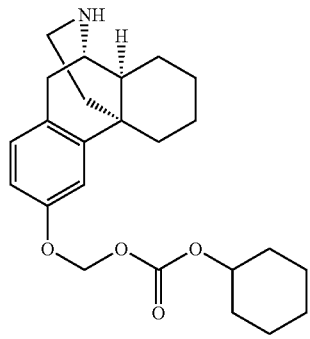

$^1$H NMR (400 MHz, CDCl$_3$) δ 7.05 (d, J=8.4 Hz, 1H), 6.94 (d, J=2.4 Hz, 1H), 6.83 (dd, J=8.4, 2.4 Hz, 1H), 5.77 and 5.72 (AB q, J=6.4 Hz, 2H), 4.70-4.64 (m, 1H), 3.16-3.10 (m, 2H), 2.81-2.58 (m, 4H), 2.30-2.28 (m, 1H), 1.92-1.24 (m, 18H), 1.09-1.01 (m, 1H).

MH+ 400.

Example 9

(+)-Cyclohexylmethyl(morphinan-3-yloxy)methyl carbonate

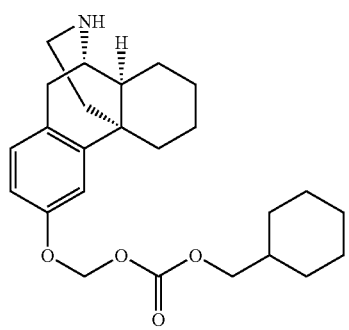

$^1$H NMR (400 MHz, CDCl$_3$) δ 7.05 (d, J=8.4 Hz, 1H), 6.94 (d, J=2.4 Hz, 1H), 6.83 (dd, J=8.4, 2.4 Hz, 1H), 5.76 and 5.72 (AB q, J=6.4 Hz, 2H), 3.99 (d, J=6.4 Hz), 3.16-3.08 (m, 2H), 2.80-2.54 (m, 4H), 2.30 (d, J=12.8 Hz, 1H), 1.75-1.64 (m, 8H), 1.51-1.13 (m, 9H), 1.11-0.93 (m, 3H).

MH+ 414.

Example 10

(+)-Heptan-4-yl(morphinan-3-yloxy)methyl carbonate

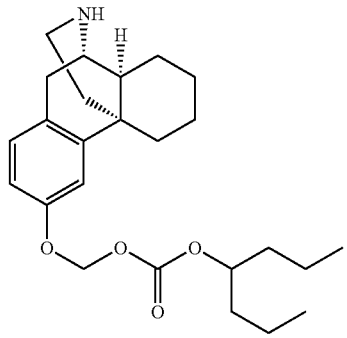

$^1$H NMR (400 MHz, CDCl$_3$) δ 7.05 (d, J=8.4 Hz, 1H), 6.94 (d, J=2.8 Hz, 1H), 6.86 (dd, J=8.4, 2.8 Hz, 1H), 5.75 and 5.72 (AB q, J=7.6 Hz, 2H), 4.80-4.76 (m, 1H), 3.16-3.04 (m, 2H), 2.78-2.52 (m, 4H), 2.28 (d, J=12.0 Hz, 1H), 1.82-1.72 (m, 1H), 1.70-1.46 (m, 8H), 1.44-1.24 (m, 7H), 1.12-0.98 (m, 2H), 0.91 (t, J=7.2 Hz, 6H).

MH+ 416.

Example 11

(+)-Decahydronaphthalen-2-yl(morphinan-3-yloxy) methyl carbonate

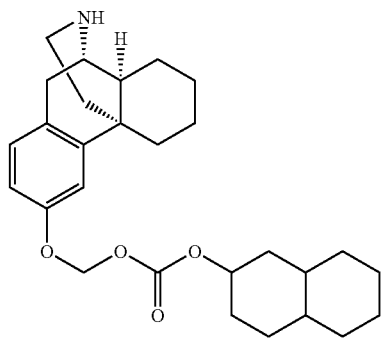

$^1$H NMR (300 MHz, CDCl$_3$) δ 7.04 (d, J=8.4 Hz, 1H), 6.93 (s, 1H), 6.86 (d, J=8.4 Hz, 1H), 5.76-5.69 (m, 2H), 4.65-4.61 (m, 1H), 3.19-3.07 (m, 2H), 2.76-2.65 (m, 4H), 2.28 (d, J=12.9 Hz, 1H), 1.75-1.64 (m, 8H), 1.51-1.13 (m, 15H), 1.11-0.93 (m, 2H).

MH+ 454.

Example 12

(+)-[N-(Benzyloxycarbonyl)morphinan-3-yloxy]methyl decahydronaphthalen-1-yl carbonate

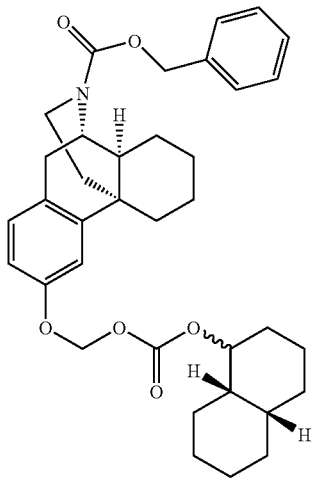

$^1$H NMR (300 MHz, CDCl$_3$) δ 7.36-7.32 (m, 5H), 7.07-6.98 (m, 1H), 6.95 (s, 1H), 6.87 (dd, J=8.3 Hz, 2.4 Hz, 1H), 5.73-5.71 (m, 2H), 5.15-5.12 (m, 2H), 4.71 (m, 1H), 4.40-4.30 (d, J=29.4 Hz, 1H), 3.92-3.82 (m, 1H), 3.11-3.03 (m, 1H), 2.72-2.56 (m, 2H), 2.31-2.28 (m, 1H), 2.18-2.01 (m, 1H), 1.98-1.26 (m, 24H), 1.11-1.00 (m, 1H).

MH+ 588.

Example 13

(+)-Decahydronaphthalen-1-yl(morphinan-3-yloxy)methyl carbonate

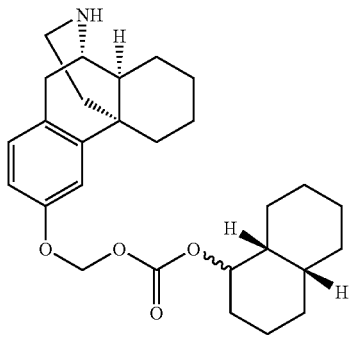

$^1$H NMR (300 MHz, CDCl$_3$) δ 7.05 (d, J=8.4 Hz, 1H), 6.93 (d, J=2.7 Hz, 1H), 6.87 (dd, J=8.4, 2.7 Hz, 1H), 5.77-5.70 (m, 2H), 4.71-4.68 (m, 1H), 3.09-3.08 (m, 2H), 2.77-2.59 (m, 4H), 2.01-2.17 (m, 1H), 1.82-1.64 (m, 8H), 1.64-1.18 (m, 15H), 1.11-0.93 (m, 2H).

MH+ 454.

Example 14

(+)-[N-(Benzyloxycarbonyl)morphinan-3-yloxy]methyl cyclopentylmethyl carbonate

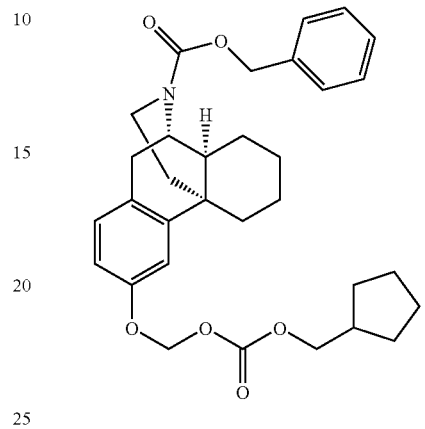

$^1$H NMR (400 MHz, CDCl$_3$) δ 7.40-7.30 (m, 5H), 7.03-6.99 (m, 1H), 6.96 (d, J=2.4 Hz, 1H), 6.87 (dd, J=8.4, 2.4 Hz, 1H), 5.73 (m, 2H), 5.16-5.11 (m, 2H), 4.41-4.31 (m, 1H), 4.06 (d, J=7.2 Hz, 2H), 3.98-3.82 (m, 1H), 3.16-3.03 (m, 1H), 2.71-2.58 (m, 2H), 2.38-2.31 (m, 1H), 2.27-2.20 (m, 1H), 1.80-1.42 (m, 11H), 1.38-1.21 (m, 6H), 1.05-0.98 (m, 1H).

MH+ 534.

Example 15

(+)-Cyclopentylmethyl(morphinan-3-yloxy)methyl carbonate TFA

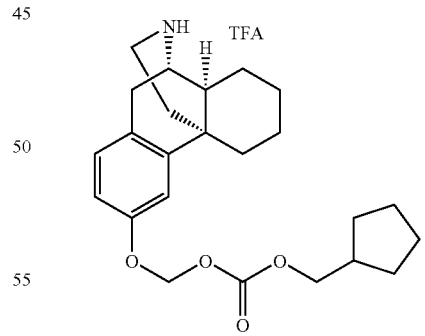

$^1$H NMR (400 MHz, CDCl$_3$) δ9.08 (br s, 1H), 7.12 (d, J=8.4 Hz, 1H), 6.96-6.92 (m, 2H), 5.76 and 5.71 (AB q, J=6.8 Hz, 2H), 4.06 (d, J=7.2 Hz, 2H), 3.68 (m, 1H), 3.22-3.09 (m, 3H), 2.85-2.70 (m, 1H), 2.39-2.30 (m, 1H), 2.28-2.21 (m, 1H), 2.11-2.05 (m, 1H), 1.96-1.89 (m, 1H), 1.79-1.39 (m, 12H), 1.30-1.20 (m, 3H), 1.07-0.98 (m, 1H).

MH+ 400.

Example 16

(+)-[-N-(Benzyloxycarbonyl)morphinan-3-yloxy]
methyl cyclobutylmethyl carbonate

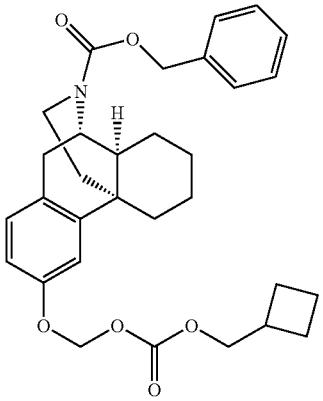

¹H NMR (400 MHz, CDCl₃) δ 7.40-7.28 (m, 5H), 7.03-6.99 (m, 1H), 6.95 (d, J=2.8 Hz, 1H), 6.87 (dd, J=8.4, 2.4 Hz, 1H), 5.75 and 5.71 (AB q, J=6.4 Hz, 2H), 5.18-5.08 (m, 2H), 4.44-4.28 (m, 1H), 4.14 (d, J=6.8 Hz, 2H), 3.88-3.81 (m, 1H), 3.15-3.03 (m, 1H), 2.72-2.58 (m, 2H), 2.37-2.29 (m, 1H), 2.10-2.02 (m, 2H), 1.93-1.76 (m, 4H), 1.74-1.42 (m, 6H), 1.38-1.20 (m, 4H), 1.05-0.98 (m, 1H).

MH+ 520.

Example 17

(+)-Cyclobutylmethyl(morphinan-3-yloxy)methyl
carbonate TFA

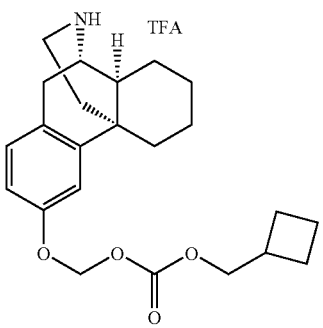

¹H NMR (400 MHz, CDCl₃) δ 9.00 (br s, 1H), 7.12 (d, J=8.0 Hz, 1H), 6.95-6.92 (m, 2H), 5.76 and 5.71 (AB q, J=6.8 Hz, 2H), 4.15 (d, J=6.8 Hz, 2H), 3.70 (m, 1H), 3.23-3.09 (m, 3H), 2.82-2.61 (m, 2H), 2.37-2.32 (m, 1H), 2.12-2.02 (m, 3H), 1.97-1.76 (m, 5H), 1.68-1.62 (m, 1H), 1.57-1.34 (m, 5H), 1.31-1.20 (m, 1H), 1.09-1.01 (m, 1H).

MH+ 386.

Example 18

(+)-[N-(Benzyloxycarbonyl)morphinan-3-yloxy]
methyl 2-ethylhexyl carbonate

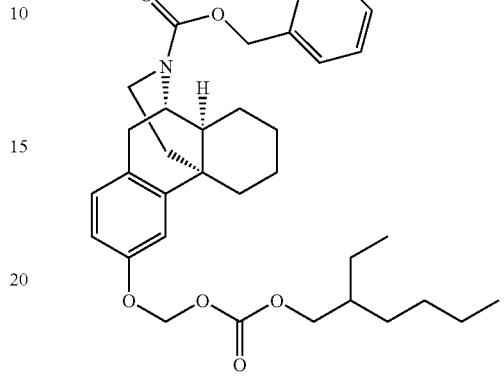

¹H NMR (400 MHz, CDCl₃) δ 7.40-7.29 (m, 5H), 7.02 (d, J=8.0 Hz, 1H), 6.95 (d, J=2.0 Hz, 1H), 6.87 (dd, J=8.4, 2.4 Hz, 1H), 5.75 and 5.71 (AB q, J=6.4 Hz, 2H), 5.18-5.07 (m, 2H), 4.44-4.28 (m, 1H), 4.13-4.05 (m, 2H), 3.98-84 (m, 1H), 3.14-3.03 (m, 1H), 2.74-2.56 (m, 2H), 2.35-2.31 (m, 1H), 1.71-1.41 (m, 7H), 1.39-1.21 (m, 11H), 1.07-0.98 (m, 1H), 0.89-0.85 (m, 6H).

MH+ 564.

Example 19

(+)-2-Ethylhexyl(morphinan-3-yloxy)methyl
carbonate TFA

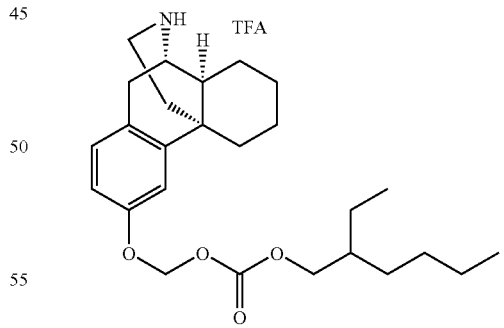

¹H NMR (400 MHz, CDCl₃) δ 9.03 (br s, 1H), 7.12 (d, J=8.0 Hz, 1H), 6.99-6.92 (m, 2H), 5.76 and 5.71 (AB q, J=6.8 Hz, 2H), 4.13-4.05 (m, 2H), 3.71 (m, 1H), 3.24-3.11 (m, 3H), 2.76 (m, 1H), 2.35 (d, J=14.0 Hz, 1H), 2.08 (d, J=12.4 Hz, 1H), 2.00-1.92 (m, 1H), 1.68-1.26 (m, 16H), 1.09-1.00 (m, 1H), 0.89-0.84 (m, 6H).

MH+ 430.

Example 20

(+)-[N-(Benzyloxycarbonyl)morphinan-3-yloxy] methyl butyl carbonate

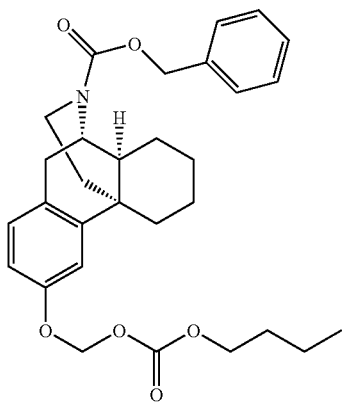

¹H NMR (400 MHz, CDCl₃) δ 7.40-7.28 (m, 5H), 7.04-6.98 (m, 1H), 6.95 (d, J=2.0 Hz, 1H), 6.87 (dd, J=8.4, 2.4 Hz, 1H), 5.75 and 5.71 (AB q, J=6.4 Hz, 2H), 5.18-5.08 (m, 2H), 4.41-4.28 (m, 1H), 4.17 (t, J=6.4 Hz, 2H), 3.96-3.76 (m, 1H), 3.15-3.03 (m, 1H), 2.72-2.55 (m, 2H), 2.35-2.30 (m, 1H), 1.72-1.44 (m, 7H), 1.41-1.19 (m, 6H), 1.08-0.96 (m, 1H), 0.92 (t, J=7.2 Hz, 3H).

MH+ 508.

Example 21

(+)-Butyl(morphinan-3-yloxy)methyl carbonate TFA

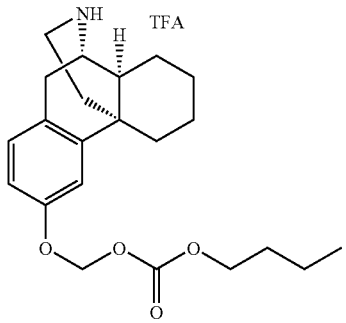

¹H NMR (400 MHz, CDCl₃) δ 8.84 (br s, 1H), 7.12 (d, J=8.4 Hz, 1H), 6.99-6.93 (m, 2H), 5.76 and 5.71 (AB q, J=6.4 Hz, 2H), 4.19 (t, J=6.4 Hz, 2H), 3.76 (m, 1H), 3.24-3.08 (m, 3H), 2.77 (m, 1H), 2.35 (d, J=13.6 Hz, 1H), 2.06 (d, J=12.0 Hz, 1H), 1.96-1.90 (m, 1H), 1.69-1.51 (m, 3H), 1.49-1.34 (m, 7H), 1.26-1.20 (m, 1H), 1.10-1.00 (m, 1H), 0.92 (t, J=7.2 Hz, 3H).

MH+ 374.

Example 22

(+)-[N-(Benzyloxycarbonyl)morphinan-3-yloxy] methyl isobutyl carbonate

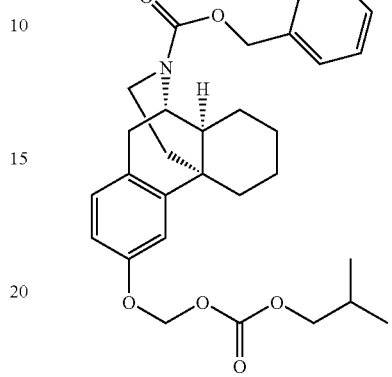

¹H NMR (400 MHz, CDCl₃) δ 7.39-7.29 (m, 5H), 7.08-6.98 (m, 1H), 6.96 (s, 1H), 6.87 (dd, J=8.4, 2.4 Hz, 1H), 5.75 and 5.72 (AB q, J=6.4 Hz, 2H), 5.16-5.11 (m, 2H), 4.41-4.31 (m, 1H), 3.95 (d, J=6.4 Hz, 2H), 3.86-3.77 (m, 1H), 3.13-3.03 (m, 1H), 2.75-2.55 (m, 2H), 2.36-2.30 (m, 1H), 2.04-1.92 (m, 1H), 1.72-1.45 (m, 5H), 1.39-1.21 (m, 4H), 1.10-0.99 (m, 1H), 0.93 (d, J=6.8 Hz, 6H).

MH+ 508.

Example 23

(+)-Isobutyl(morphinan-3-yloxy)methyl carbonate TFA

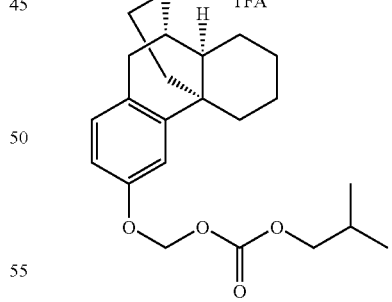

¹H NMR (400 MHz, CDCl₃) δ 9.03 (br s, 1H), 7.12 (d, J=8.4 Hz, 1H), 6.99-6.93 (m, 2H), 5.76 and 5.72 (AB q, J=6.8 Hz, 2H), 3.96 (d, J=6.4 Hz, 2H), 3.71 (m, 1H), 3.24-3.10 (m, 3H), 2.76 (m, 1H), 2.35 (d, J=13.6 Hz, 1H), 2.08 (d, J=13.2 Hz, 1H), 2.04-1.90 (m, 1H), 1.68-1.65 (m, 1H), 1.58-1.36 (m, 6H), 1.29-1.23 (m, 1H), 1.09-1.03 (m, 1H), 0.93 (d, J=7.2 Hz, 6H).

MH+ 374.

Example 24

(+)-[N-(Benzyloxycarbonyl)morphinan-3-yloxy]methyl sec-butyl carbonate

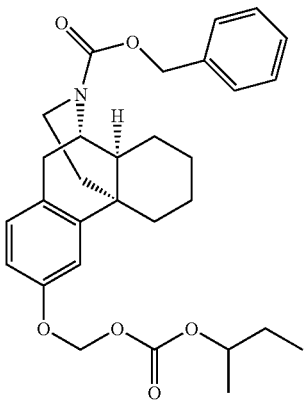

$^1$H NMR (400 MHz, CDCl$_3$) δ 7.38-7.27 (m, 5H), 7.02 (t, J=8.4 Hz, 1H), 6.95 (s, 1H), 6.87 (dd, J=8.4, 2.4 Hz, 1H), 5.75 and 5.71 (AB q, J=6.8 Hz, 2H), 5.14-5.08 (m, 1H), 4.79-4.71 (m, 1H), 4.41-4.30 (m, 1H), 3.93-3.72 (m, 1H), 3.14-3.04 (m, 1H), 2.72-2.55 (m, 2H), 2.36-2.30 (m, 1H), 1.74-1.44 (m, 8H), 1.40-1.28 (m, 4H), 1.27 (d, J=6.4 Hz, 3H), 1.08-0.95 (m, 1H), 0.91 (t, J=7.6 Hz, 3H).

MH+ 508.

Example 25

(+)-sec-Butyl(morphinan-3-yloxy)methyl carbonate TFA

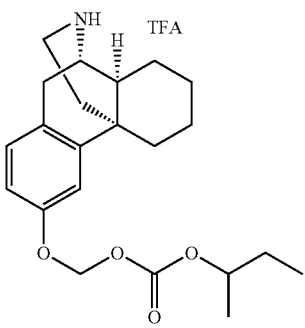

$^1$H NMR (400 MHz, CDCl$_3$) δ 8.83 (br s, 1H), 7.12 (d, J=8.0 Hz, 1H), 6.99-6.93 (m, 2H), 5.76 and 5.71 (AB q, J=6.4 Hz, 2H), 4.75 (m, 1H), 3.71 (m, 1H), 3.24-3.08 (m, 3H), 2.78 (m, 1H), 2.35 (d, J=14.0 Hz, 1H), 2.06 (d, J=12.0 Hz, 1H), 1.96-1.90 (m, 1H), 1.70-1.33 (m, 8H), 1.27 (d, J=6.4 Hz, 3H), 1.25-1.23 (m, 1H), 1.10-0.96 (m, 1H), 0.91 (t, J=7.2 Hz, 3H).

MH+ 374.

Example 26

(+)[N-(Benzyloxycarbonyl)morphinan-3-yloxy]methyl cycloheptyl carbonate

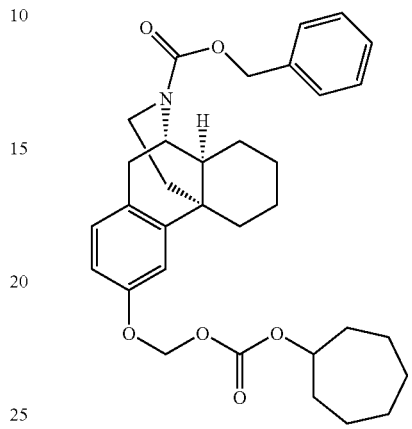

$^1$H NMR (400 MHz, CDCl$_3$) δ 7.38-7.28 (m, 5H), 7.02 (t, J=8.8 Hz, 1H), 6.95 (s, 1H), 6.87 (dd, J=8.4, 2.4 Hz, 1H), 5.74 and 5.70 (AB q, J=6.8 Hz, 2H), 5.20-5.11 (m, 2H), 4.86-4.80 (m, 1H), 4.41-4.30 (m, 1H), 3.95-3.82 (m, 1H), 3.13-3.03 (m, 1H), 2.71-2.58 (m, 2H), 2.35-2.31 (m, 1H), 2.00-1.92 (m, 2H), 1.76-1.60 (m, 6H), 1.57-1.34 (m, 9H), 1.32-1.21 (m, 4H), 1.07-1.01 (m, 1H).

MH+ 548.

Example 27

(+)-Cycloheptyl(morphinan-3-yloxy)methyl carbonate TFA

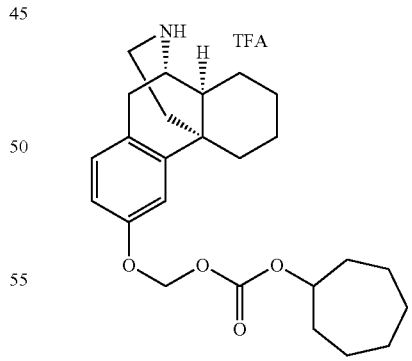

$^1$H NMR (400 MHz, CDCl$_3$) δ 9.30 (br s, 1H), 7.12 (d, J=8.4 Hz, 1H), 6.96-6.93 (m, 2H), 5.76 and 5.71 (AB q, J=6.8 Hz, 2H), 4.88-4.81 (m, 1H), 3.62 (m, 1H), 3.17-3.06 (m, 3H), 2.85-2.72 (m, 2H), 2.35 (d, J=13.6 Hz, 1H), 2.08 (d, J=12.0 Hz, 1H), 2.01-1.88 (m, 3H), 1.77-1.65 (m, 5H), 1.58-1.36 (m, 10H), 1.35-1.21 (m, 1H), 1.07-1.03 (m, 1H).

MH+ 414.

Example 28

(+)-[N-(Benzyloxycarbonyl)morphinan-3-yloxy]methyl phenethyl carbonate

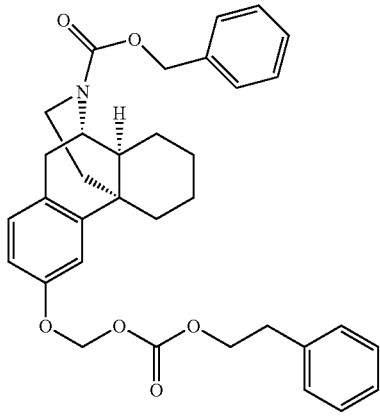

$^1$H NMR (400 MHz, CDCl$_3$) δ 7.38-7.19 (m, 10H), 7.09-7.00 (m, 1H), 6.94 (s, 1H), 6.86 (dd, J=8.4, 2.4 Hz, 1H), 5.75 and 5.71 (AB q, J=6.8 Hz, 2H), 5.17-5.12 (m, 2H), 4.46-4.31 (m, 3H), 3.92-3.84 (m, 1H), 3.29-3.05 (m, 1H), 2.99 (t, J=7.2 Hz, 2H), 2.74-2.60 (m, 2H), 2.35-2.29 (m, 1H), 1.74-1.43 (m, 5H), 1.40-1.22 (m, 4H), 1.10-0.98 (m, 1H).

MH+ 556.

Example 29

(+)-(Morphinan-3-yloxy)methyl phenethyl carbonate TFA

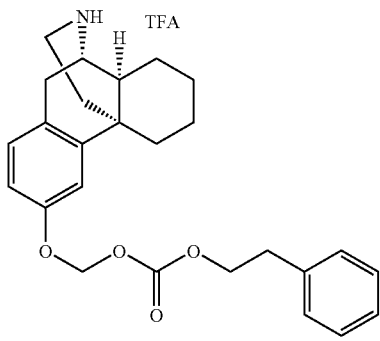

$^1$H NMR (400 MHz, CDCl$_3$) δ 9.11 (br s, 1H), 7.36-7.18 (m, 5H), 7.13 (d, J=8.4 Hz, 1H), 6.98-6.92 (m, 2H), 5.76 and 5.71 (AB q, J=6.8 Hz, 2H), 4.39 (t, J=7.2 Hz, 2H), 3.65 (m, 1H), 3.29-3.05 (m, 3H), 2.99 (t, J=7.2 Hz, 2H), 2.84-2.73 (m, 1H), 2.35 (d, J=13.2 Hz, 1H), 2.03 (d, J=13.2 Hz, 1H), 1.95-1.87 (m, 1H), 1.69-1.36 (m, 6H), 1.30-1.21 (m, 1H), 1.10-1.01 (m, 1H).

MH+ 422.

Example 30

(+)-[N-(Benzyloxycarbonyl)morphinan-3-yloxy]methyl 1-phenylpropan-2-yl carbonate

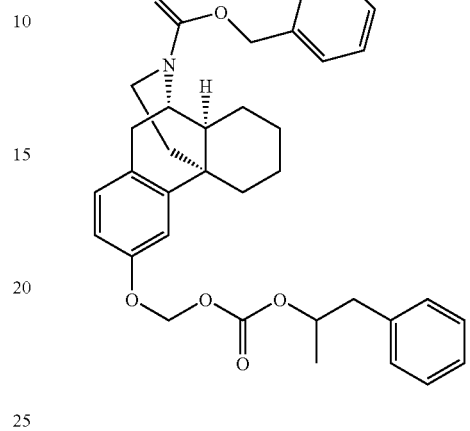

$^1$H NMR (400 MHz, CDCl$_3$) δ 7.39-7.33 (m, 6H), 7.25-7.17 (m, 4H), 7.03 (t, J=8.8 Hz, 1H), 6.95 (d, J=2.4 Hz, 1H), 6.86 (dd, J=8.4, 2.4 Hz, 1H), 5.72 and 5.68 (AB q, J=6.8 Hz, 2H), 5.16-5.11 (m, 2H), 5.04-4.97 (m, 1H), 4.43-4.31 (m, 1H), 3.96-3.84 (m, 1H), 3.15-2.98 (m, 2H), 2.81-2.76 (m, 1H), 2.73-2.56 (m, 2H), 2.35-2.32 (m, 1H), 1.73-1.45 (m, 4H), 1.40-1.30 (m, 5H), 1.28 (d, J=6.4 Hz, 3H), 1.09-1.01 (m, 1H).

MH+ 570.

Example 31

(+)-(Morphinan-3-yloxy)methyl 1-phenylpropan-2-yl carbonate TFA

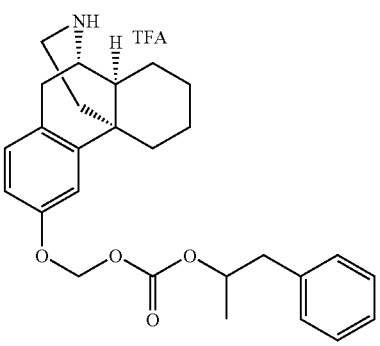

$^1$H NMR (400 MHz, CDCl$_3$) δ 9.33 (br s, 1H), 7.28-7.16 (m, 5H), 7.12 (d, J=8.2 Hz, 1H), 7.08-7.01 (m, 1H), 6.96-6.90 (m, 2H), 5.73 and 5.68 (AB q, J=6.4 Hz, 2H), 5.08-4.98 (m, 1H), 3.63 (m, 1H), 3.20-2.98 (m, 4H), 2.82-2.73 (m, 1H), 2.34 (d, J=13.6 Hz, 1H), 2.09 (d, J=12.8 Hz, 1H), 1.95-1.88 (m, 1H), 1.69-1.36 (m, 7H), 1.29 (d, J=5.6 Hz, 3H), 1.28-1.22 (m, 1H), 1.10-1.01 (m, 1H).

MH+ 436.

Example 32

(+)-[N-(Benzyloxycarbonyl)morphinan-3-yloxy]methyl ethyl carbonate

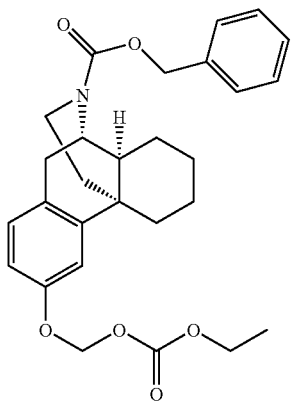

$^1$H NMR (400 MHz, CDCl$_3$) δ 7.39-7.32 (m, 5H), 7.05-7.01 (m, 1H), 6.96 (s, 1H), 6.88 (dd, J=8.4, 2.4 Hz, 1H), 5.77 and 5.72 (AB q, J=6.4 Hz, 2H), 5.17-5.12 (m, 2H), 4.44-4.32 (m, 1H), 4.24 (q, J=6.8 Hz, 2H), 3.96-3.83 (m, 1H), 3.16-3.04 (m, 1H), 2.76-2.56 (m, 3H), 2.38-2.31 (m, 1H), 1.73-1.49 (m, 5H), 1.44-1.33 (m, 3H), 1.32 (t, J=6.8 Hz, 3H), 1.29-1.23 (m, 1H), 1.09-1.00 (m, 1H).

MH+ 480.

Example 33

(+)-Ethyl(morphinan-3-yloxy)methyl carbonate TFA

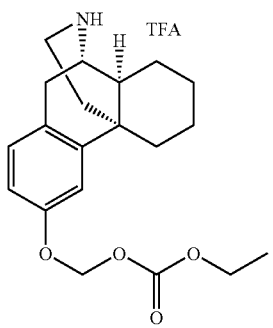

$^1$H NMR (400 MHz, CDCl$_3$) δ 8.93 (br s, 1H), 7.13 (d, J=8.4 Hz, 1H), 6.98-6.94 (m, 2H), 5.78 and 5.73 (AB q, J=6.8 Hz, 2H), 4.25 (q, J=7.2 Hz, 2H), 3.67 (m, 1H), 3.23-3.06 (m, 3H), 2.78 (m, 1H), 2.36 (d, J=13.6 Hz, 1H), 2.05 (d, J=12.4 Hz, 1H), 1.95-1.86 (m, 1H), 1.70-1.36 (m, 6H), 1.32 (t, J=7.2 Hz, 3H), 1.29-1.23 (m, 1H), 1.11-1.00 (m, 1H).

MH+ 346.

Example 34

(+)[N-(Benzyloxycarbonyl)morphinan-3-yloxy]methyl methyl carbonate

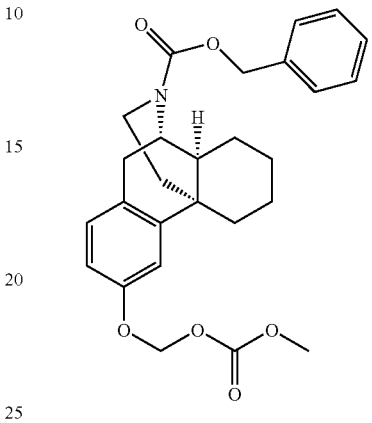

$^1$H NMR (400 MHz, CDCl$_3$) δ 7.39-7.31 (m, 5H), 7.05-7.01 (m, 1H), 6.96 (s, 1H), 6.87 (dd, J=8.4, 2.4 Hz, 1H), 5.78 and 5.73 (AB q, J=6.4 Hz, 2H), 5.17-5.12 (m, 1H), 4.42-4.31 (m, 1H), 3.96-3.84 (m, 1H), 3.83 (s, 3H), 3.14-3.05 (m, 1H), 2.77-2.56 (m, 1H), 2.35-2.32 (m, 1H), 1.72-1.46 (m, 6H), 1.42-1.21 (m, 5H), 1.09-0.90 (m, 1H).

MH+ 466.

Example 35

(+)-Methyl(morphinan-3-yloxy)methyl carbonate TFA

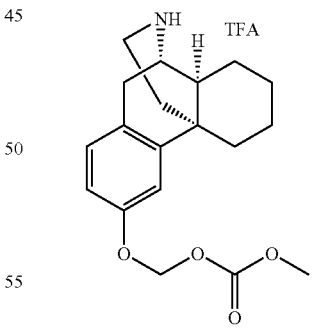

$^1$H NMR (400 MHz, CDCl$_3$) δ 8.92 (br s, 1H), 7.13 (d, J=8.4 Hz, 1H), 6.97-6.94 (m, 2H), 5.78 and 5.73 (AB q, J=6.8 Hz, 2H), 3.83 (s, 3H), 3.67 (m, 1H), 3.24-3.06 (m, 3H), 2.78 (m, 1H), 2.36 (d, J=13.2 Hz, 1H), 2.04 (d, J=12.0 Hz, 1H), 1.95-1.86 (m, 1H), 1.70-1.36 (m, 6H), 1.32-1.20 (m, 1H), 1.11-1.00 (m, 1H).

MH+ 332.

Example 36

(+)-[N-(Benzyloxycarbonyl)morphinan-3-yloxy]methyl cyclobutyl carbonate

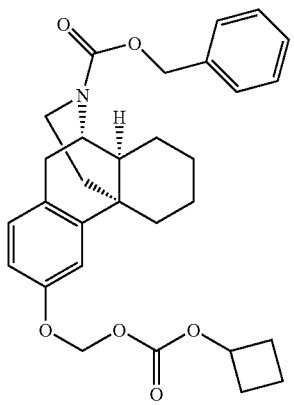

$^1$H NMR (400 MHz, CDCl$_3$) δ 7.40-7.29 (m, 5H), 7.05-7.00 (m, 1H), 6.96 (s, 1H), 6.87 (dd, J=8.4, 2.8 Hz, 1H), 5.75 and 5.70 (AB q, J=6.4 Hz, 2H), 5.17-5.12 (m, 2H), 5.00-4.92 (m, 1H), 4.42-4.31 (m, 1H), 3.96-3.82 (m, 1H), 3.16-3.03 (m, 1H), 2.76-2.56 (m, 2H), 2.45-2.31 (m, 3H), 2.25-2.08 (m, 2H), 1.88-1.76 (m, 1H), 1.73-1.45 (m, 6H), 1.42-1.22 (m, 4H), 1.08-1.00 (m, 1H).

MH+ 506.

Example 37

(+)-Cyclobutyl(morphinan-3-yloxy)methyl carbonate TFA

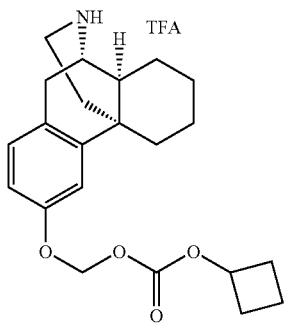

$^1$H NMR (400 MHz, CDCl$_3$) δ 9.38 (br s, 1H), 7.12 (d, J=8.2 Hz, 1H), 6.97-6.93 (m, 2H), 5.76 and 5.71 (AB q, J=6.4 Hz, 2H), 5.00-4.92 (m, 1H), 3.62 (m, 1H), 3.21-3.04 (m, 3H), 2.74 (m, 1H), 2.46-2.31 (m, 4H), 2.25-2.07 (m, 4H), 1.99-1.77 (m, 2H), 1.71-1.35 (m, 5H), 1.32-1.21 (m, 1H), 1.10-1.00 (m, 1H).

MH+ 372.

Example 38

(+)-[N-(Benzyloxycarbonyl)morphinan-3-yloxy]methyl hexyl carbonate

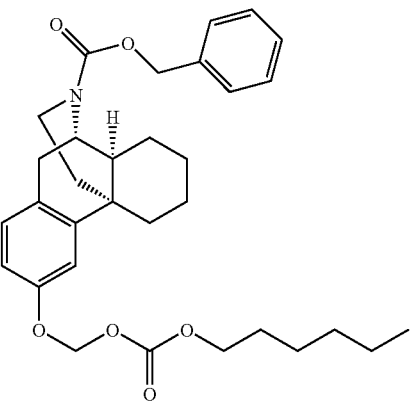

$^1$H NMR (400 MHz, CDCl$_3$) δ 7.39-7.28 (m, 5H), 7.03 (t, J=8.8 Hz, 1H), 6.96 (s, 1H), 6.88 (dd, J=8.4, 2.4 Hz, 1H), 5.77 and 5.72 (AB q, J=6.8 Hz, 2H), 5.21-5.12 (m, 1H), 4.42-4.31 (m, 1H), 4.17 (t, J=7.2 Hz, 2H), 3.96-3.84 (m, 1H), 3.14-3.05 (m, 1H), 2.72-2.57 (m, 2H), 2.36-2.32 (m, 1H), 1.72-1.43 (m, 7H), 1.43-1.23 (m, 11H), 1.05-0.96 (m, 1H), 0.88 (t, J=6.8 Hz, 3H).

MH+ 536.

Example 39

(+)-Hexyl(morphinan-3-yloxy)methyl carbonate TFA

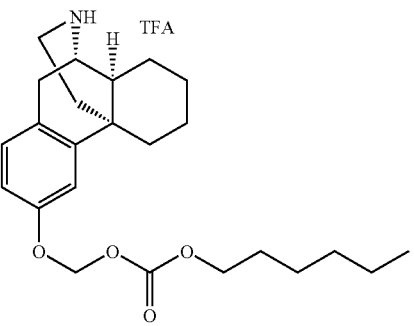

$^1$H NMR (400 MHz, CDCl$_3$) δ 9.28 (br s, 1H), 7.12 (d, J=8.4 Hz, 1H), 7.00-6.93 (m, 2H), 5.78 and 5.74 (AB q, J=6.8 Hz, 2H), 4.20 (t, J=6.4 Hz, 2H), 3.65 (m, 1H), 3.25-2.70 (m, 5H), 2.36 (d, J=13.6 Hz, 1H), 2.11 (d, J=12.0 Hz, 1H), 1.98-1.88 (m, 1H), 1.78-1.22 (m, 14H), 1.16-1.01 (m, 1H), 0.88 (t, J=7.2 Hz, 3H).

MH+ 402.

Example 40

(+)-[N-(Benzyloxycarbonyl)morphinan-3-yloxy]methyl pentan-2-yl carbonate

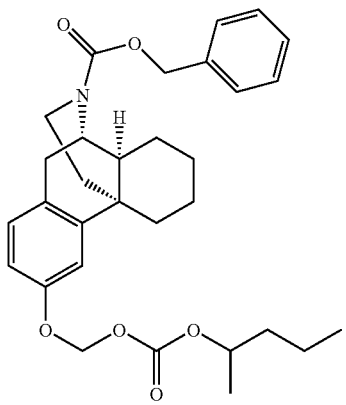

$^1$H NMR (400 MHz, CDCl$_3$) δ 7.39-7.31 (m, 5H), 7.03 (t, J=8.4 Hz, 1H), 6.96 (s, 1H), 6.88 (dd, J=8.4, 2.4 Hz, 1H), 5.76 and 5.72 (AB q, J=6.4 Hz, 2H), 5.17-5.12 (m, 2H), 4.86-4.78 (m, 1H), 4.43-4.31 (m, 1H), 3.95-3.82 (m, 1H), 3.14-3.04 (m, 1H), 2.72-2.56 (m, 2H), 2.38-2.32 (m, 1H), 2.20-2.06 (m, 3H), 1.73-1.59 (m, 3H), 1.56-1.43 (m, 3H), 1.42-1.30 (m, 4H), 1.26 (d, J=6.4 Hz, 3H), 1.08-1.01 (m, 1H), 0.91 (t, J=7.2 Hz, 3H).
MH+ 522.

Example 41

(+)-(Morphinan-3-yloxy)methyl pentan-2-yl carbonate TFA

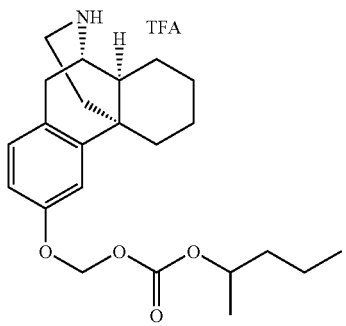

$^1$H NMR (400 MHz, CDCl$_3$) δ 9.33 (br s, 1H), 7.12 (d, J=8.0 Hz, 1H), 6.89-6.89 (m, 2H), 5.77 and 5.72 (AB q, J=6.8 Hz, 2H), 4.86-4.78 (m, 1H), 3.61 (m, 1H), 3.22-3.02 (m, 3H), 2.75 (m, 1H), 2.35 (d, J=14.0 Hz, 1H), 2.20-2.06 (m, 3H), 1.98-1.87 (m, 1H), 1.70-1.33 (m, 8H), 1.27 (d, J=6.4 Hz, 3H), 1.25-1.23 (m, 1H), 1.11-0.95 (m, 1H), 0.91 (t, J=7.2 Hz, 3H).
MH+ 388.

Example 42

(+)-Decyl(morphinan-3-yloxy)methyl carbonate TFA

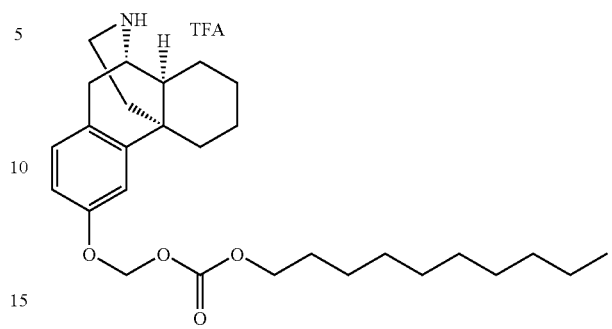

$^1$H NMR (400 MHz, CDCl$_3$) δ 9.09 (br s, 1H), 7.13 (d, J=8.0 Hz, 1H), 6.97-6.93 (m, 2H), 5.78 and 5.72 (AB q, J=6.8 Hz, 2H), 4.18 (t, J=6.8 Hz, 2H), 3.65 (m, 1H), 3.22-3.07 (m, 3H), 2.80-2.72 (m, 1H), 2.36 (d, J=13.6 Hz, 1H), 2.06 (d, J=12.4 Hz, 1H), 1.96-1.88 (m, 1H), 1.71-1.63 (m, 4H), 1.59-1.21 (m, 19H), 1.10-1.01 (m, 1H), 0.88 (t, J=6.4 Hz, 3H).
MH+ 458.

Example 43

(+)-[N-(Benzyloxycarbonyl)morphinan-3-yloxy]methyl isobutyrate

Step 1: (+)-[N-(Benzyloxycarbonyl)morphinan-3-yloxy]methyl methyl sulfide

To Sodium hydride (763 mg of 60% dispersion in mineral oil, 19.1 mmol) in HMPA (15 mL) was added a solution of (+)-3-hydroxy-N-(benzyloxycarbonyl)morphinan (6.00 g, 15.9 mmol) from Example 1 in HMPA (50 mL) at room temperature. The reaction mixture was stirred for 30 min and then chloromethyl methyl sulfide (1.60 mL, 19.1 mmol) was added dropwise. The reaction mixture was stirred vigorously at room temperature overnight. The product was extracted with EtOAc (500 mL). The EtOAc layer was washed with saturated NaHCO$_3$ solution and dried over MgSO$_4$, filtered and evaporated under vacuum to provide the crude product, which was further purified by prep reverse-phase HPLC to afford the title compound (1.78 g, 26%) as a yellow gum.
MH+ 438.

Step 2: (+)-[N-(Benzyloxycarbonyl)morphinan-3-yloxy]methyl isobutyrate

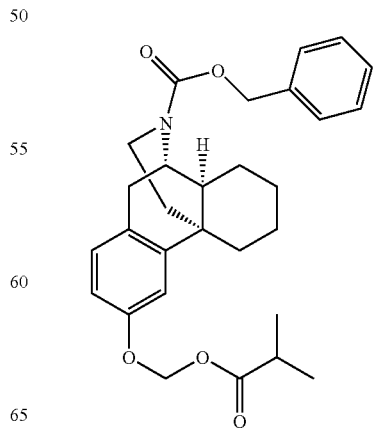

To (+)[N-(Benzyloxycarbonyl)morphinan-3-yloxy]methyl methyl sulfide (1.78 g, 4.07 mmol) in DCM (40 mL) was added sulfuryl chloride (6.1 mL, 6.11 mmol) at room temperature. The reaction mixture was stirred at room temperature overnight. After removal of excess reagent and DCM by rotary evaporation, the product was dried under vacuum to afford (+)-[N-(benzyloxycarbonyl)morphinan-3-yloxy]methyl chloride as a yellow gum. Then, it was added to a stirred suspension of cesium carbonate (1.59 g, 4.88 mmol) and isobutyric acid (0.45 mL, 4.88 mmol) in acetone (20 mL) at room temperature. The reaction mixture was stirred at room temperature overnight. After the reaction was completed, the reaction mixture was filtered and evaporated under vacuum to provide the crude product, which was further purified by prep reverse-phase HPLC to afford the title compound (0.844 g, 43%) as a yellow solid.

$^1$H NMR (400 MHz, CDCl$_3$) δ 7.38-7.33 (m, 5H), 7.02-6.93 (m, 3H), 5.75 (s, 2H), 5.17-5.12 (m, 2H), 4.36 (d, J=43.6 Hz, 1H), 3.94-3.84 (m, 1H), 3.14-3.04 (m, 1H), 2.72-2.56 (m, 3H), 2.33 (d, J=12.0 Hz, 1H), 1.73-1.42 (m, 6H), 1.39-1.25 (m, 3H), 1.20 (d, J=7.2 Hz, 6H), 1.11-1.00 (m, 1H).

MH+ 478.

Example 44

(+)-(Morphinan-3-yloxy)methyl isobutyrate

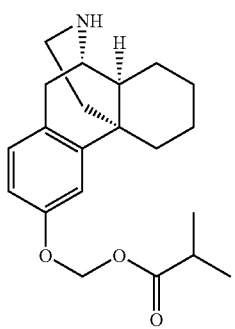

(+)-[N-(Benzyloxycarbonyl)morphinan-3-yloxy]methyl isobutyrate (4.12 g, 8.63 mmol) from Example 44 was subjected to hydrogenation (balloon) on 10% Pd/C (600 mg) in EtOH (100 mL) at room temperature. After the reaction was completed, the reaction mixture was filtered through a Celite, and washed with EtOH (300 mL). The combined EtOH solution was evaporated under vacuum. The residue was further purified by reverse-phase prep HPLC to provide the title compound (1.11 g, 37%) as a light yellow gum.

$^1$H NMR (400 MHz, CDCl$_3$) δ 7.05 (d, J=8.4 Hz, 1H), 6.93 (d, J=2.8 Hz, 1H), 6.83 (dd, J=8.4, 2.8 Hz, 1H), 5.76 and 5.74 (AB q, J=6.8 Hz, 2H), 3.15-3.06 (m, 2H), 2.77-2.67 (m, 2H), 2.63-2.55 (m, 2H), 2.28 (d, J=13.2 Hz, 1H), 1.79-1.74 (m, 1H), 1.66-1.50 (m, 3H), 1.39-1.26 (m, 5H), 1.18 (d, J=6.8 Hz, 6H), 1.05-1.01 (m, 1H).

MH+ 344.

Example 45

(+)-[N-(Benzyloxycarbonyl)morphinan-3-yloxy]methyl pivalate

Step 1: (+)-[N-(Benzyloxycarbonyl)morphinan-3-yloxy]methyl pivalate

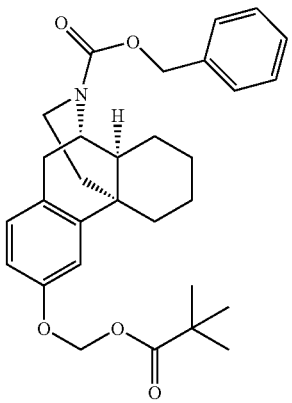

To (+)-3-hydroxy-N-(benzyloxycarbonyl)morphinan (12.0 g, 31.8 mmol) from Example 1 and cesium carbonate (11.4 g, 35.0 mmol) in acetone (150 mL) was added iodomethyl pivalate (8.46 g, 35.0 mmol) (see Bristol-Myers Squibb Company, U.S. Pat. No. 5,470,845 A1 (1995/11/28), Appl.; US1994-266843 (1994 Jul. 5)) at room temperature. The reaction mixture was stirred vigorously at room temperature overnight. The acetone was then removed by rotary evaporation under vacuum. To the residue was added saturated NaHCO$_3$ solution. The mixture was extracted with EtOAc (150 mL×2). The combined organics were washed with 1N HCl solution (100 mL), dried over MgSO$_4$, filtered, and evaporated under vacuum to provide the crude product, which was further purified by prep reverse-phase HPLC to afford the title compound (13.2 g, 84%) as a yellow gum.

$^1$H NMR (400 MHz, CDCl$_3$) δ 7.39-7.32 (m, 5H), 7.02 (t, J=8.8 Hz, 1H), 6.97 (s, 1H), 6.84 (dd, J=8.4, 2.4 Hz, 1H), 5.76 and 5.72 (AB q, J=6.4 Hz, 2H), 5.20-5.09 (m, 2H), 4.37 (br d, J=43.6 Hz, 1H), 3.95-3.84 (m, 1H), 3.15-3.05 (m, 1H), 2.72-2.59 (m, 2H), 2.34 (d, J=12.0 Hz, 1H), 1.73-1.42 (m, 6H), 1.39-1.25 (m, 3H), 1.21 (s, 9H), 1.11-1.00 (m, 1H).

MH+ 492.

Example 46

(+)-(Morphinan-3-yloxy)methyl pivalate

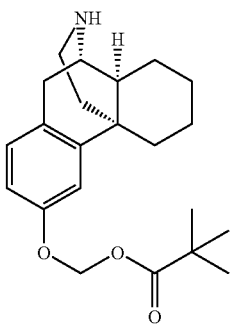

(+)-[N-(Benzyloxycarbonyl)morphinan-3-yloxy]methyl pivalate (13.2 g, 26.8 mmol) from Example 46 was subjected to hydrogenation (balloon) on 10% Pd/C (2.0 g) in EtOH (100 mL) at room temperature. After the reaction was completed, the reaction mixture was filtered through a Celite, and washed with EtOH (300 mL). The combined EtOH solution was evaporated under vacuum. The residue was further purified by reverse-phase prep HPLC to provide the title compound (4.31 g, 45%) as a light yellow gum.

¹H NMR (300 MHz, CDCl₃) δ 7.05 (d, J=8.4 Hz, 1H), 6.94 (d, J=2.7 Hz, 1H), 6.83 (dd, J=8.4, 2.7 Hz, 1H), 5.76 and 5.71 (AB q, J=6.4 Hz, 2H), 3.16-3.08 (m, 2H), 2.80-2.54 (m, 4H), 2.28 (d, J=13.2 Hz, 1H), 1.81-1.76 (m, 1H), 1.66-1.50 (m, 3H), 1.42-1.26 (m, 4H), 1.21 (s, 9H), 1.09-1.00 (m, 1H).

MH+ 358.

Example 47

(+)-(Morphinan-3-yloxy)methyl pivalate TFA

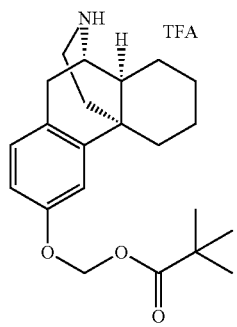

(+)-[N-(Benzyloxycarbonyl)morphinan-3-yloxy]methyl pivalate (4.66 g, 9.48 mmol) from Example 45 was subjected to hydrogenation (balloon) on 10% Pd/C (470 mg) in IPA (40 mL) at room temperature. After the reaction was completed, the reaction mixture was filtered through a Celite, and washed with IPA (20 mL). The combined IPA solution was evaporated under vacuum. The residue was further purified by prep reverse-phase HPLC with 0.1% TFA to provide the title compound (3.79 g, 85%) as a colorless gum.

¹H NMR (400 MHz, CD₃OD) δ 7.18 (d, J=8.4 Hz, 1H), 7.06 (d, J=2.8 Hz, 1H), 6.95 (dd, J=8.4, 2.8 Hz, 1H), 5.79 and 5.73 (AB q, J=6.8 Hz, 2H), 3.70-3.68 (m, 1H), 3.33-3.26 (m, 1H), 3.10 (dd, J=13.2, 3.2 Hz, 1H), 2.95 (br d, J=19.2 Hz, 1H), 2.74-2.67 (m, 1H), 2.46 (d, J=14.0 Hz, 1H), 1.94 (d, J=12.0 Hz, 1H), 1.87-1.78 (m, 1H), 1.71 (d, J=12.8 Hz, 1H), 1.60-1.40 (m, 5H), 1.34-1.25 (m, 1H), 1.17 (s, 9H), 1.15-1.07 (m, 1H).

MH+ 358.

The following compounds of Examples 48 to 78 were obtained by repeating the procedure of Example 45 and Example 47.

Example 48

(+)-(Morphinan-3-yloxy)methyl 3,3-dimethylbutanoate TFA

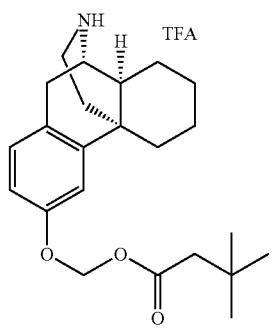

¹H NMR (400 MHz, CDCl₃) δ 9.45 (br, 2H), 7.11 (d, J=8.4 Hz, 1H), 6.94 (d, J=2.8 Hz, 1H), 6.90 (dd, J=8.4, 2.8 Hz, 1H), 5.75 (s, 2H), 3.15-3.06 (m, 2H), 2.77-2.67 (m, 2H), 2.63-2.55 (m, 2H), 2.24 (d, J=4.0 Hz, 2H), 1.79-1.74 (m, 1H), 1.66-1.50 (m, 3H), 1.39-1.26 (m, 5H), 1.28-1.24 (m, 1H), 1.05 (s, 9H).

MH+ 372.

Example 49

(+)-[N-(Benzyloxycarbonyl)morphinan-3-yloxy]methyl hexanoate

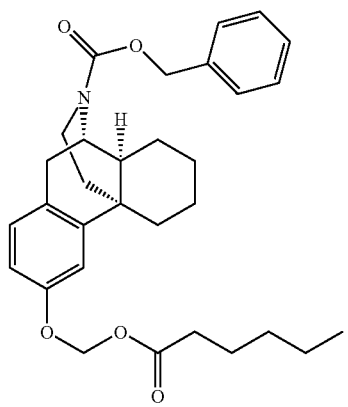

¹H NMR (400 MHz, CDCl₃) δ 7.34 (br, 5H), 7.01 (d, J=8.4 Hz, 1H), 6.94 (d, J=2.4 Hz, 1H), 6.83 (dd, J=8.4, 2.4 Hz, 1H), 5.75 and 5.73 (AB q, J=6.4 Hz, 2H), 5.13 (br, 2H), 4.40 (br, 1H), 3.89 (br, 1H), 3.09 (d, J=8.8 Hz, 1H), 2.70-2.62 (m, 2H), 2.34 (t, J=7.6 Hz, 2H), 1.75-1.40 (m, 6H), 1.39-1.23 (m, 9H), 1.06-0.90 (m, 2H), 0.85 (t, J=7.2 Hz, 3H).

MH+ 506.

Example 50

(+)-(Morphinan-3-yloxy)methyl hexanoate TFA

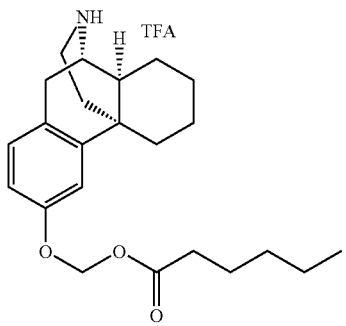

¹H NMR (400 MHz, CDCl₃) δ 9.20 (br, 2H), 7.10 (d, J=8.4 Hz, 1H), 6.93 (d, J=2.0 Hz, 1H), 6.90 (dd, J=8.4, 2.4 Hz, 1H), 5.75 and 5.73 (AB q, J=6.8 Hz, 2H), 3.63 (br, 2H), 3.17-3.07 (m, 5H), 2.75 (br, 2H), 2.34 (d, J=7.6 Hz, 2H), 2.06 (d, J=12.4 Hz, 2H), 1.97-1.88 (m, 2H), 1.68-1.23 (m, 7H), 1.09-0.92 (m, 2H), 0.86 (t, J=6.8 Hz, 3H).

MH+ 372.

Example 51

(+)-[N-(Benzyloxycarbonyl)morphinan-3-yloxy]methyl 2-propylpentanoate

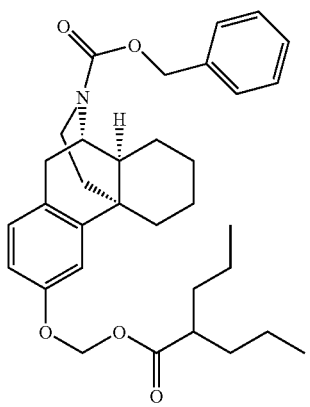

¹H NMR (400 MHz, CDCl₃) δ 7.34 (br, 5H), 7.01 (d, J=8.4 Hz, 1H), 6.95 (d, J=2.4 Hz, 1H), 6.83 (dd, J=8.4, 2.4 Hz, 1H), 5.76 and 5.74 (AB q, J=6.8 Hz, 2H), 5.12 (br, 2H), 4.39 (br, 1H), 3.88 (br, 1H), 3.12-3.06 (m, 1H), 2.70-2.62 (m, 2H), 2.43-2.31 (m, 2H), 1.70-1.18 (m, 17H), 1.09-0.97 (m, 1H), 0.81 (t, J=7.2 Hz, 6H).

MH+ 534.

Example 52

(+)-(Morphinan-3-yloxy)methyl 2-propylpentanoate TFA

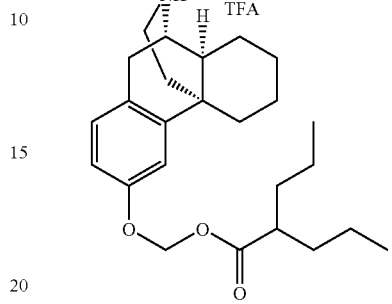

¹H NMR (400 MHz, CDCl₃) δ 8.89 (br, 1H), 8.50 (br, 1H), 7.10 (d, J=8.4 Hz, 1H), 6.95 (d, J=2.4 Hz, 1H), 6.91 (dd, J=8.4, 2.4 Hz, 1H), 5.77 and 5.74 (AB q, J=6.8 Hz, 2H), 3.72 (br, 1H), 3.25-3.15 (m, 2H), 3.06 (br d, J=19.2 Hz, 1H), 2.79-2.77 (m, 1H), 2.44-2.34 (m, 2H), 2.02 (d, J=12.0 Hz, 1H), 1.94-1.86 (m, 1H), 1.68 (d, J=13.2 Hz, 1H), 1.66-1.36 (m, 9H), 1.30-1.19 (m, 5H), 1.10-1.01 (m, 1H), 0.82 (t, J=7.2 Hz, 6H).

MH+ 400.

Example 53

(+)[N-(Benzyloxycarbonyl)morphinan-3-yloxy]methyl 2-ethylbutanoate

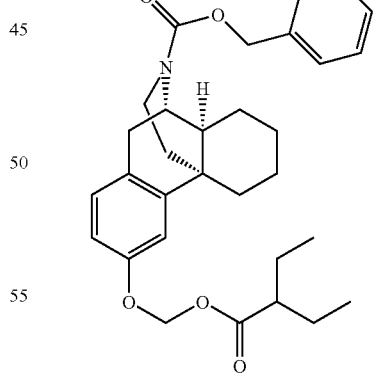

¹H NMR (400 MHz, CDCl₃) δ 7.34 (br, 5H), 7.01 (d, J=8.0 Hz, 1H), 6.95 (d, J=2.4 Hz, 1H), 6.83 (dd, J=8.4, 2.4 Hz, 1H), 5.77 and 5.74 (AB q, J=6.4 Hz, 2H), 5.13 (br, 2H), 4.40 (br, 2H), 3.88 (br, 2H), 3.12-3.06 (m, 2H), 2.69-2.62 (m, 2H), 2.33 (d, J=12.8 Hz, 1H), 2.27-2.20 (m, 1H), 1.70-1.45 (m, 6H), 1.38-1.22 (m, 4H), 1.08-0.96 (m, 1H), 0.84 (t, J=7.6 Hz, 6H).

MH+ 506.

Example 54

(+)-(Morphinan-3-yloxy)methyl 2-ethylbutanoate TFA

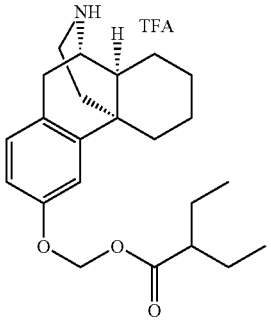

$^1$H NMR (400 MHz, CDCl$_3$) δ 8.67 (br, 1H), 7.80 (br, 1H), 7.11 (d, J=8.4 Hz, 1H), 6.96 (d, J=2.4 Hz, 1H), 6.91 (dd, J=8.4, 2.8 Hz, 1H), 5.78 and 5.74 (AB q, J=6.8 Hz, 2H), 3.70 (br, 1H), 3.24-3.13 (m, 2H), 3.07 (br d, J=19.2 Hz, 1H), 2.77-2.75 (m, 1H), 2.35 (d, J=14.0 Hz, 1H), 2.28-2.21 (m, 1H), 2.03 (d, J=12.4 Hz, 1H), 1.94-1.86 (m, 1H), 1.69-1.35 (m, 10H), 1.29-1.23 (m, 1H), 1.11-1.01 (m, 1H), 0.84 (t, J=7.6 Hz, 6H).

MH+ 372.

Example 55

(+)-[N-(Benzyloxycarbonyl)morphinan-3-yloxy]methyl cyclohexanoate

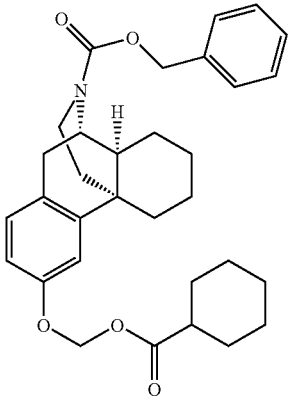

$^1$H NMR (400 MHz, CDCl$_3$) δ 7.36-7.32 (m, 5H), 7.09-6.99 (m, 1H), 6.94 (s, 1H), 6.86-6.81 (m, 1H), 5.74 and 5.72 (AB q, J=6.4 Hz, 2H), 5.16-5.12 (m, 2H), 4.36 (br d, J=42.0 Hz, 2H), 3.94-3.84 (m, 2H), 3.12-3.09 (m, 2H), 2.67-2.49 (m, 3H), 2.37-2.30 (m, 2H), 2.05 (d, J=13.6 Hz, 2H), 1.89 (d, J=11.2 Hz, 1H), 1.88-1.79 (m, 1H), 1.70-1.17 (m, 11H), 1.09-1.00 (m, 1H).

MH+ 518.

Example 56

(+)-(Morphinan-3-yloxy)methyl cyclohexanoate TFA

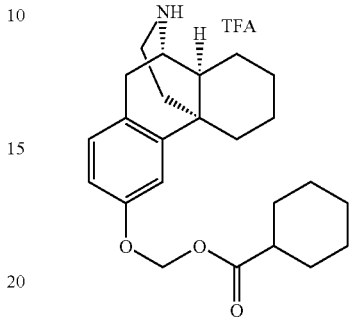

$^1$H NMR (400 MHz, CDCl$_3$) δ 11.06 (br, 1H), 8.73 (br, 1H), 7.13 (dd, J=25.2, 8.4 Hz, 1H), 6.96-6.88 (m, 2H), 5.75 and 5.71 (AB q, J=6.8 Hz, 2H), 3.68 (br, 1H), 3.23-3.02 (m, 2H), 2.76 (br, 1H), 2.57-2.50 (m, 1H), 2.36-2.31 (m, 2H), 2.06-2.03 (m, 2H), 1.90-1.13 (m, 17H), 1.09-1.01 (m, 1H).

MH+ 384.

Example 57

(+)-[N-(Benzyloxycarbonyl)morphinan-3-yloxy]methyl cyclopentanoate

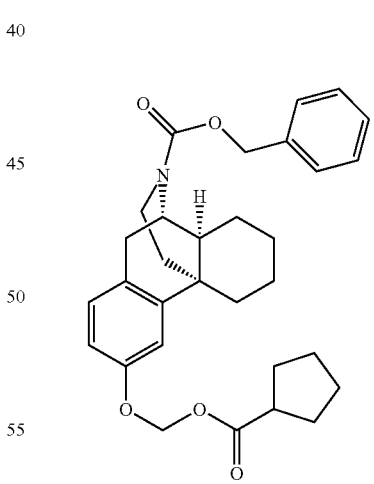

$^1$H NMR (400 MHz, CDCl$_3$) δ 7.37-7.30 (m, 5H), 7.01 (t, J=9.2 Hz, 1H), 6.95 (s, 1H), 6.83 (dd, J=8.4, 2.4 Hz, 1H), 5.74 (s, 2H), 5.16-5.12 (m, 2H), 4.36 (br d, J=42.0 Hz, 2H), 3.96-3.83 (m, 2H), 3.12-3.04 (m, 2H), 2.79-2.57 (m, 3H), 2.33 (d, J=12.4 Hz, 2H), 1.90-1.23 (m, 12H), 1.06-1.03 (m, 1H), 0.88-0.85 (m, 1H).

MH+ 504.

Example 58

(+)-(Morphinan-3-yloxy)methyl cyclopentanoate
TFA

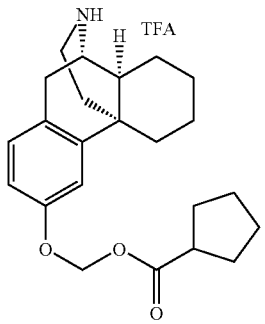

$^1$H NMR (400 MHz, CDCl$_3$) δ 8.79 (br, 1H), 8.42 (br, 1H), 7.11 (d, J=8.4 Hz, 1H), 6.95 (d, J=2.4 Hz, 1H), 6.91 (dd, J=8.4, 2.4 Hz, 1H), 5.75 and 5.73 (AB q, J=6.8 Hz, 2H), 3.69 (br, 1H), 3.23-3.12 (m, 3H), 2.81-2.73 (m, 2H), 2.34 (d, J=13.6 Hz, 1H), 2.04 (d, J=12.4 Hz, 1H), 1.98-1.35 (m, 15H), 1.30-1.20 (m, 1H), 1.11-1.01 (m, 1H).
MH+ 370.

Example 59

(+)-[N-(Benzyloxycarbonyl)morphinan-3-yloxy]
methyl 2-ethylhexanoate

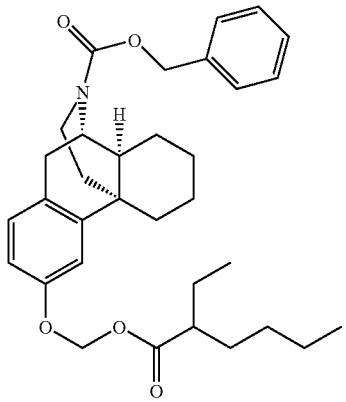

$^1$H NMR (400 MHz, CDCl$_3$) δ 7.36-7.32 (m, 5H), 7.02-6.99 (m, 1H), 6.95 (s, 1H), 6.83 (dd, J=8.4, 2.4 Hz, 1H), 5.77 and 5.74 (AB q, J=6.8 Hz, 2H), 5.12 (br, 2H), 4.36 (br d, J=41.6 Hz, 1H), 3.93-3.84 (m, 1H), 3.12-3.07 (m, 1H), 2.71-2.64 (m, 2H), 2.35-2.26 (m, 2H), 1.67-1.15 (m, 16H), 1.08-0.99 (m, 1H), 0.86-0.78 (m, 6H).
MH+ 534.

Example 60

(+)-(Morphinan-3-yloxy)methyl 2-ethylhexanoate
TFA

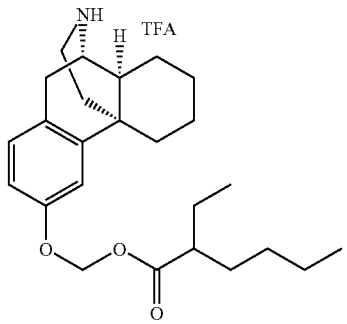

$^1$H NMR (400 MHz, CDCl$_3$) δ 8.76 (br, 1H), 7.11 (d, J=8.4 Hz, 1H), 6.95 (d, J=2.0 Hz, 1H), 6.92 (dd, J=8.4, 2.0 Hz, 1H), 5.81 (br, 1H), 5.78 and 5.75 (AB q, J=6.8 Hz, 2H), 3.73 (br, 1H), 3.25-3.08 (m, 2H), 2.81-2.73 (m, 1H), 2.36-2.27 (m, 2H), 2.06 (d, J=12.0 Hz, 1H), 1.96-1.91 (m, 1H), 1.69-0.99 (m, 17H), 0.86-0.77 (m, 6H).
MH+ 400.

Example 61

(+)-[N-(Benzyloxycarbonyl)morphinan-3-yloxy]
methyl butanoate

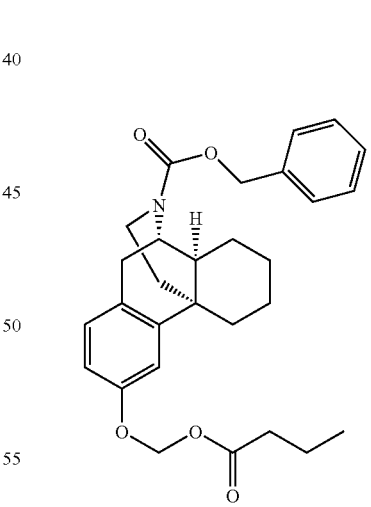

$^1$H NMR (400 MHz, CDCl$_3$) δ 7.34 (br, 5H), 7.02 (d, J=8.0 Hz, 1H), 6.94 (d, J=2.4 Hz, 1H), 6.84 (dd, J=8.4, 2.4 Hz, 1H), 5.76 and 5.73 (Ab q, J=6.4 Hz, 2H), 5.13 (br, 2H), 4.41 (br, 1H), 3.88 (br, 1H), 3.09 (d, J=14.8 Hz, 1H), 2.70-2.66 (m, 2H), 2.33 (t, J=7.6 Hz, 2H), 1.71-1.22 (m, 12H), 1.08-0.99 (m, 1H), 0.92 (t, J=7.6 Hz, 3H).
MH+ 478.

Example 62

(+)-(Morphinan-3-yloxy)methyl butanoate TFA

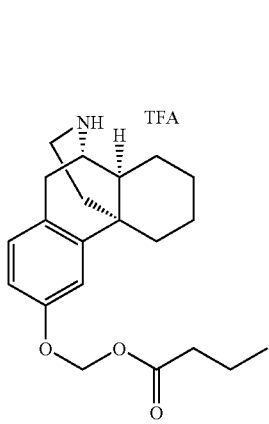

$^1$H NMR (400 MHz, CDCl$_3$) δ 9.76 (br, 1H), 8.23 (br, 1H), 7.12 (d, J=8.4 Hz, 1H), 6.95 (d, J=2.4 Hz, 1H), 6.92 (dd, J=8.4, 2.4 Hz, 1H), 5.76 and 5.75 (AB q, J=6.8 Hz, 2H), 3.75 (br, 1H), 3.27-3.18 (m, 2H), 3.05 (br d, J=19.2 Hz, 1H), 2.81 (br, 1H), 2.37-2.33 (m, 3H), 2.02-2.00 (m, 1H), 1.90 (t, J=12.0 Hz, 1H), 1.70-1.37 (m, 8H), 1.30-1.24 (m, 1H), 1.11-1.02 (m, 1H), 0.93 (t, J=7.6 Hz, 3H).

MH+ 344.

Example 63

(+)-[N-(Benzyloxycarbonyl)morphinan-3-yloxy]methyl pentanoate

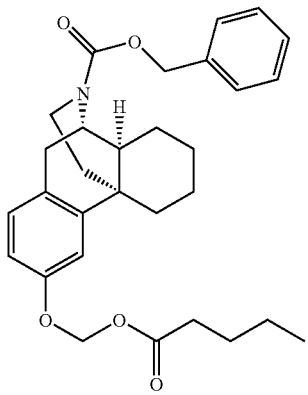

$^1$H NMR (400 MHz, CDCl$_3$) δ 7.33 (br, 5H), 7.02 (d, J=6.8 Hz, 1H), 6.94 (d, J=2.4 Hz, 1H), 6.83 (dd, J=8.4, 2.4 Hz, 1H), 5.75 and 5.73 (Ab q, J=6.4 Hz, 2H), 5.12 (br, 2H), 4.36 (br d, J=40.4 Hz, 1H), 3.87 (br, 1H), 3.11-3.07 (m, 1H), 2.71-2.65 (m, 2H), 2.37-2.31 (m, 3H), 1.77-1.22 (m, 13H), 1.08-1.02 (m, 1H), 0.88 (t, J=7.6 Hz, 3H).

MH+ 492.

Example 64

(+)-(Morphinan-3-yloxy)methyl pentanoate TFA

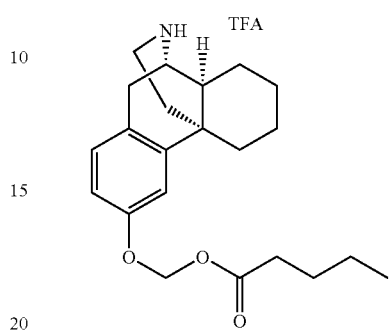

$^1$H NMR (400 MHz, CDCl$_3$) δ 9.65 (br, 1H), 8.40 (br, 1H), 7.12 (d, J=8.4 Hz, 1H), 6.95 (d, J=2.4 Hz, 1H), 6.92 (dd, J=8.4, 2.4 Hz, 1H), 5.76 and 5.74 (AB q, J=6.8 Hz, 2H), 3.74 (br, 1H), 3.29-3.17 (m, 2H), 3.05 (br d, J=19.2 Hz, 1H), 2.81-2.79 (m, 1H), 2.38-2.34 (m, 3H), 2.03-2.01 (m, 1H), 1.94-1.86 (m, 1H), 1.71-1.21 (m, 11H), 1.11-1.02 (m, 1H), 0.88 (t, J=7.6 Hz, 3H).

MH+ 358.

Example 65

(+)-[N-(Benzyloxycarbonyl)morphinan-3-yloxy]methyl 2-methylbutanoate

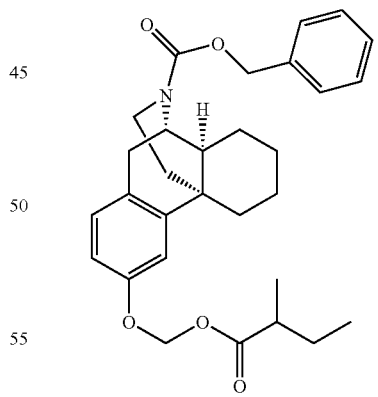

$^1$H NMR (400 MHz, CDCl$_3$) δ 7.34 (br, 5H), 7.01 (d, J=8.4 Hz, 1H), 6.95 (d, J=2.4 Hz, 1H), 6.83 (dd, J=8.4, 2.4 Hz, 1H), 5.76 and 5.73 (AB q, J=6.8 Hz, 2H), 5.13 (br, 2H), 4.40 (br, 1H), 3.88 (br, 1H), 3.09 (dd, J=18.0, 2.8 Hz, 1H), 2.70-2.59 (m, 2H), 2.43-2.38 (m, 1H), 2.33 (d, J=12.8 Hz, 1H), 1.72-1.22 (m, 11H), 1.14 (d, J=6.8 Hz, 3H), 1.08-0.99 (m, 1H), 0.86 (t, J=7.6 Hz, 3H).

MH+ 492.

Example 66

(+)-(Morphinan-3-yloxy)methyl 2-methylbutanoate TFA

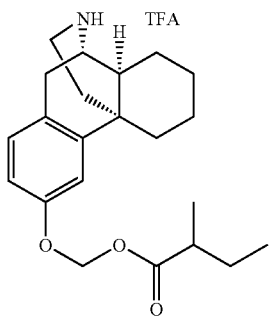

$^1$H NMR (400 MHz, CDCl$_3$) δ 8.53 (br, 1H), 7.95 (br, 1H), 7.12 (d, J=8.4 Hz, 1H), 6.96 (d, J=2.4 Hz, 1H), 6.92 (dd, J=8.4, 2.4 Hz, 1H), 5.77 and 5.74 (AB q, J=6.8 Hz, 2H), 3.74 (br, 1H), 3.26-3.17 (m, 2H), 3.08 (br d, J=19.2 Hz, 1H), 2.79 (br, 1H), 2.45-2.34 (m, 2H), 2.06-2.01 (m, 1H), 1.95-1.89 (m, 1H), 1.71-1.39 (m, 8H), 1.29-1.23 (m, 1H), 1.14 (d, J=6.8 Hz, 3H), 1.08-1.01 (m, 1H), 0.86 (t, J=7.6 Hz, 3H).

MH+ 358.

Example 67

(+)-[N-(Benzyloxycarbonyl)morphinan-3-yloxy]methyl cyclopropanecarboxylate

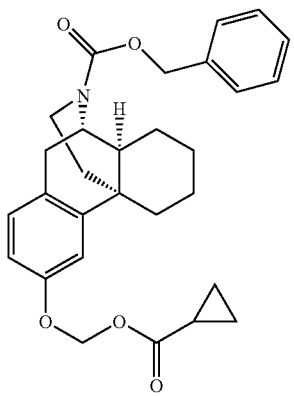

$^1$H NMR (400 MHz, CDCl$_3$) δ 7.37-7.33 (m, 5H), 7.03 (d, J=8.4 Hz, 1H), 6.94 (s, 1H), 6.85 (dd, J=8.4, 2.4 Hz, 1H), 5.75 and 5.72 (AB q, J=6.8 Hz, 2H), 5.20-5.12 (m, 2H), 4.37 (br d, J=42.0 Hz, 1H), 3.94-3.84 (m, 1H), 3.14-3.06 (m, 1H), 2.78-2.54 (m, 2H), 2.33 (d, J=12.4 Hz, 1H), 1.67-1.23 (m, 10H), 1.07-1.03 (m, 3H), 0.91-0.87 (m, 2H).

MH+ 476.

Example 68

(+)-(Morphinan-3-yloxy)methyl cyclopropanecarboxylate TFA

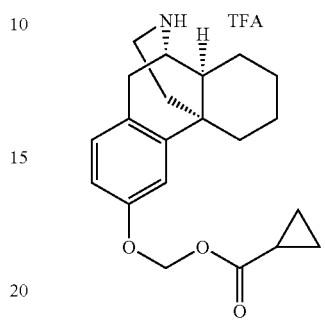

$^1$H NMR (400 MHz, CDCl$_3$) δ 10.35 (br, 1H), 8.32 (br, 1H), 7.12 (d, J=8.4 Hz, 1H), 6.94-6.91 (m, 2H), 5.75 and 5.73 (AB q, J=6.8 Hz, 2H), 3.73 (br, 1H), 3.25-3.19 (m, 2H), 3.04 (br d, J=19.2 Hz, 1H), 2.81-2.75 (m, 1H), 2.35 (d, J=13.6 Hz, 1H), 2.01-1.99 (m, 1H), 1.91-1.85 (m, 1H), 1.70-1.24 (m, 8H), 1.10-1.01 (m, 3H), 0.95-0.90 (m, 2H).

MH+ 342.

Example 69

(+)[N-(Benzyloxycarbonyl)morphinan-3-yloxy]methyl 3-methylbutanoate

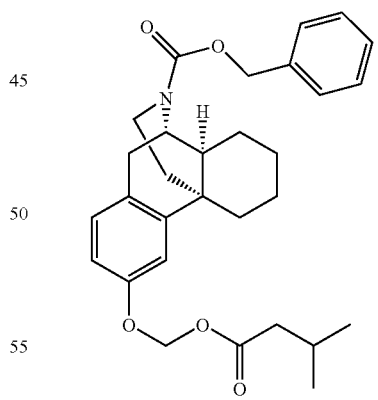

$^1$H NMR (400 MHz, CDCl$_3$) δ 7.34 (br, 5H), 7.01 (d, J=8.4 Hz, 1H), 6.94 (d, J=2.4 Hz, 1H), 6.83 (dd, J=8.4, 2.8 Hz, 1H), 5.75 and 5.73 (AB q, J=6.4 Hz, 2H), 5.13 (br, 2H), 4.40 (br, 1H), 3.88 (br, 1H), 3.09 (br d, J=15.6 Hz, 1H), 2.70-2.59 (m, 2H), 2.33 (d, J=12.4 Hz, 1H), 2.23 (d, J=7.2 Hz, 2H), 2.13-2.06 (m, 1H), 1.71-1.22 (m, 9H), 1.09-1.02 (m, 1H), 0.92 (d, J=6.8 Hz, 6H).

MH+ 492.

Example 70

(+)-(Morphinan-3-yloxy)methyl 3-methylbutanoate TFA

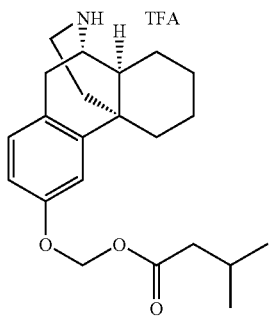

$^1$H NMR (400 MHz, CDCl$_3$) δ 12.86 (br, 1H), 8.48 (br, 1H), 7.10 (d, J=8.8 Hz, 1H), 6.94 (d, J=2.4 Hz, 1H), 6.91 (dd, J=8.4, 2.4 Hz, 1H), 5.74 (s, 2H), 3.71 (br, 1H), 3.23-3.14 (m, 2H), 3.04 (br d, J=19.2 Hz, 1H), 2.78-2.76 (m, 1H), 2.34 (d, J=14.0 Hz, 1H), 2.23 (d, J=7.2 Hz, 2H), 2.13-2.05 (m, 1H), 2.01-2.00 (m, 1H), 1.92-1.85 (m, 1H), 1.69-1.34 (m, 6H), 1.29-1.23 (m, 1H), 1.10-0.97 (m, 1H), 0.92 (d, J=6.8 Hz, 6H). MH+ 358.

Example 71

(+)-[N-(Benzyloxycarbonyl)morphinan-3-yloxy]methyl 2-phenylbutanoate

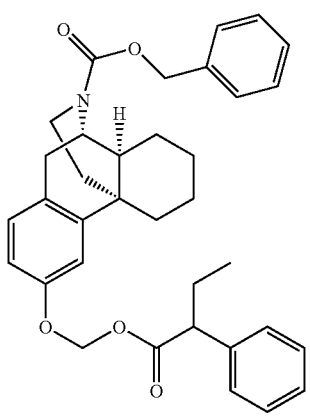

$^1$H NMR (400 MHz, CDCl$_3$) δ 7.42-7.20 (m, 10H), 6.94 (d, J=8.0 Hz, 1H), 6.87 (dd, J=6.8, 2.4 Hz, 1H), 6.71-6.68 (m, 1H), 5.74 and 5.67 (AB q, J=6.8 Hz, 2H), 5.13 (br, 2H), 4.41 (br, 1H), 3.86 (br, 1H), 3.48 (t, J=7.6 Hz, 1H), 3.07 (br d, J=14.4 Hz, 1H), 2.68-2.64 (m, 2H), 2.28-2.22 (m, 1H), 2.15-2.04 (m, 1H), 1.84-1.77 (m, 1H), 1.69-1.20 (m, 8H), 1.00-0.97 (m, 1H), 0.91-0.84 (m, 4H). MH+ 554.

Example 72

(+)-(Morphinan-3-yloxy)methyl 2-phenylbutanoate TFA

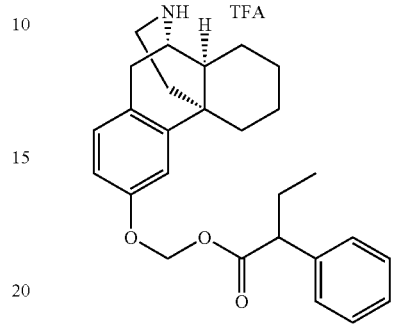

$^1$H NMR (400 MHz, CDCl$_3$) δ 8.54 (br, 1H), 7.52 (br, 1H), 7.27-7.24 (m, 5H), 7.03 (dd, J=8.4, 2.4 Hz, 1H), 6.85 (dd, J=9.2, 2.4 Hz, 1H), 6.78-6.74 (m, 1H), 5.74-5.68 (m, 2H), 3.71 (br, 1H), 3.48 (t, J=7.6 Hz, 1H), 3.21-3.13 (m, 2H), 3.03 (d, J=19.2 Hz, 1H), 2.74 (br, 1H), 2.28-2.23 (m, 1H), 2.16-1.99 (m, 2H), 1.92-1.75 (m, 2H), 1.67 (d, J=11.2 Hz, 1H), 1.54-1.35 (m, 4H), 1.27-1.16 (m, 1H), 1.04-0.96 (m, 2H), 0.88-0.74 (m, 3H). MH+ 420.

Example 73

(+)-[N-(Benzyloxycarbonyl)morphinan-3-yloxy]methyl 1-adamantanecarboxylate

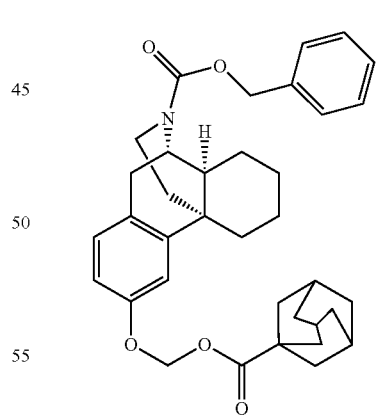

$^1$H NMR (400 MHz, CDCl$_3$) δ 7.30 (br, 5H), 6.99 (d, J=6.0 Hz, 1H), 6.96 (d, J=2.4 Hz, 1H), 6.82 (dd, J=8.4, 2.4 Hz, 1H), 5.76 and 5.68 (Ab q, J=6.4 Hz, 2H), 5.12 (br, 2H), 4.41 (br, 1H), 3.86 (br, 1H), 3.09 (br, 1H), 2.70-2.65 (m, 2H), 2.34 (d, J=13.2 Hz, 1H), 1.99 (br, 1H), 1.88 (d, J=2.4 Hz, 6H), 1.73-1.64 (m, 8H), 1.58-1.50 (m, 5H), 1.35-1.23 (m, 4H), 1.09-1.03 (m, 1H). MH+ 570.

Example 74

(+)-(Morphinan-3-yloxy)methyl 1-adamantanecarboxylate TFA

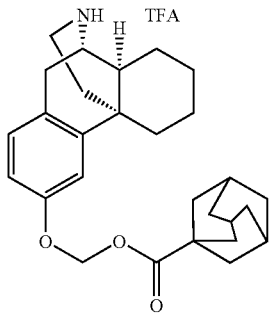

¹H NMR (400 MHz, CDCl₃) δ 9.93 (br, 1H), 8.50 (br, 1H), 7.11 (d, J=8.4 Hz, 1H), 6.96 (d, J=2.4 Hz, 1H), 6.90 (dd, J=8.4, 2.4 Hz, 1H), 5.76 and 5.67 (AB q, J=6.4 Hz, 2H), 3.71 (br, 1H), 3.24-3.14 (m, 2H), 3.04 (br d, J=19.2 Hz, 1H), 2.78-2.76 (m, 1H), 2.35 (d, J=14.0 Hz, 1H), 2.00 (br, 1H), 1.95-1.87 (m, 8H), 1.73-1.64 (m, 8H), 1.57-1.25 (m, 7H), 1.11-1.02 (m, 1H).

MH+ 436.

Example 75

(+)-(Morphinan-3-yloxy)methyl acetate TFA

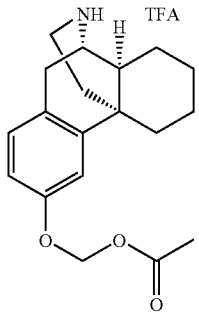

¹H NMR (400 MHz, CDCl₃) δ 9.00 (br, 1H), 7.13 (d, J=8.4 Hz, 1H), 6.95 (d, J=2.8 Hz, 1H), 6.92 (dd, J=8.4, 2.8 Hz, 1H), 5.77 and 5.73 (AB q, J=6.4 Hz, 2H), 4.00 (br, 1H), 3.67 (br, 1H), 3.24-3.07 (m, 3H), 2.85-2.76 (m, 1H), 2.36 (d, J=13.2 Hz, 2H), 2.13 (s, 3H), 2.09-2.04 (m, 1H), 1.96-1.88 (m, 1H), 1.68 (d, J=12.4 Hz, 1H), 1.60-1.37 (m, 4H), 1.31-1.25 (m, 1H), 1.12-1.03 (m, 1H).

MH+ 316.

Example 76

(+)-(Morphinan-3-yloxy)methyl 3-cylcohexylpropanoate TFA

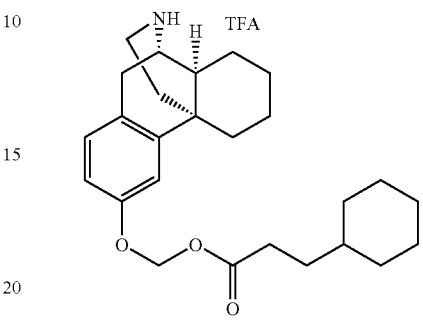

¹H NMR (400 MHz, CDCl₃) δ 9.06 (br, 1H), 7.12 (d, J=8.4 Hz, 1H), 6.95 (d, J=2.4 Hz, 1H), 6.92 (dd, J=8.4, 2.4 Hz, 1H), 5.77 and 5.74 (AB q, J=6.4 Hz, 2H), 5.39 (br, 1H), 3.66 (br, 1H), 3.23-3.07 (m, 3H), 2.78-2.75 (m, 1H), 2.39-2.34 (m, 3H), 2.05 (d, J=12.4 Hz, 1H), 1.95-1.87 (m, 1H), 1.77-1.37 (m, 13H), 1.31-1.04 (m, 7H), 0.90-0.82 (m, 1H).

MH+ 412.

Example 77

(+)-[N-(Benzyloxycarbonyl)morphinan-3-yloxy]methyl 3,5,5-trimethylhexanoate

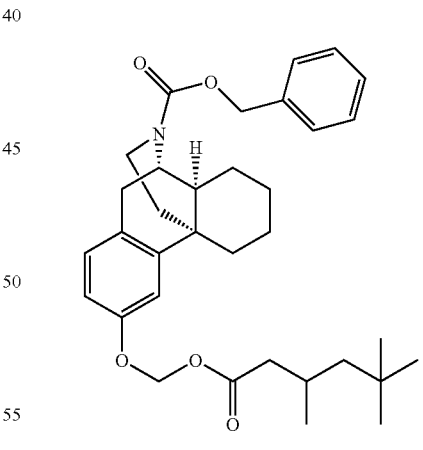

¹H NMR (400 MHz, CDCl₃) δ 7.39-7.28 (m, 5H), 7.02 (t, J=8.8 Hz, 1H), 6.95 (s, 1H), 6.85 (dd, J=8.4, 2.0 Hz, 1H), 5.79-5.71 (m, 2H), 5.20-5.09 (m, 2H), 4.37 (br d, J=42.8 Hz, 1H), 3.96-3.83 (m, 1H), 3.14-3.05 (m, 1H), 2.73-2.57 (m, 2H), 2.38-2.33 (m, 2H), 2.20-2.15 (m, 1H), 2.08-2.00 (m, 1H), 1.72-1.20 (m, 10H), 1.12-1.02 (m, 2H), 0.95 (d, J=6.4 Hz, 3H), 0.86 (s, 9H).

MH+ 548.

Example 78

(+)-(Morphinan-3-yloxy)methyl 3,5,5-trimethylhexanoate TFA

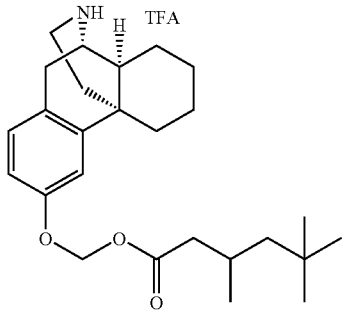

$^1$H NMR (400 MHz, CDCl$_3$) δ 9.63 (br, 1H), 8.84 (br, 1H), 7.12 (d, J=8.4 Hz, 1H), 6.96 (d, J=2.4 Hz, 1H), 6.93 (dd, J=8.4, 2.4 Hz, 1H), 5.79-5.72 (m, 2H), 3.68 (br, 1H), 3.24-3.05 (m, 3H), 2.82-2.73 (m, 1H), 2.38-2.34 (m, 2H), 2.22-2.16 (m, 1H), 2.05-2.02 (m, 1H), 1.92-1.86 (m, 1H), 1.68 (d, J=12.8 Hz, 1H), 1.60-1.21 (m, 8H), 1.13-1.01 (m, 2H), 0.96 (d, J=6.4 Hz, 3H), 0.87 (s, 9H).
MH+ 414.

Example 79

(+)-Isopropyl(morphinan-3-yloxy)methyl carbonate TFA

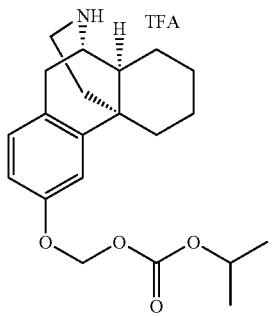

(+)-Isopropyl [(benzyloxycarbonyl)morphinan-3-yloxy] methyl carbonate (16.9 g, 34.2 mmol) from Example 1 was subjected to hydrogenation (balloon) on 10% Pd/C (1.7 g) in 1,4-dioxane (100 mL) at room temperature. After the reaction was completed, the reaction mixture was filtered through a Celite, and washed with 1,4-dioxane (50 mL). The combined 1,4-dioxane solution was evaporated under vacuum. The residue was further purified by prep reverse-phase HPLC with 0.1% TFA to provide the title compound (8.86 g, 55%) as a colorless gum.

$^1$H NMR (400 MHz, CDCl$_3$) δ 9.11 (br, 2H), 7.12 (d, J=8.4 Hz, 1H), 6.95-6.93 (m, 2H), 5.76 and 5.70 (AB q, J=6.4 Hz, 2H), 4.95-4.89 (m, 1H), 3.68 (br, 1H), 3.23-3.11 (m, 3H), 2.75 (br, 1H), 2.35 (d, J=13.6 Hz, 1H), 2.08 (d, J=12.0 Hz, 1H), 1.98-1.90 (m, 1H), 1.66 (d, J=12.8 Hz, 1H), 1.58-1.37 (m, 5H), 1.30 (d, J=6.0 Hz, 6H), 1.27-1.24 (m, 1H), 1.07-1.03 (m, 1H).
MH+ 360.

Example 80

(+)-Isopropyl(morphinan-3-yloxy)methyl carbonate L-(+)-tartaric acid

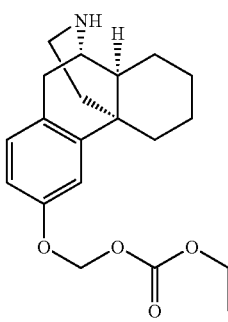 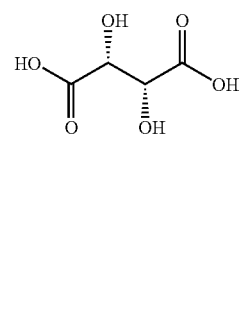

Method 1: (+)-Isopropyl(morphinan-3-yloxy)methyl carbonate TFA (300 mg, 0.634 mmol) from Example 79 was dissolved in EtOAc (20 mL) and washed with saturated NaHCO$_3$ solution (20 mL×2). To the EtOAc layer was added L-(+)-tartaric acid (95.2 mg, 0.634 mmol). The mixture was stirred at 40° C. for 10 min. and cooled to room temperature. The precipitated solution was filtered and washed with EtOAc (10 mL) to provide the title compound (268 mg, 83%) as a white solid.

Method 2: (+)-Isopropyl[N-(benzyloxycarbonyl)morphinan-3-yloxy]methyl carbonate (1.72 g, 3.48 mmol) from Example 1 was subjected to hydrogenation (balloon) on 10% Pd/C (170 mg) in IPA (25 mL) at room temperature. After the reaction was completed, the reaction mixture was filtered through a Celite, and washed with IPA (20 mL). To the combined IPA solution was added L-(+)-tartaric acid (522 mg, 3.48 mmol). The mixture was stirred at 40° C. for 30 min. The mixture was evaporated under vacuum. To the residue was added EtOAc (20 mL). The solution was filtered and washed with EtOAc (10 mL) to provide the title compound (1.61 g, 91%) as a white solid.

[α]$_D^{27}$+24.0° (c=1.0, MeOH); mp 159° C.; IR (KBr) ν$_{max}$ 3525, 3179, 2933, 2456, 1760, 1455, 1431, 1271, 1219, 1043 cm$^{-1}$; $^1$H NMR (400 MHz, CD$_3$OD) δ 7.18 (d, J=8.4 Hz, 1H), 7.03 (d, J=2.4 Hz, 1H), 6.95 (dd, J=8.4, 2.4 Hz, 1H), 5.75 and 5.72 (AB q, J=6.8 Hz, 2H), 4.89-4.82 (m, 1H), 4.39 (s, 2H), 3.70-3.68 (m, 1H), 3.25 (d, J=6.0 Hz, 1H), 3.11 (dd, J=13.6, 4.0 Hz, 1H), 2.99 (br d, J=18.8 Hz, 1H), 2.74-2.66 (m, 1H), 2.45 (d, J=14.4 Hz, 1H), 1.96 (d, J=11.6 Hz, 1H), 1.88-1.80 (m, 1H), 1.70 (d, J=12.8 Hz, 1H), 1.59-1.42 (m, 5H), 1.34-1.28 (m, 1H), 1.26 (d, J=6.4 Hz, 6H), 1.14-1.04 (m, 1H); $^{13}$C NMR (400 MHz, CD$_3$OD) δ 176.1, 156.5, 153.9, 139.5, 129.4, 128.9, 114.8, 113.5, 88.4, 73.1, 72.5, 51.3, 41.2, 38.4, 37.6, 36.6, 35.5, 27.7, 25.9, 25.6, 21.7, 20.7; HR-FAB-MS m/z: 360.2173 [M+H]$^+$ (Calcd for C$_{21}$H$_{30}$NO$_4$: 360.2175).
MH+ 360.

The following compounds of Examples 81 to 92 were obtained by repeating the procedure of Example 80.

Example 81

(+)-Isopropyl(morphinan-3-yloxy)methyl carbonate HCl

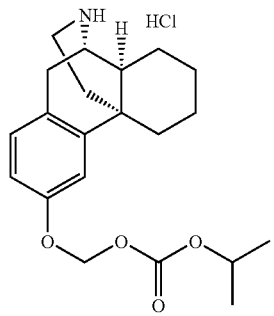

$^1$H NMR (400 MHz, CDCl$_3$) δ 9.62 (br, 2H), 7.12 (d, J=8.4 Hz, 1H), 6.95-6.92 (m, 2H), 5.76 and 5.70 (AB q, J=6.4 Hz, 2H), 4.95-4.89 (m, 1H), 3.72 (br, 1H), 3.26-3.14 (m, 3H), 2.73 (br, 1H), 2.33 (d, J=12.4 Hz, 1H), 2.16 (d, J=12.0 Hz, 1H), 2.03-1.98 (m, 1H), 1.65 (d, J=10.8 Hz, 1H), 1.57-1.36 (m, 5H), 1.30 (d, J=6.4 Hz, 6H), 1.26-1.22 (m, 1H), 1.06-1.03 (m, 1H).

MH+ 360.

Example 82

(+)-Isopropyl(morphinan-3-yloxy)methyl carbonate formic acid

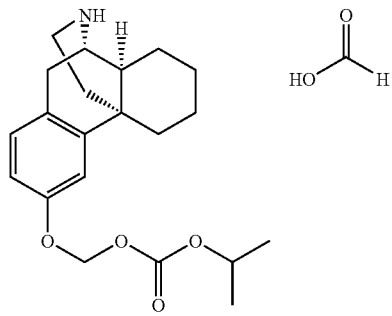

$^1$H NMR (400 MHz, CD$_3$OD) δ 8.51 (s, 1H), 7.18 (d, J=8.4 Hz, 1H), 7.03 (d, J=2.4 Hz, 1H), 6.96 (dd, J=8.4, 2.4 Hz, 1H), 5.75 and 5.72 (AB q, J=6.4 Hz, 2H), 4.93-4.82 (m, 1H), 3.69-3.67 (m, 1H), 3.32-3.25 (m, 1H), 3.12-3.07 (m, 1H), 2.97 (br d, J=19.2 Hz, 1H), 2.75-2.67 (m, 1H), 2.46 (br d, J=17.2 Hz, 1H), 1.96-1.92 (m, 1H), 1.86-1.78 (m, 1H), 1.71 (d, J=14.4 Hz, 1H), 1.61-1.38 (m, 5H), 1.33-1.29 (m, 1H), 1.26 (d, J=6.0 Hz, 6H), 1.14-1.04 (m, 1H).

MH+ 360.

Example 83

(+)-Isopropyl(morphinan-3-yloxy)methyl carbonate citric acid

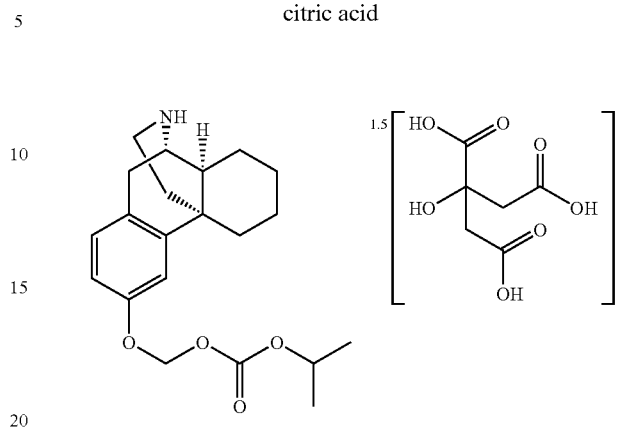

$^1$H NMR (400 MHz, CD$_3$OD) δ 7.18 (d, J=8.4 Hz, 1H), 7.03 (d, J=2.4 Hz, 1H), 6.96 (dd, J=8.4, 2.4 Hz, 1H), 5.75 and 5.72 (AB q, J=6.8 Hz, 2H), 4.88-4.83 (m, 1H), 3.71-3.68 (m, 1H), 3.25 (d, J=6.8 Hz, 1H), 3.13-3.09 (m, 1H), 2.98 (br d, J=19.2 Hz, 1H), 2.86-2.68 (m, 7H), 2.45 (d, J=13.6 Hz, 1H), 1.97-1.94 (m, 1H), 1.87-1.79 (m, 1H), 1.71 (d, J=13.6 Hz, 1H), 1.60-1.40 (m, 5H), 1.34-1.28 (m, 1H), 1.26 (d, J=6.4 Hz, 6H), 1.14-1.04 (m, 1H).

MH+ 360.

Example 84

(+)-Isopropyl(morphinan-3-yloxy)methyl carbonate fumaric acid

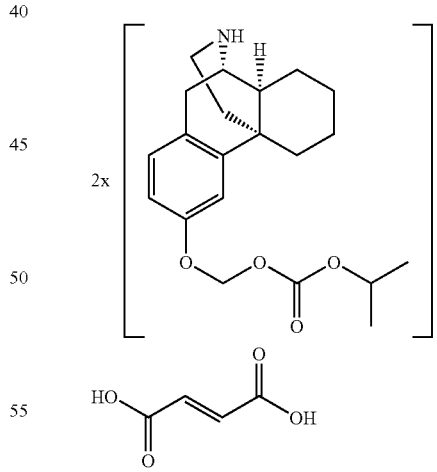

$^1$H NMR (400 MHz, CD$_3$OD) δ 7.18 (d, J=8.4 Hz, 1H), 7.03 (s, 1H), 6.96 (d, J=8.4 Hz, 1H), 6.66 (s, 1H), 5.75 and 5.72 (AB q, J=6.8 Hz, 2H), 4.89-4.86 (m, 1H), 3.69-3.67 (m, 1H), 3.12-3.08 (m, 1H), 3.00-2.95 (m, 1H), 2.74-2.68 (m, 1H), 2.45 (d, J=13.6 Hz, 1H), 1.97-1.93 (m, 1H), 1.84-1.80 (m, 1H), 1.75-1.66 (m, 1H), 1.60-1.32 (m, 6H), 1.26 (d, J=6.0 Hz, 6H), 1.18-1.05 (m, 2H).

MH+ 360.

Example 85

(+)-Isopropyl(morphinan-3-yloxy)methyl carbonate fumaric acid mono-Na

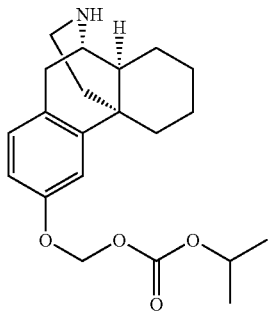 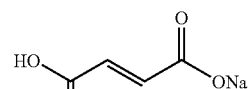

¹H NMR (400 MHz, CD₃OD) δ 7.26 (d, J=8.4 Hz, 1H), 7.03 (s, 1H), 6.96 (d, J=8.4 Hz, 1H), 6.66 (s, 2H), 5.75 and 5.72 (AB q, J=6.8 Hz, 2H), 4.93-4.86 (m, 1H), 3.69-3.67 (m, 1H), 3.12-3.08 (m, 1H), 2.99-2.94 (m, 1H), 2.75-2.67 (m, 1H), 2.45 (d, J=14.4 Hz, 1H), 1.96-1.93 (m, 1H), 1.86-1.78 (m, 1H), 1.75-1.67 (m, 1H), 1.61-1.30 (m, 6H), 1.26 (d, J=6.0 Hz, 6H), 1.18-1.10 (m, 2H).

MH+ 360.

Example 86

(+)-Isopropyl(morphinan-3-yloxy)methyl carbonate 4-methylbenzenesulfonic acid

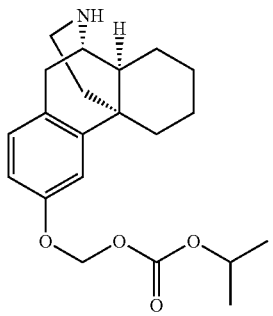 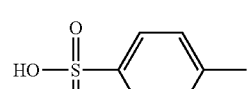

¹H NMR (400 MHz, CD₃OD) δ 7.70 (d, J=8.4 Hz, 2H), 7.23 (d, J=7.6 Hz, 2H), 7.17 (d, J=8.4 Hz, 1H), 7.02 (d, J=2.4 Hz, 1H), 6.95 (dd, J=8.4, 2.8 Hz, 1H), 5.76 and 5.72 (AB q, J=6.8 Hz, 2H), 4.89-4.83 (m, 1H), 3.68-3.66 (m, 1H), 3.24 (d, J=6.4 Hz, 1H), 3.11-3.07 (m, 1H), 2.95 (br d, J=19.2 Hz, 1H), 2.75-2.67 (m, 1H), 2.44 (d, J=13.6 Hz, 1H), 1.94-1.90 (m, 1H), 1.85-1.77 (m, 1H), 1.69 (d, J=14.0 Hz, 1H), 1.59-1.28 (m, 6H), 1.24 (d, J=8.0 Hz, 6H), 1.08-1.04 (m, 1H).

MH+ 360.

Example 87

(+)-Isopropyl(morphinan-3-yloxy)methyl carbonate stearic acid

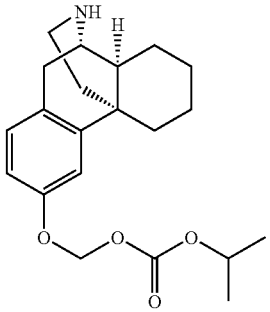 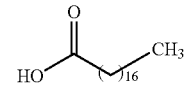

¹H NMR (400 MHz, CD₃OD) δ 7.18 (d, J=8.8 Hz, 1H), 7.03 (d, J=2.4 Hz, 1H), 6.96 (dd, J=8.4, 2.4 Hz, 1H), 5.76 and 5.73 (AB q, J=7.2 Hz, 2H), 4.88-4.83 (m, 1H), 3.68-3.66 (m, 1H), 3.26 (d, J=6.4 Hz, 1H), 3.09 (dd, J=13.6, 3.6 Hz, 1H), 2.96 (br d, J=19.2 Hz, 1H), 2.74-2.67 (m, 1H), 2.46 (d, J=14.0 Hz, 1H), 2.18 (t, J=7.6 Hz, 2H), 1.95-1.91 (m, 1H), 1.86-1.78 (m, 1H), 1.71 (d, J=13.2 Hz, 1H), 1.60-1.39 (m, 6H), 1.33-1.22 (m, 36H), 1.14-1.07 (m, 1H), 0.89 (t, J=6.8 Hz, 3H).

MH+ 360.

Example 88

(+)-Isopropyl(morphinan-3-yloxy)methyl carbonate citric acid di-Na

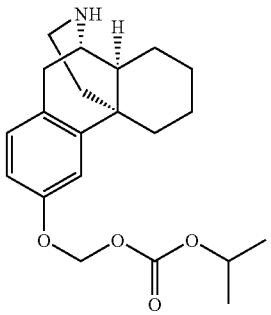 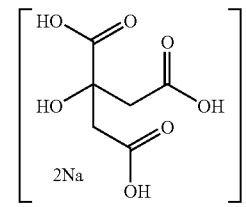

¹H NMR (400 MHz, D₂O) δ 7.21 (d, J=8.4 Hz, 1H), 7.00 (s, 1H), 6.95 (d, J=8.4 Hz, 1H), 5.76 and 5.72 (AB q, J=6.8 Hz, 2H), 4.92-4.81 (m, 1H), 3.71 (m, 1H), 3.30 (s, 4H), 3.24-3.23 (m, 1H), 3.16-3.12 (m, 1H), 3.04-2.99 (m, 1H), 2.71-2.64 (m, 1H), 2.40 (d, J=13.6 Hz, 1H), 2.01-1.97 (m, 1H), 1.91-1.83 (m, 1H), 1.68-1.65 (m, 1H), 1.58-1.38 (m, 5H), 1.26 (d, J=6.4 Hz, 6H), 1.19-0.97 (m, 2H).

MH+ 360.

Example 89

(+)-Isopropyl(morphinan-3-yloxy)methyl carbonate
L-(−)-malic acid

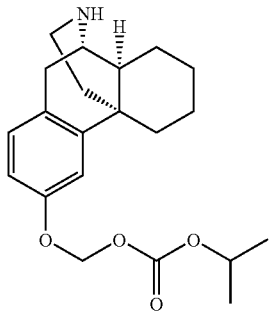 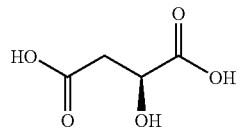

$^1$H NMR (400 MHz, CD$_3$OD) δ 7.18 (d, J=8.4 Hz, 1H), 7.03 (d, J=2.8 Hz, 1H), 6.96 (dd, J=8.4, 2.8 Hz, 1H), 5.76 and 5.73 (AB q, J=6.8 Hz, 2H), 4.89-4.83 (m, 1H), 4.31 (dd, J=10.0, 5.2 Hz, 1H), 3.70-3.68 (m, 1H), 3.26 (d, J=6.0 Hz, 1H), 3.10 (dd, J=12.8, 4.0 Hz, 1H), 2.97 (br d, J=19.2 Hz, 1H), 2.81-2.67 (m, 2H), 2.55-2.51 (m, 1H), 2.45 (d, J=14.0 Hz, 1H), 1.95 (d, J=12.4 Hz, 1H), 1.87-1.78 (m, 1H), 1.71 (d, J=12.8 Hz, 1H), 1.60-1.39 (m, 5H), 1.34-1.28 (m, 1H), 1.26 (d, J=6.0 Hz, 6H), 1.15-1.06 (m, 1H).

MH+ 360.

Example 90

(+)-Isopropyl(morphinan-3-yloxy)methyl carbonate
L-(+)-lactic acid

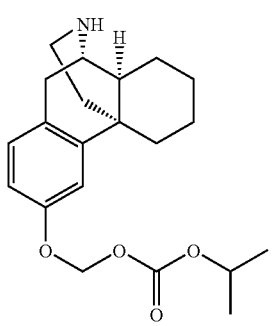 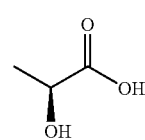

$^1$H NMR (400 MHz, CD$_3$OD) δ 7.18 (d, J=8.4 Hz, 1H), 7.04 (d, J=2.4 Hz, 1H), 6.96 (dd, J=8.4, 2.4 Hz, 1H), 5.76 and 5.73 (AB q, J=6.8 Hz, 2H), 4.88-4.84 (m, 1H), 4.05 (q, J=6.8 Hz, 1H), 3.69-3.67 (m, 1H), 3.32-3.26 (m, 1H), 3.10 (dd, J=13.2, 3.2 Hz, 1H), 2.96 (br d, J=19.2 Hz, 1H), 2.75-2.67 (m, 1H), 2.46 (d, J=14.0 Hz, 1H), 1.93 (d, J=12.4 Hz, 1H), 1.86-1.78 (m, 1H), 1.71 (d, J=12.8 Hz, 1H), 1.60-1.39 (m, 5H), 1.34-1.28 (m, 4H), 1.26 (d, J=6.0 Hz, 6H), 1.15-1.07 (m, 1H).

MH+ 360.

Example 91

(+)-Isopropyl(morphinan-3-yloxy)methyl carbonate
succinic acid

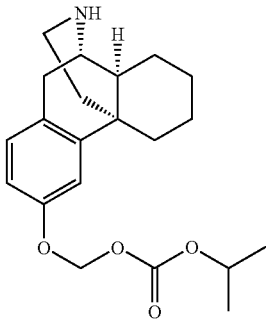 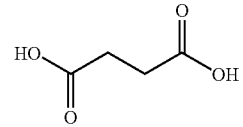

$^1$H NMR (400 MHz, CD$_3$OD) δ 7.18 (d, J=8.4 Hz, 1H), 7.03 (d, J=2.4 Hz, 1H), 6.96 (dd, J=8.4, 2.4 Hz, 1H), 5.76 and 5.72 (AB q, J=6.8 Hz, 2H), 4.90-4.82 (m, 1H), 3.66 (br, 1H), 3.32-3.29 (m, 1H), 3.08 (dd, J=12.8, 3.6 Hz, 1H), 2.95 (br d, J=19.2 Hz, 1H), 2.75-2.68 (m, 1H), 2.50 (s, 4H), 2.49-2.44 (m, 1H), 1.92 (d, J=11.2 Hz, 1H), 1.84-1.78 (m, 1H), 1.71 (d, J=13.6 Hz, 1H), 1.60-1.39 (m, 5H), 1.34-1.29 (m, 1H), 1.26 (d, J=6.0 Hz, 6H), 1.14-1.05 (m, 1H).

MH+ 360.

Example 92

(+)-Isopropyl(morphinan-3-yloxy)methyl carbonate
salicylic acid

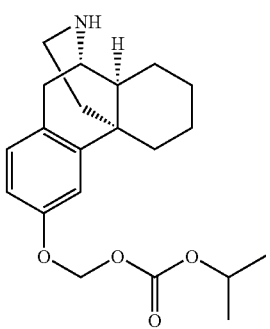 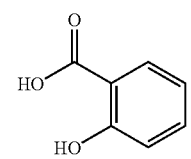

$^1$H NMR (400 MHz, CD$_3$OD) δ 7.82 (dd, J=8.0, 2.4 Hz, 1H), 7.32-7.27 (m, 1H), 7.17 (d, J=8.4 Hz, 1H), 7.03 (d, J=2.8 Hz, 1H), 6.95 (dd, J=8.4, 2.8 Hz, 1H), 5.75 and 5.72 (AB q, J=6.8 Hz, 2H), 4.89-4.83 (m, 1H), 3.70-3.68 (m, 1H), 3.26 (d, J=6.0 Hz, 1H), 3.10 (dd, J=12.8, 3.6 Hz, 1H), 2.96 (br d, J=19.2 Hz, 1H), 2.74-2.68 (m, 1H), 2.45 (d, J=13.6 Hz, 1H), 1.95-1.91 (m, 1H), 1.85-1.77 (m, 1H), 1.69 (d, J=10.8 Hz, 1H), 1.59-1.28 (m, 6H), 1.26 (d, J=6.4 Hz, 6H), 1.13-1.06 (m, 1H).

MH+ 360.

Example 93

(+)-(Morphinan-3-yloxy)methyl pivalate succinic acid

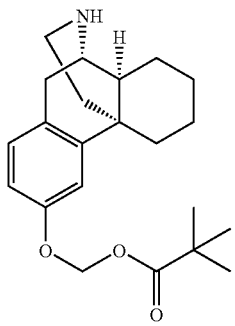
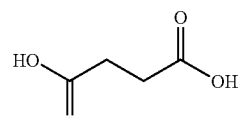

(+)-(Morphinan-3-yloxy)methyl pivalate trifluoroacetic acid salt (240 mg, 0.509 mmol) from Example 62 was dissolved in EtOAc (20 mL) and washed with saturated NaHCO$_3$ solution (20 mL×2). To the EtOAc layer was added succinic acid (60.1 mg, 0.509 mmol). The mixture was stirred at 40° C. for 10 min. and cooled to room temperature. The precipitated solution was filtered and washed with EtOAc (10 mL) to provide the title compound (243 mg, 100%) as a white solid.

$^1$H NMR (400 MHz, CD$_3$OD) δ 7.18 (d, J=8.4 Hz, 1H), 7.05 (d, J=2.0 Hz, 1H), 6.94 (dd, J=8.4, 2.4 Hz, 1H), 5.79 and 5.73 (AB q, J=6.8 Hz, 2H), 3.69-3.67 (m, 1H), 3.25 (d, J=6.4 Hz, 1H), 3.10 (dd, J=13.2, 3.6 Hz, 1H), 2.97 (br d, J=19.2 Hz, 1H), 2.72-2.65 (m, 1H), 2.50 (s, 4H), 2.45 (d, J=13.6 Hz, 1H), 1.95 (d, J=12.4 Hz, 1H), 1.87-1.79 (m, 1H), 1.70 (d, J=12.4 Hz, 1H), 1.58-1.38 (m, 4H), 1.34-1.21 (m, 2H), 1.17 (s, 9H), 1.10-1.04 (m, 1H).

MH+ 358.

The following compounds of Examples 94 to 105 were obtained by repeating the procedure of Example 93.

Example 94

(+)-(Morphinan-3-yloxy)methyl pivalate HCl

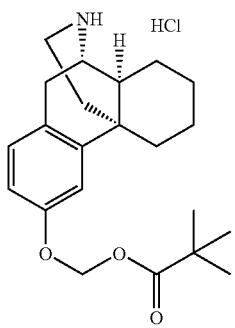

$^1$H NMR (400 MHz, CD$_3$OD) δ 7.19 (d, J=8.4 Hz, 1H), 7.04 (br, 1H), 6.93 (d, J=7.2 Hz, 1H), 5.79 and 5.73 (AB q, J=6.4 Hz, 2H), 3.72 (br, 1H), 3.30-3.25 (m, 1H), 3.13 (d, J=9.6 Hz, 1H), 3.06 (br d, J=19.2 Hz, 1H), 2.73-2.66 (m, 1H), 2.44 (d, J=14.0 Hz, 1H), 2.04 (d, J=12.8 Hz, 1H), 1.95-1.87 (m, 1H), 1.68 (d, J=11.2 Hz, 1H), 1.58-1.38 (m, 5H), 1.32-1.21 (m, 1H), 1.16 (s, 9H), 1.12-1.05 (m, 1H).

MH+ 358.

Example 95

(+)-(Morphinan-3-yloxy)methyl pivalate formic acid

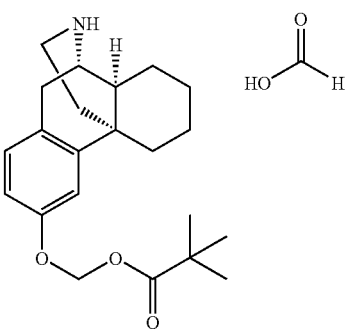

$^1$H NMR (400 MHz, CD$_3$OD) δ 8.30 (s, 1H), 7.18 (d, J=8.4 Hz, 1H), 7.05 (d, J=2.4 Hz, 1H), 6.95 (dd, J=8.4, 2.4 Hz, 1H), 5.79 and 5.73 (AB q, J=6.8 Hz, 2H), 3.70-3.67 (m, 1H), 3.32-3.25 (m, 1H), 3.10 (dd, J=13.2, 3.2 Hz, 1H), 2.96 (br d, J=19.2 Hz, 1H), 2.73-2.66 (m, 1H), 2.46 (d, J=14.0 Hz, 1H), 1.94 (d, J=12.4 Hz, 1H), 1.87-1.78 (m, 1H), 1.68 (d, J=11.2 Hz, 1H), 1.60-1.40 (m, 5H), 1.29-1.21 (m, 1H), 1.17 (s, 9H), 1.12-1.06 (m, 1H).

MH+ 358.

Example 96

(+)-(Morphinan-3-yloxy)methyl pivalate citric acid

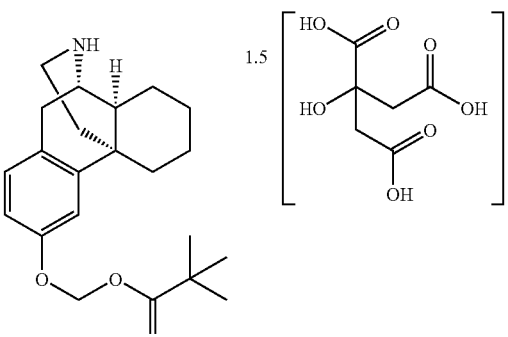

$^1$H NMR (400 MHz, CD$_3$OD) δ 7.18 (d, J=8.4 Hz, 1H), 7.05 (d, J=2.4 Hz, 1H), 6.94 (dd, J=8.4, 2.4 Hz, 1H), 5.79 and 5.73 (AB q, J=6.8 Hz, 2H), 3.69 (br, 1H), 3.30-3.20 (m, 1H), 3.11 (dd, J=13.2, 3.2 Hz, 1H), 2.98 (br d, J=19.2 Hz, 1H), 2.82-2.65 (m, 7H), 2.45 (d, J=14.0 Hz, 1H), 1.96 (d, J=12.0 Hz, 1H), 1.88-1.80 (m, 1H), 1.70 (d, J=12.8 Hz, 1H), 1.58-1.40 (m, 4H), 1.32-1.21 (m, 2H), 1.17 (s, 9H), 1.11-1.06 (m, 1H).

MH+ 358.

Example 97

(+)-(Morphinan-3-yloxy)methyl pivalate fumaric acid

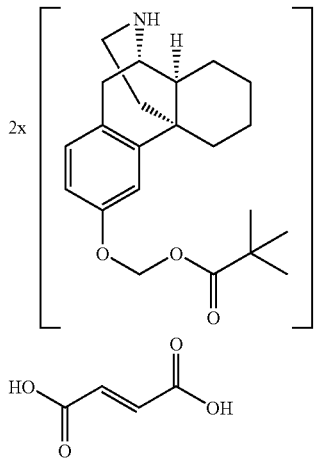

¹H NMR (400 MHz, CD₃OD) δ 7.18 (d, J=8.4 Hz, 1H), 7.05 (d, J=2.4 Hz, 1H), 6.95 (dd, J=8.4, 2.4 Hz, 1H), 6.67 (s, 1H), 5.79 and 5.73 (AB q, J=6.8 Hz, 2H), 3.70-3.67 (m, 1H), 3.32-3.26 (m, 1H), 3.10 (dd, J=13.6, 3.6 Hz, 1H), 2.96 (br d, J=19.2 Hz, 1H), 2.73-2.66 (m, 1H), 2.46 (d, J=13.6 Hz, 1H), 1.94 (d, J=12.4 Hz, 1H), 1.87-1.79 (m, 1H), 1.71 (d, J=13.6 Hz, 1H), 1.60-1.41 (m, 5H), 1.32-1.26 (m, 1H), 1.17 (s, 9H), 1.14-1.07 (m, 1H).

MH+ 358.

Example 98

(+)-(Morphinan-3-yloxy)methyl pivalate fumaric acid mono-Na

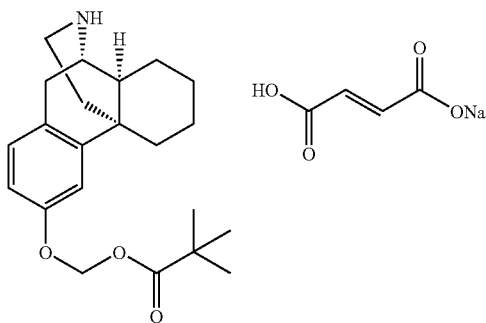

¹H NMR (400 MHz, CD₃OD) δ 7.16 (d, J=8.4 Hz, 1H), 7.04 (d, J=2.4 Hz, 1H), 6.92 (dd, J=8.8, 2.4 Hz, 1H), 6.65 (s, 2H), 5.79 and 5.73 (AB q, J=6.8 Hz, 2H), 3.56-3.55 (m, 1H), 3.29-3.22 (m, 1H), 3.01 (dd, J=13.6, 3.2 Hz, 1H), 2.92 (br d, J=18.8 Hz, 1H), 2.69-2.62 (m, 1H), 2.43 (d, J=13.6 Hz, 1H), 1.91 (d, J=12.4 Hz, 1H), 1.83-1.75 (m, 1H), 1.70 (d, J=10.8 Hz, 1H), 1.58-1.39 (m, 4H), 1.32-1.21 (m, 2H), 1.17 (s, 9H), 1.10-1.04 (m, 1H).

MH+ 358.

Example 99

(+)-(Morphinan-3-yloxy)methyl pivalate 4-methylbenzenesulfonic acid

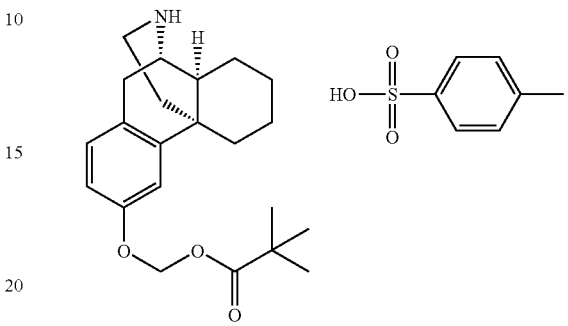

¹H NMR (400 MHz, CD₃OD) δ 7.72 (d, J=8.0 Hz, 2H), 7.22 (d, J=8.0 Hz, 2H), 7.10 (d, J=8.4 Hz, 1H), 6.99 (d, J=2.4 Hz, 1H), 6.87 (dd, J=8.4, 2.4 Hz, 1H), 5.77 and 5.71 (AB q, J=6.4 Hz, 2H), 3.38-3.36 (m, 1H), 3.14 (dd, J=18.8, 6.4 Hz, 1H), 2.91-2.85 (m, 2H), 2.61-2.53 (m, 1H), 2.37-2.34 (m, 4H), 1.87-1.84 (m, 1H), 1.76-1.69 (m, 1H), 1.62 (d, J=11.6 Hz, 1H), 1.51 (d, J=12.0 Hz, 1H), 1.40-1.32 (m, 4H), 1.28-1.19 (m, 1H), 1.16 (s, 9H), 1.02-0.98 (m, 1H).

MH+ 358.

Example 100

(+)-(Morphinan-3-yloxy)methyl pivalate stearic acid

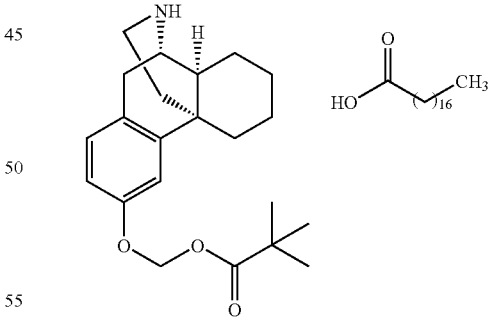

¹H NMR (400 MHz, CD₃OD) δ 7.13 (d, J=8.4 Hz, 1H), 7.01 (d, J=2.4 Hz, 1H), 6.89 (dd, J=8.4, 2.4 Hz, 1H), 5.78 and 5.72 (AB q, J=6.8 Hz, 2H), 3.37-3.36 (m, 1H), 3.23-3.17 (m, 1H), 2.89-2.85 (m, 2H), 2.64-2.56 (m, 1H), 2.40 (d, J=13.6 Hz, 1H), 2.14 (t, J=7.6 Hz, 2H), 1.88-1.84 (m, 1H), 1.77-1.21 (m, 38H), 1.17 (s, 9H), 1.12-1.04 (m, 1H), 0.89 (t, J=7.2 Hz, 3H).

MH+ 358.

Example 101

(+)-(Morphinan-3-yloxy)methyl pivalate citric acid di-Na

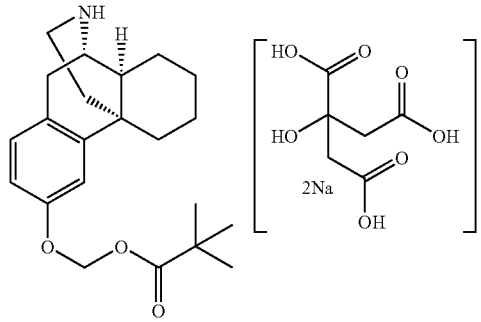

$^1$H NMR (400 MHz, CD$_3$OD) δ 7.13 (d, J=8.4 Hz, 1H), 7.01 (d, J=2.4 Hz, 1H), 6.98 (dd, J=8.4, 2.4 Hz, 1H), 5.78 and 5.72 (AB q, J=6.8 Hz, 2H), 3.41-3.39 (m, 1H), 3.30 (s, 4H), 3.20 (dd, J=18.8, 6.0 Hz, 1H), 2.92-2.86 (m, 2H), 2.64-2.57 (m, 1H), 2.40 (d, J=13.6 Hz, 1H), 1.88-1.85 (m, 1H), 1.77-1.67 (m, 2H), 1.57-1.21 (m, 6H), 1.17 (s, 9H), 1.12-1.04 (m, 1H).

MH+ 358.

Example 102

(+)-(Morphinan-3-yloxy)methyl pivalate L-(+)-tartaric acid

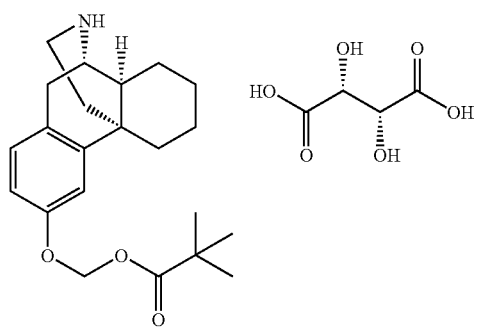

$^1$H NMR (400 MHz, CD$_3$OD) δ 7.18 (d, J=8.0 Hz, 1H), 7.04 (d, J=2.0 Hz, 1H), 6.93 (dd, J=8.4, 2.4 Hz, 1H), 5.79 and 5.73 (AB q, J=6.8 Hz, 2H), 4.32 (s, 2H), 3.68 (br, 1H), 3.29-3.22 (m, 1H), 3.12-3.08 (m, 1H), 2.99 (br d, J=19.2 Hz, 1H), 2.70-2.63 (m, 1H), 2.44 (d, J=13.6 Hz, 1H), 2.00-1.96 (m, 1H), 1.89-1.81 (m, 1H), 1.70 (d, J=13.6 Hz, 1H), 1.59-1.40 (m, 4H), 1.32-1.21 (m, 2H), 1.17 (s, 9H), 1.13-1.06 (m, 1H).

MH+ 358.

Example 103

(+)-(Morphinan-3-yloxy)methyl pivalate L-(−)-malic acid

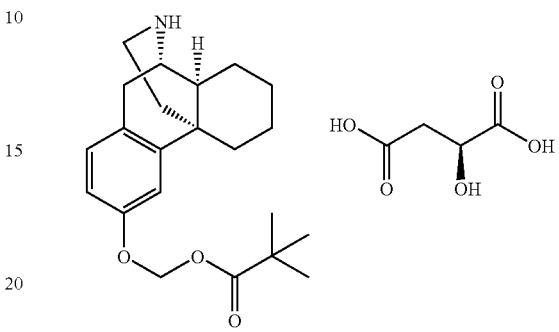

$^1$H NMR (400 MHz, CD$_3$OD) δ 7.18 (d, J=8.4 Hz, 1H), 7.05 (d, J=2.4 Hz, 1H), 6.94 (dd, J=8.4, 2.4 Hz, 1H), 5.79 and 5.73 (AB q, J=6.8 Hz, 2H), 4.28 (dd, J=7.6, 4.8 Hz, 1H), 3.70-3.68 (m, 1H), 3.29-3.25 (m, 1H), 3.14-3.08 (m, 1H), 2.97 (br d, J=19.2 Hz, 1H), 2.78 (dd, J=16.0, 5.2 Hz, 1H), 2.73-2.66 (m, 1H), 2.54-2.44 (m, 2H), 1.95 (d, J=12.4 Hz, 1H), 1.87-1.78 (m, 1H), 1.72 (d, J=13.6 Hz, 1H), 1.59-1.42 (m, 4H), 1.34-1.21 (m, 2H), 1.17 (s, 9H), 1.12-1.07 (m, 1H).

MH+ 358.

Example 104

(+)-(Morphinan-3-yloxy)methyl pivalate L-(+)-lactic acid

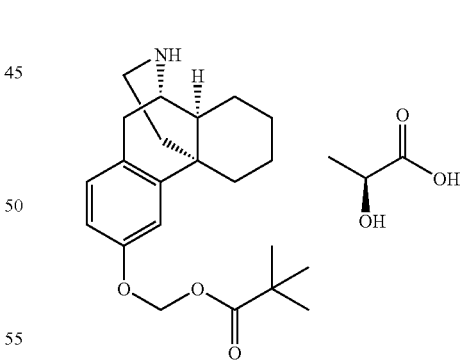

$^1$H NMR (400 MHz, CD$_3$OD) δ 7.12 (d, J=8.8 Hz, 1H), 7.00 (d, J=2.4 Hz, 1H), 6.88 (dd, J=8.4, 2.8 Hz, 1H), 5.77 and 5.71 (AB q, J=6.8 Hz, 2H), 4.01 (q, J=6.8 Hz, 1H), 3.41-3.38 (m, 1H), 3.30-3.29 (m, 1H), 3.18 (dd, J=18.8, 6.4 Hz, 1H), 2.93-2.86 (m, 2H), 2.63-2.56 (m, 1H), 2.39 (d, J=13.6 Hz, 1H), 1.90 (d, J=12.4 Hz, 1H), 1.79-1.71 (m, 1H), 1.66 (d, J=10.4 Hz, 1H), 1.55-1.35 (m, 4H), 1.32 (d, J=6.8 Hz, 6H), 1.28-1.20 (m, 2H), 1.16 (s, 9H), 1.13-1.03 (m, 1H).

MH+ 358.

Example 105

(+)-(Morphinan-3-yloxy)methyl pivalate salicylic acid

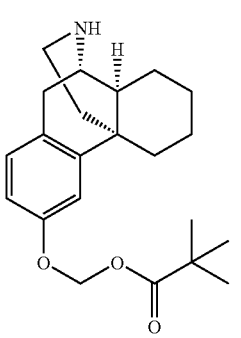

$^1$H NMR (400 MHz, CD$_3$OD) δ 7.81 (dd, J=8.0, 2.0 Hz, 1H), 7.27-7.23 (m, 1H), 7.17 (d, J=8.4 Hz, 1H), 7.05 (d, J=2.4 Hz, 1H), 6.94 (dd, J=8.4, 2.4 Hz, 1H), 6.77-6.72 (m, 2H), 5.79 and 5.73 (AB q, J=6.4 Hz, 2H), 3.65 (br, 1H), 3.25 (d, J=6.0 Hz, 1H), 3.08 (dd, J=13.2, 3.6 Hz, 1H), 2.95 (br d, J=19.2 Hz, 1H), 2.72-2.65 (m, 1H), 2.45 (d, J=14.0 Hz, 1H), 1.93 (d, J=12.4 Hz, 1H), 1.85-1.77 (m, 1H), 1.68 (d, J=12.4 Hz, 1H), 1.58-1.39 (m, 4H), 1.34-1.21 (m, 2H), 1.17 (s, 9H), 1.10-1.06 (m, 1H).

MH+ 358.

What is claimed is:

1. A compound of Formula (I) or a pharmaceutically acceptable salt thereof:

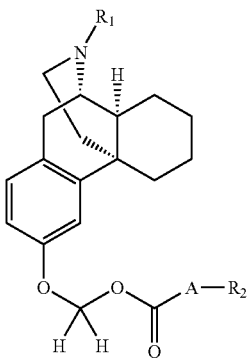

wherein,

A is a direct bond or oxygen;

R$_1$ is selected from the group consisting of hydrogen, —C(O)OC$_{1-10}$ alkyl, substituted —C(O)OC$_{1-10}$ alkyl, —C(O)OC$_{1-4}$ alkyl-Ar and substituted —C(O)OC$_{1-4}$ alkyl-Ar, Ar being selected from the group consisting of phenyl, naphthyl, furyl, pyridyl, thienyl, thiazolyl, isothiazolyl, pyrazolyl, triazolyl, tetrazolyl, imidazolyl, imidazolidinyl, benzofuranyl, indolyl, thiazolidinyl, isoxazolyl, oxadiazolyl, thiadiazolyl, morpholinyl, piperidinyl, piperazinyl, pyrrolyl, and pyrimidinyl, all of which are optionally substituted by one or more Z groups, Z being independently selected from the group consisting of C$_{1-4}$ alkyl, C$_{1-4}$ alkoxy, —(CH$_2$)$_m$C(O)OR$_3$, C(O)NR$_3$R$_4$, —CN, —(CH$_2$)$_n$OH, —NO$_2$, F, Cl, Br, I, —NR$_3$R$_4$ and NHC(O)R$_3$, wherein m is 0 to 4, n is 0 to 4, R$_3$ is hydrogen, C$_{1-6}$ alkyl or substituted C$_{1-6}$ alkyl, and R$_4$ is selected from the group consisting of C$_{1-6}$ alkyl, substituted C$_{1-6}$ alkyl, —CH$_2$Ar and Ar, Ar being as defined above; and R$_2$ is selected from the group consisting of C$_{1-10}$ alkyl, substituted C$_{1-10}$ alkyl, C$_{3-10}$ carbocycle, substituted C$_{3-10}$ carbocycle, (CH$_2$)$_n$-phenyl and substituted (CH$_2$)$_{17}$-phenyl, wherein n is 0 to 4.

2. The compound according to claim 1, wherein the compound has formula (Ia):

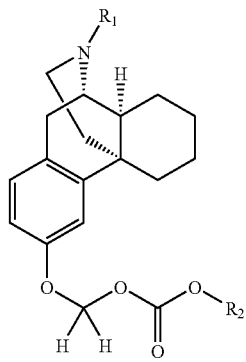

wherein, R$_1$ and R$_2$ are as defined in claim 1.

3. The compound according to claim 1, wherein the compound has formula (Ib):

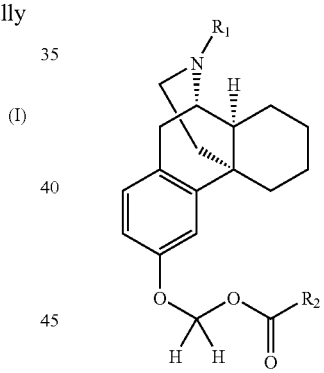

wherein, R$_1$ and R$_2$ are as defined in claim 1.

4. The compound according to claim 1, wherein R$_1$ is hydrogen, —C(O)OC$_{1-4}$ alkyl-Ar or substituted —C(O)OC$_{1-4}$ alkyl-Ar, Ar being phenyl or naphthyl, both of which are optionally substituted by one or more Z groups, Z being independently selected from the group consisting of C$_{1-4}$ alkyl, C$_{1-4}$ alkoxy, —(CH$_2$)$_m$C(O)OR$_3$, C(O)NR$_3$R$_4$, —CN, —(CH$_2$)$_n$OH, —NO$_2$, F, Cl, Br, I, —NR$_3$R$_4$ and NHC(O)R$_3$, wherein m is 0 to 4, n is 0 to 4, R$_3$ is hydrogen, C$_{1-6}$ alkyl or substituted C$_{1-6}$ alkyl, and R$_4$ is selected from the group consisting of C$_{1-6}$ alkyl, substituted C$_{1-6}$ alkyl, —CH$_2$Ar and Ar, Ar being as defined above; and R$_2$ is selected from the group consisting of C$_{1-10}$ alkyl, substituted C$_{1-10}$ alkyl, C$_{3-10}$ carbocycle, substituted C$_{3-10}$ carbocycle, (CH$_2$)$_n$-phenyl and substituted (CH$_2$)$_n$-phenyl, wherein n is 0 to 4.

5. The compound according to claim 1, which is selected from the group consisting of:

(+)-Isopropyl(morphinan-3-yloxy)methyl carbonate;

(+)-(Morphinan-3-yloxy)methyl propyl carbonate;

(+)-Cyclopropylmethyl(morphinan-3-yloxy)methyl carbonate;
(+)-Cyclopentyl(morphinan-3-yloxy)methyl carbonate;
(+)-Cyclohexyl(morphinan-3-yloxy)methyl carbonate;
(+)-Cyclohexylmethyl(morphinan-3-yloxy)methyl carbonate;
(+)-Heptan-4-yl(morphinan-3-yloxy)methyl carbonate;
(+)-Decahydronaphthalen-2-yl(morphinan-3-yloxy)methyl carbonate;
(+)-Decahydronaphthalen-1-yl(morphinan-3-yloxy)methyl carbonate;
(+)-Cyclopentylmethyl(morphinan-3-yloxy)methyl carbonate TFA;
(+)-Cyclobutylmethyl(morphinan-3-yloxy)methyl carbonate TFA;
(+)-2-Ethylhexyl(morphinan-3-yloxy)methyl carbonate TFA;
(+)-Butyl(morphinan-3-yloxy)methyl carbonate TFA;
(+)-Isobutyl(morphinan-3-yloxy)methyl carbonate TFA;
(+)-sec-Butyl(morphinan-3-yloxy)methyl carbonate TFA;
(+)-Cycloheptyl(morphinan-3-yloxy)methyl carbonate TFA;
(+)-(Morphinan-3-yloxy)methyl phenethyl carbonate TFA;
(+)-(Morphinan-3-yloxy)methyl 1-phenylpropan-2-yl carbonate TFA;
(+)-Ethyl(morphinan-3-yloxy)methyl carbonate TFA;
(+)-Methyl(morphinan-3-yloxy)methyl carbonate TFA;
(+)-Cyclobutyl(morphinan-3-yloxy)methyl carbonate TFA;
(+)-Hexyl(morphinan-3-yloxy)methyl carbonate TFA
(+)-(Morphinan-3-yloxy)methyl pentan-2-yl carbonate TFA
(+)-Decyl(morphinan-3-yloxy)methyl carbonate TFA;
(+)-(Morphinan-3-yloxy)methyl isobutyrate;
(+)-(Morphinan-3-yloxy)methyl pivalate;
(+)-(Morphinan-3-yloxy)methyl pivalate TFA;
(+)-(Morphinan-3-yloxy)methyl 3,3-dimethylbutanoate TFA;
(+)-(Morphinan-3-yloxy)methyl hexanoate TFA;
(+)-(Morphinan-3-yloxy)methyl 2-propylpentanoate TFA;
(+)-(Morphinan-3-yloxy)methyl 2-ethylbutanoate TFA;
(+)-(Morphinan-3-yloxy)methyl cyclohexanoate TFA;
(+)-(Morphinan-3-yloxy)methyl cyclopentanoate TFA;
(+)-(Morphinan-3-yloxy)methyl 2-ethylhexanoate TFA;
(+)-(Morphinan-3-yloxy)methyl butanoate TFA;
(+)-(Morphinan-3-yloxy)methyl pentanoate TFA;
(+)-(Morphinan-3-yloxy)methyl 2-methylbutanoate TFA;
(+)-(Morphinan-3-yloxy)methyl cyclopropanecarboxylate TFA;
(+)-(Morphinan-3-yloxy)methyl 3-methylbutanoate TFA;
(+)-(Morphinan-3-yloxy)methyl 2-phenylbutanoate TFA;
(+)-(Morphinan-3-yloxy)methyl 1-adamantanecarboxylate TFA;
(+)-(Morphinan-3-yloxy)methyl acetate TFA;
(+)-(Morphinan-3-yloxy)methyl 3-cylcohexylpropanoate TFA;
(+)-(Morphinan-3-yloxy)methyl 3,5,5-trimethylhexanoate TFA;
(+)-Isopropyl(morphinan-3-yloxy)methyl carbonate TFA;
(+)-Isopropyl(morphinan-3-yloxy)methyl carbonate L-(+)-tartaric acid;
(+)-Isopropyl(morphinan-3-yloxy)methyl carbonate HCl;
(+)-Isopropyl(morphinan-3-yloxy)methyl carbonate formic acid;
(+)-Isopropyl(morphinan-3-yloxy)methyl carbonate citric acid;
(+)-Isopropyl(morphinan-3-yloxy)methyl carbonate fumaric acid;
(+)-Isopropyl(morphinan-3-yloxy)methyl carbonate fumaric acid mono-Na;
(+)-Isopropyl(morphinan-3-yloxy)methyl carbonate 4-methylbenzenesulfonic acid;
(+)-Isopropyl(morphinan-3-yloxy)methyl carbonate stearic acid;
(+)-Isopropyl(morphinan-3-yloxy)methyl carbonate citric acid di-Na;
(+)-Isopropyl(morphinan-3-yloxy)methyl carbonate L-(−)-malic acid;
(+)-Isopropyl(morphinan-3-yloxy)methyl carbonate L-(+)-lactic acid;
(+)-Isopropyl(morphinan-3-yloxy)methyl carbonate succinic acid;
(+)-Isopropyl(morphinan-3-yloxy)methyl carbonate salicylic acid;
(+)-(Morphinan-3-yloxy)methyl pivalate succinic acid;
(+)-(Morphinan-3-yloxy)methyl pivalate HCl;
(+)-(Morphinan-3-yloxy)methyl pivalate formic acid;
(+)-(Morphinan-3-yloxy)methyl pivalate citric acid;
(+)-(Morphinan-3-yloxy)methyl pivalate fumaric acid;
(+)-(Morphinan-3-yloxy)methyl pivalate fumaric acid mono-Na;
(+)-(Morphinan-3-yloxy)methyl pivalate 4-methylbenzenesulfonic acid;
(+)-(Morphinan-3-yloxy)methyl pivalate stearic acid;
(+)-(Morphinan-3-yloxy)methyl pivalate citric acid di-Na;
(+)-(Morphinan-3-yloxy)methyl pivalate L-(+)-tartaric acid;
(+)-(Morphinan-3-yloxy)methyl pivalate L-(−)-malic acid;
(+)-(Morphinan-3-yloxy)methyl pivalate L-(+)-lactic acid;
(+)-(Morphinan-3-yloxy)methyl pivalate salicylic acid;
(+)-[N-(Benzyloxycarbonyl)morphinan-3-yloxy]methyl isopropyl carbonate;
(+)-[N-(Benzyloxycarbonyl)morphinan-3-yloxy]methyl cyclopentyl carbonate;
(+)-[N-(Benzyloxycarbonyl)morphinan-3-yloxy]methyl cyclohexyl carbonate;
(+)-[N-(Benzyloxycarbonyl)morphinan-3-yloxy]methyl decahydronaphthalen-1-yl carbonate;
(+)-[N-(Benzyloxycarbonyl)morphinan-3-yloxy]methyl cyclopentylmethyl carbonate;
(+)[N-(Benzyloxycarbonyl)morphinan-3-yloxy]methyl cyclobutylmethyl carbonate;
(+)-[N-(Benzyloxycarbonyl)morphinan-3-yloxy]methyl 2-ethylhexyl carbonate;
(+)-[N-(Benzyloxycarbonyl)morphinan-3-yloxy]methyl butyl carbonate;
(+)[N-(Benzyloxycarbonyl)morphinan-3-yloxy]methyl isobutyl carbonate;
(+)-[N-(Benzyloxycarbonyl)morphinan-3-yloxy]methyl sec-butyl carbonate;
(+)-[N-(Benzyloxycarbonyl)morphinan-3-yloxy]methyl cycloheptyl carbonate;
(+)-[N-(Benzyloxycarbonyl)morphinan-3-yloxy]methyl phenethyl carbonate;
(+)-[N-(Benzyloxycarbonyl)morphinan-3-yloxy]methyl 1-phenylpropan-2-yl carbonate;
(+)-[N-(Benzyloxycarbonyl)morphinan-3-yloxy]methyl ethyl carbonate;

(+)-[N-(Benzyloxycarbonyl)morphinan-3-yloxy]methyl methyl carbonate;
(+)-[N-(Benzyloxycarbonyl)morphinan-3-yloxy]methyl cyclobutyl carbonate;
(+)-[N-(Benzyloxycarbonyl)morphinan-3-yloxy]methyl hexyl carbonate;
(+)-[N-(Benzyloxycarbonyl)morphinan-3-yloxy]methyl pentan-2-yl carbonate;
(+)[N-(Benzyloxycarbonyl)morphinan-3-yloxy]methyl isobutyrate;
(+)-[N-(Benzyloxycarbonyl)morphinan-3-yloxy]methyl pivalate;
(+)[N-(Benzyloxycarbonyl)morphinan-3-yloxy]methyl hexanoate;
(+)-[N-(Benzyloxycarbonyl)morphinan-3-yloxy]methyl 2-propylpentanoate;
(+)-[N-(Benzyloxycarbonyl)morphinan-3-yloxy]methyl 2-ethylbutanoate;
(+)[N-(Benzyloxycarbonyl)morphinan-3-yloxy]methyl cyclohexanoate;
(+)-[N-(Benzyloxycarbonyl)morphinan-3-yloxy]methyl cyclopentanoate;
(+)-[N-(Benzyloxycarbonyl)morphinan-3-yloxy]methyl 2-ethylhexanoate;
(+)-[N-(Benzyloxycarbonyl)morphinan-3-yloxy]methyl butanoate;
(+)-[N-(Benzyloxycarbonyl)morphinan-3-yloxy]methyl pentanoate;
(+)-[N-(Benzyloxycarbonyl)morphinan-3-yloxy]methyl 2-methylbutanoate;
(+)-[N-(Benzyloxycarbonyl)morphinan-3-yloxy]methyl cyclopropanecarboxylate;
(+)-[N-(Benzyloxycarbonyl)morphinan-3-yloxy]methyl 3-methylbutanoate;
(+)-[N-(Benzyloxycarbonyl)morphinan-3-yloxy]methyl 2-phenylbutanoate;
(+)-[N-(Benzyloxycarbonyl)morphinan-3-yloxy]methyl 1-adamantanecarboxylate; and
(+)[N-(Benzyloxycarbonyl)morphinan-3-yloxy]methyl 3,5,5-trimethylhexanoate.

6. A pharmaceutical composition comprising the compound according to claim 1 or a pharmaceutically acceptable salt thereof, and a pharmaceutically acceptable carrier.

7. A method for treating Parkinson's disease, comprising administering to a patient in need of treatment thereof the compound according to claim 1 or a pharmaceutically acceptable salt thereof.

\* \* \* \* \*